(12) United States Patent
Christianson et al.

(10) Patent No.: US 11,273,032 B2
(45) Date of Patent: Mar. 15, 2022

(54) COLLAPSIBLE INNER FLOW CONTROL COMPONENT FOR SIDE-DELIVERABLE TRANSCATHETER HEART VALVE PROSTHESIS

(71) Applicant: VDyne, Inc., Maple Grove, MN (US)

(72) Inventors: Mark Christianson, Plymouth, MN (US); Robert Vidlund, Forest Lake, MN (US); Neelakantan Saikrishnan, Plymouth, MN (US); Chad Perrin, Andover, MN (US)

(73) Assignee: VDyne, Inc., Maple Grove, MN (US)

( * ) Notice: Subject to any disclaimer, the term of this patent is extended or adjusted under 35 U.S.C. 154(b) by 0 days.

(21) Appl. No.: 17/222,182

(22) Filed: Apr. 5, 2021

(65) Prior Publication Data
US 2021/0244536 A1 Aug. 12, 2021

Related U.S. Application Data

(63) Continuation of application No. PCT/US2020/015231, filed on Jan. 27, 2020, which
(Continued)

(51) Int. Cl.
*A61F 2/24* (2006.01)
*B33Y 80/00* (2015.01)

(52) U.S. Cl.
CPC .......... *A61F 2/2418* (2013.01); *A61F 2/2427* (2013.01); *B33Y 80/00* (2014.12);
(Continued)

(58) Field of Classification Search
CPC ...... A61F 2/24; A61F 2/07; A61F 2/06; A61F 2/2418; A61F 2/2436; A61F 2/2412; A61F 2/2409
See application file for complete search history.

(56) References Cited

U.S. PATENT DOCUMENTS 3,744,060 A 7/1973 Bellhouse et al.
4,079,468 A 3/1978 Liotta et al.
(Continued)

FOREIGN PATENT DOCUMENTS

AU 2006203686 B2 11/2008
AU 2009219415 A1 9/2009
(Continued)

OTHER PUBLICATIONS

Office Action for U.S. Appl. No. 16/435,687, dated Aug. 7, 2019, 19 pages.
(Continued)

*Primary Examiner* — Seema Mathew
(74) *Attorney, Agent, or Firm* — Cooley LLP

(57) ABSTRACT

A side-deliverable prosthetic heart valve includes an outer frame and a flow control component. The outer frame defines a central channel that extends along a central axis. The flow control component is disposed within the central channel and coupled to the outer frame. The flow control component has a set of leaflets mounted within an inner frame. The prosthetic valve is configured to be folded along a longitudinal axis and compressed along the central axis to place the prosthetic valve in a compressed configuration for delivery via a delivery catheter. The longitudinal axis is substantially parallel to a lengthwise axis of the delivery catheter when disposed therein. The prosthetic valve transitions to an expanded configuration when released from the delivery catheter. The flow control component elastically deforms from a substantially cylindrical configuration to a substantially flattened configuration when the prosthetic valve is placed in the compressed configuration.

30 Claims, 41 Drawing Sheets

Related U.S. Application Data is a continuation-in-part of application No. 16/455,740, filed on Jun. 27, 2019, now Pat. No. 11,185,409, application No. 17/222,182, filed on Apr. 5, 2021, which is a continuation-in-part of application No. 16/455,740, filed on Jun. 27, 2019, now Pat. No. 11,185,409.

(60) Provisional application No. 62/797,201, filed on Jan. 26, 2019.

(52) U.S. Cl.
CPC ..... *A61F 2/2436* (2013.01); *A61F 2210/0014* (2013.01); *A61F 2220/0008* (2013.01)

(56) References Cited

U.S. PATENT DOCUMENTS

| | | |
|---|---|---|
| 5,397,351 A | 3/1995 | Pavcnik et al. |
| 5,509,428 A | 4/1996 | Dunlop |
| 5,554,185 A | 9/1996 | Block et al. |
| 6,006,134 A | 12/1999 | Hill et al. |
| 6,197,013 B1 | 3/2001 | Reed et al. |
| 6,290,719 B1 | 9/2001 | Garberoglio |
| 6,312,464 B1 * | 11/2001 | Navia ............... A61F 2/2427 128/898 |
| 6,449,507 B1 | 9/2002 | Hill et al. |
| 6,458,153 B1 | 10/2002 | Bailey et al. |
| 6,532,388 B1 | 3/2003 | Hill et al. |
| 6,582,467 B1 | 6/2003 | Teitelbaum et al. |
| 6,628,987 B1 | 9/2003 | Hill et al. |
| 6,669,724 B2 | 12/2003 | Park et al. |
| 6,718,208 B2 | 4/2004 | Hill et al. |
| 6,769,434 B2 | 8/2004 | Liddicoat et al. |
| 6,890,330 B2 | 5/2005 | Streeter et al. |
| 6,896,690 B1 | 5/2005 | Lambrecht et al. |
| 6,904,318 B2 | 6/2005 | Hill et al. |
| 6,929,653 B2 | 8/2005 | Strecter |
| 7,074,189 B1 | 7/2006 | Montegrande |
| 7,125,418 B2 | 10/2006 | Duran et al. |
| 7,175,660 B2 | 2/2007 | Cartledge et al. |
| 7,201,761 B2 | 4/2007 | Woolfson et al. |
| 7,225,019 B2 | 5/2007 | Jahns et al. |
| 7,269,457 B2 | 9/2007 | Shafer et al. |
| 7,331,991 B2 | 2/2008 | Kheradvar et al. |
| 7,361,189 B2 | 4/2008 | Case et al. |
| 7,374,571 B2 | 5/2008 | Pease et al. |
| 7,442,204 B2 | 10/2008 | Schwammenthal et al. |
| 7,449,027 B2 | 11/2008 | Hunt et al. |
| 7,621,948 B2 | 11/2009 | Herrmann et al. |
| 7,648,527 B2 | 1/2010 | Agnew |
| 7,717,952 B2 | 5/2010 | Case et al. |
| 7,749,245 B2 | 7/2010 | Cohn et al. |
| 7,753,949 B2 | 7/2010 | Lamphere et al. |
| 7,811,316 B2 | 10/2010 | Kalmann et al. |
| 7,828,840 B2 | 11/2010 | Biggs et al. |
| 7,846,199 B2 | 12/2010 | Paul, Jr. et al. |
| 8,303,648 B2 | 11/2012 | Grewe et al. |
| 8,366,768 B2 | 2/2013 | Zhang |
| 8,491,650 B2 | 7/2013 | Wiemeyer et al. |
| 8,568,474 B2 | 10/2013 | Yeung et al. |
| 8,628,571 B1 * | 1/2014 | Hacohen ............ A61F 2/2403 623/2.2 |
| 8,641,752 B1 | 2/2014 | Holm et al. |
| 8,696,743 B2 | 4/2014 | Holecek et al. |
| 8,728,153 B2 | 5/2014 | Bishop et al. |
| 8,758,395 B2 | 6/2014 | Kleshinski et al. |
| 8,846,390 B2 | 9/2014 | Dove et al. |
| 8,876,892 B2 | 11/2014 | Tran et al. |
| 8,900,295 B2 | 12/2014 | Migliazza et al. |
| 8,915,958 B2 | 12/2014 | Braido |
| 8,926,690 B2 | 1/2015 | Kovalsky |
| 8,926,692 B2 | 1/2015 | Dwork |
| 8,926,694 B2 | 1/2015 | Costello |
| 8,940,044 B2 | 1/2015 | Hammer et al. |
| 8,956,404 B2 | 2/2015 | Bortlein et al. |
| 8,986,370 B2 | 3/2015 | Annest et al. |
| 9,011,524 B2 | 4/2015 | Eberhardt |
| 9,017,399 B2 | 4/2015 | Gross et al. |
| 9,050,188 B2 | 6/2015 | Schweich, Jr. et al. |
| 9,072,604 B1 | 7/2015 | Melnick et al. |
| 9,119,714 B2 | 9/2015 | Shandas et al. |
| 9,216,076 B2 | 12/2015 | Mitra et al. |
| 9,232,995 B2 | 1/2016 | Kovalsky et al. |
| 9,241,792 B2 | 1/2016 | Benichou et al. |
| 9,248,016 B2 | 2/2016 | Oba et al. |
| 9,259,215 B2 | 2/2016 | Chou et al. |
| 9,277,990 B2 | 3/2016 | Klima et al. |
| 9,289,282 B2 | 3/2016 | Olson et al. |
| 9,289,296 B2 | 3/2016 | Braido et al. |
| 9,295,547 B2 | 3/2016 | Costello et al. |
| 9,301,839 B2 | 4/2016 | Stante et al. |
| 9,308,086 B2 | 4/2016 | Ho |
| 9,339,367 B2 | 5/2016 | Carpenter et al. |
| 9,370,418 B2 | 6/2016 | Pintor et al. |
| 9,381,083 B2 | 7/2016 | Costello |
| 9,387,075 B2 | 7/2016 | Bortlein et al. |
| 9,393,111 B2 | 7/2016 | Ma et al. |
| 9,414,915 B2 | 8/2016 | Lombardi et al. |
| 9,433,500 B2 | 9/2016 | Chau et al. |
| 9,440,054 B2 | 9/2016 | Bishop et al. |
| 9,456,899 B2 | 10/2016 | Yeung et al. |
| 9,468,525 B2 | 10/2016 | Kovalsky et al. |
| 9,474,604 B2 | 10/2016 | Centola et al. |
| 9,486,306 B2 | 11/2016 | Tegels et al. |
| 9,510,941 B2 | 12/2016 | Bishop et al. |
| 9,554,902 B2 | 1/2017 | Braido et al. |
| 9,579,196 B2 | 2/2017 | Morriss et al. |
| 9,579,200 B2 | 2/2017 | Lederman et al. |
| 9,610,159 B2 | 4/2017 | Christianson et al. |
| 9,615,925 B2 | 4/2017 | Subramanian et al. |
| 9,629,719 B2 | 4/2017 | Rothstein |
| 9,636,222 B2 | 5/2017 | Oslund |
| 9,649,191 B2 | 5/2017 | Savage et al. |
| 9,662,202 B2 | 5/2017 | Quill et al. |
| 9,662,203 B2 | 5/2017 | Sheahan et al. |
| 9,662,209 B2 | 5/2017 | Gross et al. |
| 9,675,454 B2 | 6/2017 | Vidlund et al. |
| 9,675,485 B2 | 6/2017 | Essinger et al. |
| 9,687,343 B2 | 6/2017 | Bortlein et al. |
| 9,707,076 B2 | 7/2017 | Stack et al. |
| 9,713,530 B2 | 7/2017 | Cabiri et al. |
| 9,750,607 B2 | 9/2017 | Ganesan et al. |
| 9,763,778 B2 | 9/2017 | Eidenschink et al. |
| 9,763,779 B2 | 9/2017 | Bortlein et al. |
| 9,788,946 B2 | 10/2017 | Bobo, Jr. et al. |
| 9,839,511 B2 | 12/2017 | Ma et al. |
| 9,849,011 B2 | 12/2017 | Zimmerman et al. |
| 9,855,384 B2 | 1/2018 | Cohen et al. |
| 9,861,464 B2 | 1/2018 | Azimpour et al. |
| 9,895,219 B2 | 2/2018 | Costello et al. |
| 9,901,330 B2 | 2/2018 | Akpinar |
| 9,918,838 B2 | 3/2018 | Ring |
| 9,943,409 B2 | 4/2018 | Kim et al. |
| 9,949,825 B2 | 4/2018 | Braido et al. |
| 9,968,444 B2 | 5/2018 | Millwee et al. |
| 9,968,445 B2 | 5/2018 | Kheradvar |
| 9,980,815 B2 | 5/2018 | Nitzan et al. |
| 9,987,121 B2 | 6/2018 | Blanzy |
| 10,010,411 B2 | 7/2018 | Peter |
| 10,010,412 B2 | 7/2018 | Taft et al. |
| 10,022,054 B2 | 7/2018 | Najafi et al. |
| 10,022,222 B2 | 7/2018 | Groothuis et al. |
| 10,022,223 B2 | 7/2018 | Bruchman |
| 10,028,821 B2 | 7/2018 | Centola et al. |
| 10,028,831 B2 | 7/2018 | Morin et al. |
| 10,034,667 B2 | 7/2018 | Morris et al. |
| 10,034,747 B2 | 7/2018 | Harewood |
| 10,039,638 B2 | 8/2018 | Bruchman et al. |
| 10,058,315 B2 | 8/2018 | Rafiee et al. |
| 10,058,411 B2 | 8/2018 | Fifer et al. |
| 10,058,421 B2 | 8/2018 | Eberhardt et al. |
| 10,058,426 B2 | 8/2018 | Barbarino |
| 10,064,405 B2 | 9/2018 | Dale et al. |

(56) References Cited

U.S. PATENT DOCUMENTS

| | | |
|---|---|---|
| 10,080,653 B2 | 9/2018 | Conklin et al. |
| 10,085,835 B2 | 10/2018 | Thambar et al. |
| 10,105,224 B2 | 10/2018 | Buchbinder et al. |
| 10,117,741 B2 | 11/2018 | Schweich, Jr. et al. |
| 10,123,874 B2 | 11/2018 | Khairkhahan et al. |
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1 | 6/2019 | Christianson et al. |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,976 B2 | 11/2019 | Streeter et al. |
| 10,595,994 B1 | 3/2020 | Christianson et al. |
| 10,631,983 B1 | 4/2020 | Christianson et al. |
| 10,653,522 B1 * | 5/2020 | Vidlund ............... A61F 2/2433 |
| 10,758,346 B1 | 9/2020 | Christianson et al. |
| 11,071,627 B2 | 7/2021 | Saikrishnan et al. |
| 11,076,956 B2 | 8/2021 | Christianson et al. |
| 11,109,969 B2 | 9/2021 | Vidlund et al. |
| 11,166,814 B2 | 11/2021 | Vidlund, I et al. |
| 11,173,027 B2 | 11/2021 | Christianson et al. |
| 11,179,239 B2 | 11/2021 | Vidlund et al. |
| 11,185,409 B2 | 11/2021 | Christianson et al. |
| 2003/0040772 A1 | 2/2003 | Hyodoh et al. |
| 2003/0040808 A1 | 2/2003 | Stack et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0049207 A1 | 3/2004 | Goldfarb et al. |
| 2004/0088047 A1 | 5/2004 | Spence et al. |
| 2004/0093060 A1 | 5/2004 | Seguin et al. |
| 2004/0116996 A1 | 6/2004 | Freitag |
| 2004/0199209 A1 | 10/2004 | Hill et al. |
| 2004/0225352 A1 | 11/2004 | Osborne et al. |
| 2005/0010246 A1 | 1/2005 | Streeter et al. |
| 2005/0075659 A1 | 4/2005 | Realyvasquez et al. |
| 2005/0075725 A1 | 4/2005 | Rowe |
| 2005/0107811 A1 | 5/2005 | Starksen et al. |
| 2005/0137686 A1 | 6/2005 | Salahieh et al. |
| 2005/0228495 A1 | 10/2005 | Macoviak |
| 2006/0015167 A1 | 1/2006 | Armstrong et al. |
| 2006/0190075 A1 | 8/2006 | Jordan et al. |
| 2006/0195180 A1 * | 8/2006 | Kheradvar ............ A61F 2/2418 623/2.11 |
| 2006/0229708 A1 | 10/2006 | Powell et al. |
| 2006/0241745 A1 | 10/2006 | Solem |
| 2006/0271098 A1 | 11/2006 | Peacock, III |
| 2006/0276887 A1 | 12/2006 | Brady et al. |
| 2007/0016286 A1 | 1/2007 | Herrmann et al. |
| 2007/0027535 A1 | 2/2007 | Purdy, Jr. et al. |
| 2007/0032850 A1 | 2/2007 | Ruiz et al. |
| 2007/0038295 A1 | 2/2007 | Case et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt et al. |
| 2007/0239271 A1 | 10/2007 | Nguyen |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0065204 A1 | 3/2008 | Macoviak et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0154355 A1 | 6/2008 | Benichou et al. |
| 2008/0183279 A1 | 7/2008 | Bailey et al. |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0262592 A1 | 10/2008 | Jordan et al. |
| 2008/0262609 A1 | 10/2008 | Gross et al. |
| 2008/0275550 A1 | 11/2008 | Kheradvar et al. |
| 2009/0005863 A1 | 1/2009 | Goetz et al. |
| 2009/0054976 A1 | 2/2009 | Tuval et al. |
| 2009/0094189 A1 | 4/2009 | Stephens |
| 2009/0192586 A1 | 7/2009 | Tabor et al. |
| 2009/0254174 A1 | 10/2009 | Case et al. |
| 2009/0264991 A1 | 10/2009 | Paul, Jr. et al. |
| 2009/0287290 A1 | 11/2009 | Macaulay et al. |
| 2010/0049294 A1 | 2/2010 | Zukowski et al. |
| 2010/0049313 A1 | 2/2010 | Alon et al. |
| 2010/0121434 A1 | 5/2010 | Paul et al. |
| 2010/0160773 A1 | 6/2010 | Cohen et al. |
| 2010/0161043 A1 | 6/2010 | Maisano et al. |
| 2010/0168844 A1 | 7/2010 | Toomes et al. |
| 2010/0174363 A1 | 7/2010 | Castro |
| 2010/0179583 A1 | 7/2010 | Carpenter et al. |
| 2010/0179584 A1 | 7/2010 | Carpenter et al. |
| 2010/0179647 A1 | 7/2010 | Carpenter et al. |
| 2010/0280591 A1 | 11/2010 | Shin et al. |
| 2010/0298929 A1 | 11/2010 | Thornton et al. |
| 2010/0305685 A1 | 12/2010 | Millwee et al. |
| 2011/0004237 A1 | 1/2011 | Schneider et al. |
| 2011/0029071 A1 | 2/2011 | Zlotnick et al. |
| 2011/0029072 A1 | 2/2011 | Gabbay |
| 2011/0066233 A1 | 3/2011 | Thornton et al. |
| 2011/0071613 A1 | 3/2011 | Wood et al. |
| 2011/0098804 A1 | 4/2011 | Yeung et al. |
| 2011/0125145 A1 | 5/2011 | Mody et al. |
| 2011/0137397 A1 | 6/2011 | Chau et al. |
| 2011/0160836 A1 | 6/2011 | Behan |
| 2011/0172764 A1 | 7/2011 | Badhwar |
| 2011/0224785 A1 | 9/2011 | Hacohen et al. |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035701 A1 | 2/2012 | To |
| 2012/0065723 A1 | 3/2012 | Drasler et al. |
| 2012/0083874 A1 | 4/2012 | Dale et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim et al. |
| 2012/0277853 A1 | 11/2012 | Rothstein |
| 2012/0310327 A1 | 12/2012 | McHugo |
| 2012/0310328 A1 | 12/2012 | Olson et al. |
| 2013/0035759 A1 | 2/2013 | Gross et al. |
| 2013/0055941 A1 | 3/2013 | Holecek et al. |

(56) References Cited

U.S. PATENT DOCUMENTS

| | | |
|---|---|---|
| 2013/0131714 A1 | 5/2013 | Wang et al. |
| 2013/0131792 A1 | 5/2013 | Miller et al. |
| 2013/0166017 A1 | 6/2013 | Cartledge et al. |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian et al. |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. et al. |
| 2013/0297010 A1 | 11/2013 | Bishop et al. |
| 2013/0304197 A1 | 11/2013 | Buchbinder et al. |
| 2013/0304200 A1* | 11/2013 | McLean ............... A61F 2/2436 623/2.18 |
| 2013/0331929 A1 | 12/2013 | Mitra et al. |
| 2013/0338764 A1 | 12/2013 | Thornton et al. |
| 2014/0000112 A1 | 1/2014 | Braido et al. |
| 2014/0005540 A1 | 1/2014 | Merhi |
| 2014/0005768 A1 | 1/2014 | Thomas et al. |
| 2014/0005778 A1* | 1/2014 | Buchbinder ......... A61F 2/2412 623/2.18 |
| 2014/0012372 A1 | 1/2014 | Chau et al. |
| 2014/0018915 A1 | 1/2014 | Baidillah et al. |
| 2014/0039511 A1 | 2/2014 | Morris et al. |
| 2014/0039611 A1 | 2/2014 | Lane et al. |
| 2014/0052237 A1 | 2/2014 | Lane et al. |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress et al. |
| 2014/0135908 A1 | 5/2014 | Glozman et al. |
| 2014/0142695 A1 | 5/2014 | Gross et al. |
| 2014/0172070 A1 | 6/2014 | Seguin |
| 2014/0180069 A1 | 6/2014 | Millett |
| 2014/0180070 A1 | 6/2014 | Millett et al. |
| 2014/0194704 A1 | 7/2014 | Millett et al. |
| 2014/0194983 A1 | 7/2014 | Kovalsky et al. |
| 2014/0207231 A1 | 7/2014 | Hacohen et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0249566 A1 | 9/2014 | Quinn et al. |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0296962 A1 | 10/2014 | Cartledge et al. |
| 2014/0296969 A1 | 10/2014 | Tegels et al. |
| 2014/0296975 A1* | 10/2014 | Tegels ............... A61F 2/07 623/2.18 |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0350662 A1 | 11/2014 | Vaturi |
| 2014/0358224 A1 | 12/2014 | Tegels et al. |
| 2014/0371789 A1 | 12/2014 | Hariton et al. |
| 2014/0379076 A1* | 12/2014 | Vidlund ............... A61F 2/2412 623/2.18 |
| 2015/0005808 A1 | 1/2015 | Chouinard et al. |
| 2015/0005874 A1 | 1/2015 | Vidlund et al. |
| 2015/0039081 A1 | 2/2015 | Costello |
| 2015/0045880 A1 | 2/2015 | Hacohen |
| 2015/0051687 A1 | 2/2015 | Dickerhoff et al. |
| 2015/0094802 A1 | 4/2015 | Buchbinder et al. |
| 2015/0112188 A1 | 4/2015 | Stigall et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1 | 8/2015 | Hacohen et al. |
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell et al. |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038280 A1* | 2/2016 | Morriss ............... A61F 2/2409 623/2.18 |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas et al. |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth et al. |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220367 A1 | 8/2016 | Barrett |
| 2016/0220372 A1 | 8/2016 | Medema et al. |
| 2016/0220734 A1 | 8/2016 | Dyamenahalli et al. |
| 2016/0228250 A1 | 8/2016 | Casley et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324633 A1 | 11/2016 | Gross et al. |
| 2016/0324639 A1 | 11/2016 | Nguyen et al. |
| 2016/0331534 A1 | 11/2016 | Buchbinder et al. |
| 2016/0354201 A1 | 12/2016 | Keogh |
| 2016/0361169 A1 | 12/2016 | Gross et al. |
| 2016/0361184 A1 | 12/2016 | Tabor et al. |

(56) References Cited

U.S. PATENT DOCUMENTS

| | | |
|---|---|---|
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056166 A1 | 3/2017 | Ratz et al. |
| 2017/0056171 A1 | 3/2017 | Cooper et al. |
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100246 A1 | 4/2017 | Rust et al. |
| 2017/0112620 A1 | 4/2017 | Curley et al. |
| 2017/0128208 A1 | 5/2017 | Christianson et al. |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0172738 A1 | 6/2017 | Kassas |
| 2017/0181851 A1 | 6/2017 | Annest |
| 2017/0181852 A1 | 6/2017 | Kassas |
| 2017/0189177 A1 | 7/2017 | Schweich, Jr. et al. |
| 2017/0196690 A1 | 7/2017 | Racchini et al. |
| 2017/0209266 A1 | 7/2017 | Lane et al. |
| 2017/0209268 A1 | 7/2017 | Cunningham et al. |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini et al. |
| 2017/0281337 A1 | 10/2017 | Campbell |
| 2017/0281341 A1 | 10/2017 | Lim et al. |
| 2017/0296340 A1 | 10/2017 | Gross et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson et al. |
| 2017/0348100 A1 | 12/2017 | Lane et al. |
| 2017/0360557 A1 | 12/2017 | Kheradvar et al. |
| 2017/0360558 A1 | 12/2017 | Ma |
| 2017/0360561 A1 | 12/2017 | Bell et al. |
| 2018/0014932 A1 | 1/2018 | Hammer et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0099124 A1 | 4/2018 | McLoughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1 | 7/2018 | Chambers et al. |
| 2018/0206983 A1 | 7/2018 | Noe et al. |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1* | 9/2018 | Zhang .................. A61F 2/2439 |
| 2018/0256327 A1 | 9/2018 | Perszyk et al. |
| 2018/0256329 A1 | 9/2018 | Chambers et al. |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1* | 10/2018 | Chung .................. A61F 2/2445 |
| 2018/0289485 A1 | 10/2018 | Rajagopal et al. |
| 2018/0296325 A1 | 10/2018 | McLean |
| 2018/0296335 A1 | 10/2018 | Miyashiro |
| 2018/0296337 A1 | 10/2018 | Duhay et al. |
| 2018/0296341 A1 | 10/2018 | Noe et al. |
| 2018/0303488 A1 | 10/2018 | Hill |
| 2018/0303612 A1 | 10/2018 | Pasquino et al. |
| 2018/0311037 A1 | 11/2018 | Morriss et al. |
| 2018/0311474 A1 | 11/2018 | Tyler, II et al. |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0333259 A1* | 11/2018 | Dibie .................. A61F 2/2418 |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper et al. |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008636 A1* | 1/2019 | Francis .................. A61B 5/068 |
| 2019/0008640 A1 | 1/2019 | Cooper et al. |
| 2019/0015188 A1 | 1/2019 | Eigler et al. |
| 2019/0021834 A1 | 1/2019 | Nir et al. |
| 2019/0029819 A1 | 1/2019 | Huber |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0069995 A1 | 3/2019 | Levi et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |

(56) References Cited

U.S. PATENT DOCUMENTS

| | | |
|---|---|---|
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman et al. |
| 2019/0254816 A1 | 8/2019 | Anderson et al. |
| 2019/0262118 A1 | 8/2019 | Eigler et al. |
| 2019/0262129 A1 | 8/2019 | Cooper et al. |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0365538 A1 | 12/2019 | Chambers et al. |
| 2019/0388219 A1 | 12/2019 | Lane et al. |
| 2020/0121452 A1* | 4/2020 | Saikrishnan ......... A61F 2/2469 |
| 2020/0121458 A1 | 4/2020 | Vidlund et al. |
| 2020/0179146 A1 | 6/2020 | Christianson et al. |
| 2020/0188097 A1 | 6/2020 | Perrin et al. |
| 2020/0237506 A1 | 7/2020 | Christianson et al. |
| 2020/0289259 A1 | 9/2020 | Christianson et al. |
| 2020/0289263 A1 | 9/2020 | Christianson et al. |
| 2021/0000592 A1 | 1/2021 | Christianson et al. |
| 2021/0137677 A1 | 5/2021 | Christianson et al. |
| 2021/0154011 A1 | 5/2021 | Christianson et al. |
| 2021/0186693 A1 | 6/2021 | Vidlund et al. |
| 2021/0220126 A1 | 7/2021 | Perrin |
| 2021/0220127 A1 | 7/2021 | Vidlund et al. |
| 2021/0220134 A1 | 7/2021 | Christianson et al. |
| 2021/0228349 A1 | 7/2021 | Vidlund et al. |
| 2021/0236280 A1 | 8/2021 | Christianson et al. |
| 2021/0244533 A1 | 8/2021 | Vidlund et al. |
| 2021/0290381 A1 | 9/2021 | Vidlund et al. |
| 2021/0290385 A1 | 9/2021 | Christianson et al. |
| 2021/0315694 A1 | 10/2021 | Vidlund et al. |
| 2021/0330459 A1 | 10/2021 | Christianson et al. |
| 2021/0353412 A1 | 11/2021 | Christianson et al. |

FOREIGN PATENT DOCUMENTS

| | | |
|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |

(56) References Cited

FOREIGN PATENT DOCUMENTS

| | | | |
|---|---|---|---|
| CN | 103153232 B | 9/2016 |
| CN | 106061437 A | 10/2016 |
| CN | 106068109 A | 11/2016 |
| CN | 106073946 A | 11/2016 |
| CN | 106255475 A | 12/2016 |
| CN | 103917194 B | 2/2017 |
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |
| CN | 106890035 A | 6/2017 |
| CN | 106943207 A | 7/2017 |
| CN | 106999054 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | 1301225 A2 | 4/2003 |
| EP | 1684666 A2 | 8/2006 |
| EP | 1996246 A2 | 12/2008 |
| EP | 2211779 A1 | 8/2010 |
| EP | 2254513 A1 | 12/2010 |
| EP | 2263605 A1 | 12/2010 |
| EP | 2273947 A1 | 1/2011 |
| EP | 2296744 A1 | 3/2011 |
| EP | 2379008 A2 | 10/2011 |
| EP | 2400926 A2 | 1/2012 |
| EP | 2427145 A2 | 3/2012 |
| EP | 1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 A1 | 4/2015 |
| EP | 2444031 B1 | 7/2015 |
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |
| EP | 3062745 A1 | 9/2016 |
| EP | 3071149 A1 | 9/2016 |
| EP | 2282700 B1 | 11/2016 |
| EP | 2967854 B1 | 11/2016 |
| EP | 1998713 B1 | 12/2016 |
| EP | 3099271 A1 | 12/2016 |
| EP | 3100701 A1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | 3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |

(56) References Cited

FOREIGN PATENT DOCUMENTS

| | | |
|---|---|---|
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | 2560580 B1 | 6/2019 |
| EP | 3508113 A1 | 7/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3552584 A1 | 10/2019 |
| EP | 3552655 A1 | 10/2019 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008091925 A2 | 7/2008 |
| WO | WO-2008103280 A2 | 8/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2010119110 A1 | 10/2010 |
| WO | WO-2011112706 A2 | 9/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |
| WO | WO-2014137805 A1 | 9/2014 |
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |

(56) References Cited

FOREIGN PATENT DOCUMENTS

| | | |
|---|---|---|
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015117025 A1 | 8/2015 |
| WO | WO-2015120122 A2 | 8/2015 |
| WO | WO-2015123607 A2 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017136596 A1 | 8/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-2019131148 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO 2019/195860 | 10/2019 |
| WO | WO-2019190800 A1 | 10/2019 |
| WO | WO-2019191102 A1 | 10/2019 |

OTHER PUBLICATIONS

International Search Report and Written Opinion for International Application No. PCT/US2019/051615, dated Mar. 2, 2020, 14 pages.

International Search Report and Written Opinion for International Application No. PCT/US2019/051957, dated Apr. 30, 2020, 16 pages.

Office Action for U.S. Appl. No. 16/155,890, dated Feb. 8, 2019, 13 pages.

Office Action for U.S. Appl. No. 16/448,108, dated Jan. 21, 2020, 14 pages.

Office Action for U.S. Appl. No. 16/448,108, dated Sep. 1, 2020, 14 pages.

Office Action for U.S. Appl. No. 16/455,417, dated Sep. 23, 2019, 11 pages.

International Search Report and Written Opinion for International Application No. PCT/US2019/067010, dated Mar. 10, 2020, 17 pages.

Office Action for U.S. Appl. No. 16/455,740, dated Jul. 24, 2020, 7 pages.

International Search Report and Written Opinion for International Application No. PCT/US2020/015231, dated Apr. 23, 2020, 10 pages.

(56) References Cited

OTHER PUBLICATIONS

International Search Report and Written Opinion for International Application No. PCT/US2020/021300, dated Oct. 7, 2020, 6 pages.
International Search Report and Written Opinion for International Application No. PCT/US2020/031390, dated Aug. 3, 2020, 10 pages.
International Search Report and Written Opinion for International Application No. PCT/US2020/013240, dated Jun. 3, 2020, 7 pages.
International Search Report and Written Opinion for International Application No. PCT/US2020/022828, dated May 19, 2020, 12 pages.
Office Action for U.S. Appl. No. 16/442,504, dated Jan. 14, 2020, 11 pages.
International Search Report and Written Opinion for International Application No. PCT/US2020/045195, dated Jan. 8, 2021, 18 pages.
International Search Report and Written Opinion for International Application No. PCT/US2020/047162, dated Dec. 30, 2020, 9 pages.
Office Action for U.S. Appl. No. 16/445,210, dated Jan. 28, 2021, 7 pages.
Office Action for U.S. Appl. No. 16/448,108, dated Mar. 8, 2021, 8 pages.
Office Action for U.S. Appl. No. 16/163,577, dated Mar. 8, 2021, 10 pages.
Office Action for U.S. Appl. No. 17/154,227, dated Mar. 29, 2021, 6 pages.
International Search Report and Written Opinion for International Application No. PCT/US2021/013570, dated Apr. 1, 2021, 9 pages.
International Search Report and Written Opinion for International Application No. PCT/US2019/028822, dated Oct. 24, 2019, 14 pages.
Office Action for U.S. Appl. No. 17/167,983, dated Apr. 13, 2021, 20 pages.
Office Action for U.S. Appl. No. 17/154,438, dated May 3, 2021, 16 pages.
Office Action for U.S. Appl. No. 17/193,936, dated May 27, 2021, 6 pages.
Office Action for U.S. Appl. No. 17/154,227, dated Jun. 18, 2021, 8 pages.
Office Action for U.S. Appl. No. 16/443,862, dated Nov. 12, 2021, 9 pages.
Office Action for U.S. Appl. No. 16/449,420, dated Sep. 1, 2021, 16 pages.
Office Action for U.S. Appl. No. 17/167,988, dated Sep. 22, 2021, 19 pages.
Office Action for U.S. Appl. No. 17/221,547, dated Aug. 4, 2021, 11 pages.
Office Action for U.S. Appl. No. 17/221,547, dated Oct. 21, 2021, 9 pages.
Office Action for U.S. Appl. No. 17/222,430, dated Oct. 7, 2021, 17 pages.
Office Action for U.S. Appl. No. 17/236,219, dated Aug. 4, 2021, 17 pages.

* cited by examiner

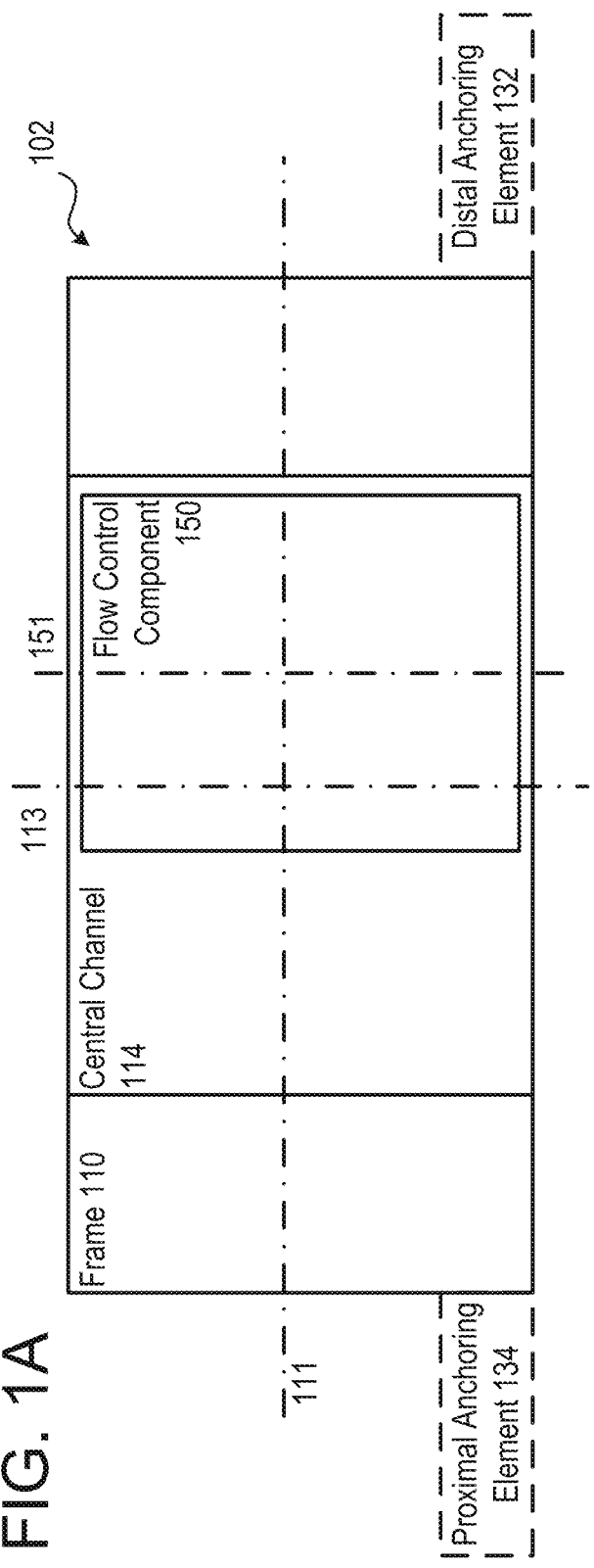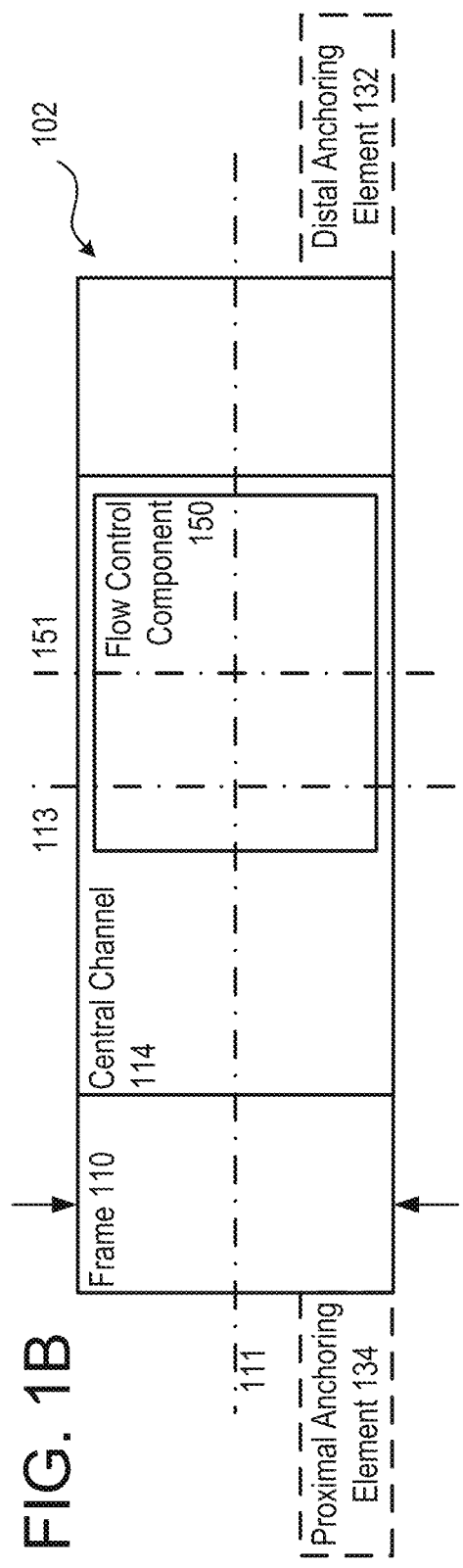

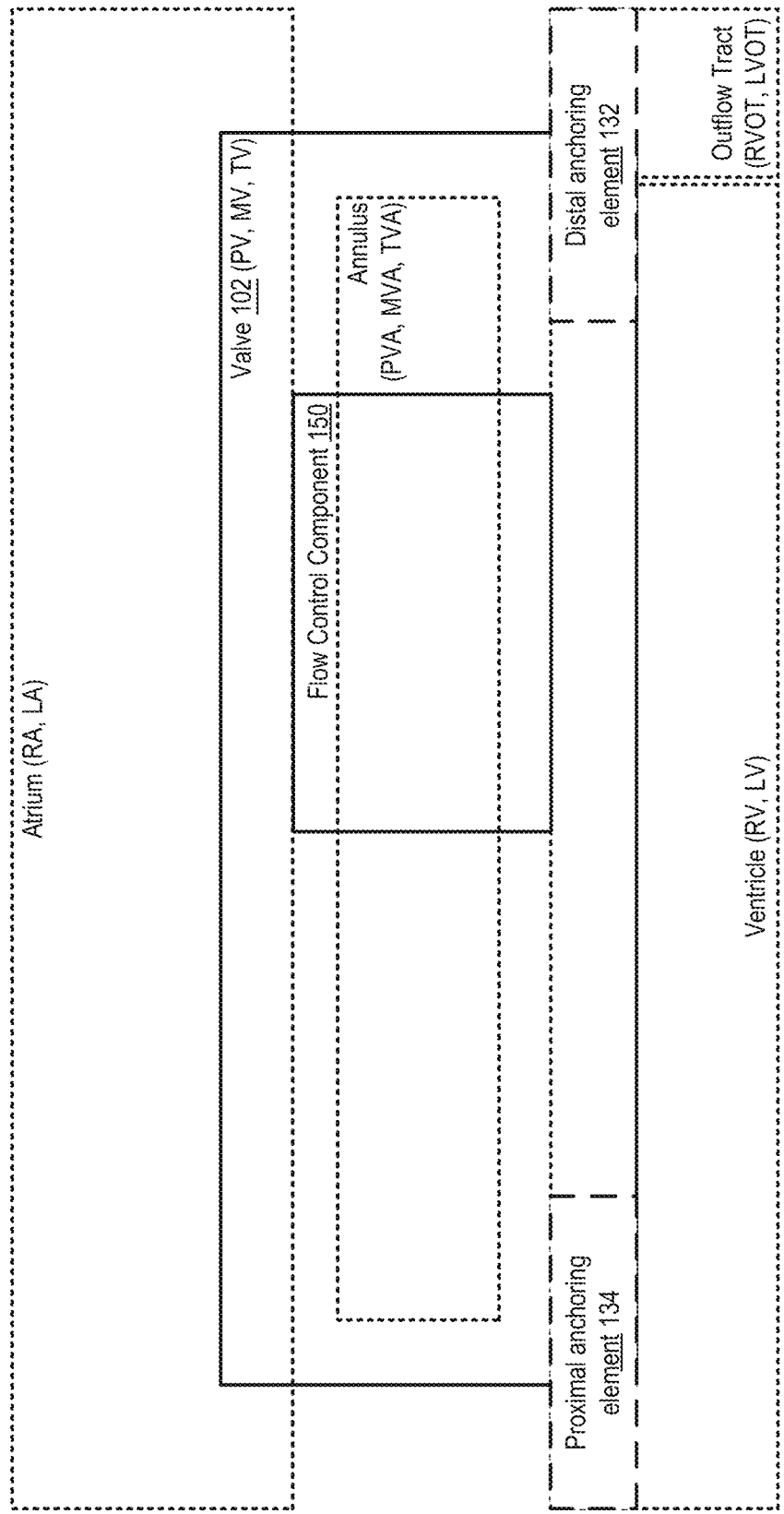

810

840

865  866
810

865  866
810

810

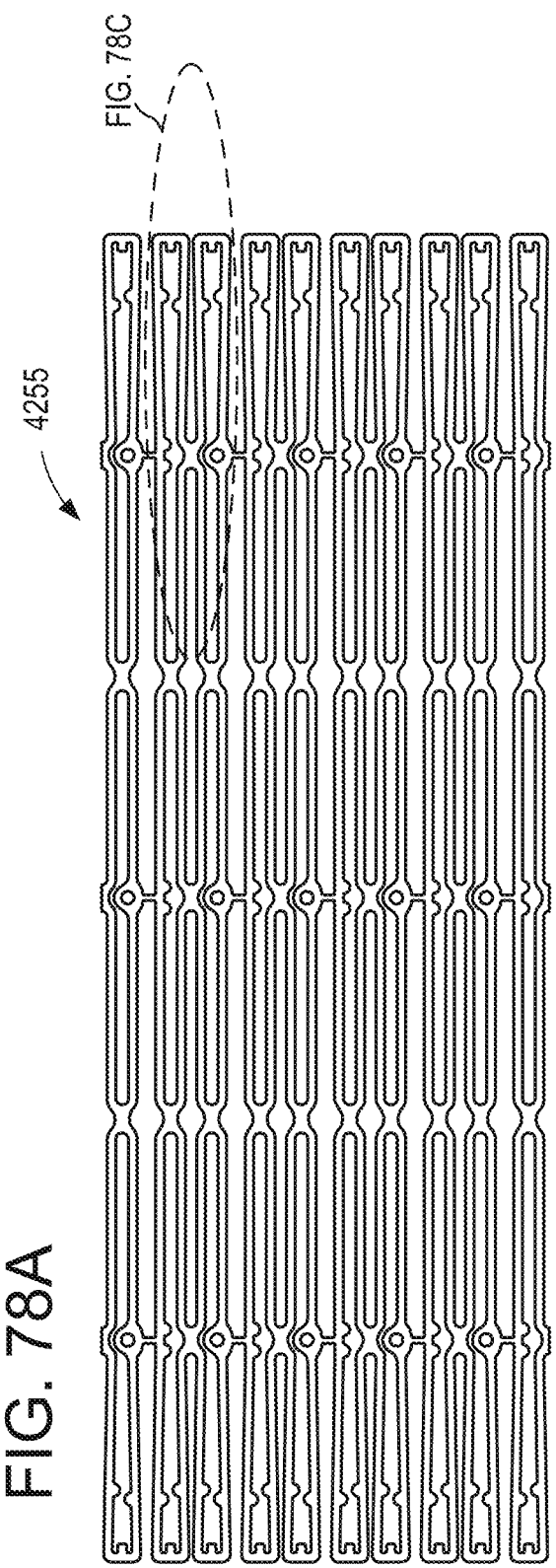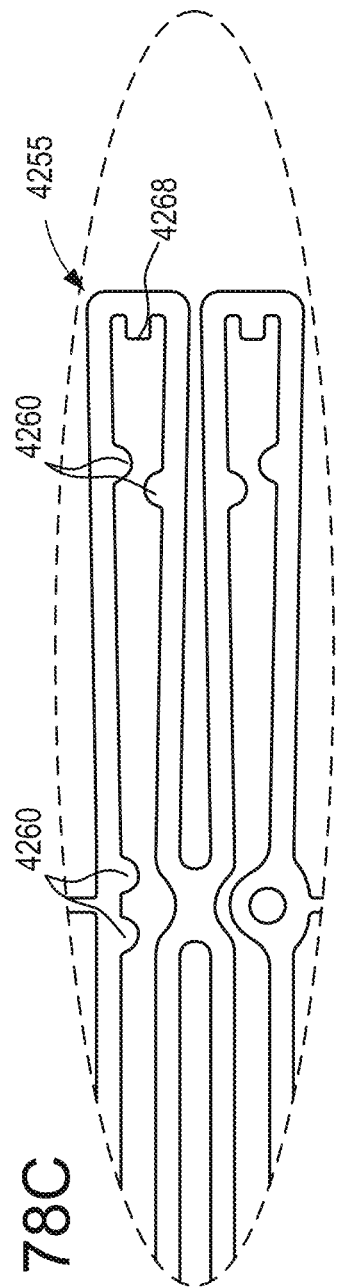

Fold a side-delivered prosthetic heart valve along a longitudinal axis such that an inner flow control component elastically deforms in response to the folding
11

↓

Compress the side-delivered prosthetic heart valve along a central axis of an outer frame to place the side-delivered prosthetic heart valve in a compressed configuration, wherein the central axis is orthogonal to the longitudinal axis
12

↓

Insert the side-delivered prosthetic heart valve into a lumen of a delivery catheter such that the longitudinal axis is substantially parallel to a lengthwise axis of the delivery catheter
13

COLLAPSIBLE INNER FLOW CONTROL COMPONENT FOR SIDE-DELIVERABLE TRANSCATHETER HEART VALVE PROSTHESIS

CROSS-REFERENCE TO RELATED APPLICATIONS

This application is a continuation of International Patent Application No. PCT/US2020/015231, entitled "Collapsible Inner Flow Control Component for Side-Deliverable Transcatheter Heart Valve Prosthesis," filed on Jan. 27, 2020, which is a continuation-in-part of U.S. patent application Ser. No. 16/455,740, entitled "Collapsible Inner Flow Control Component for Side-Delivered Transcatheter Heart Valve Prosthesis," filed on Jun. 27, 2019, which claims priority to and the benefit of U.S. Provisional Patent Application No. 62/797,201, entitled "Collapsible Inner Flow Control Component for Orthogonal Transcatheter Heart Valve Prosthesis," filed on Jan. 26, 2019. International Patent Application No. PCT/US2020/015231 also claims priority to and the benefit of U.S. Provisional Patent Application No. 62/797,201, entitled "Collapsible Inner Flow Control Component for Orthogonal Transcatheter Hear Valve Prosthesis,' filed on Jan. 26, 2019. This application is also a continuation-in-part of U.S. patent application Ser. No. 16/455,740 entitled "Collapsible Inner Flow Control Component for Side-Delivered Transcatheter Heart Valve Prosthesis," filed on Jun. 27, 2019. The disclosure of each of the foregoing applications is incorporated herein by reference in its entirety.

BACKGROUND

Embodiments are described herein that relate to transcatheter prosthetic heart valves and/or the inner flow control components thereof, and methods for the delivery and/or deployment of such prosthetic heart valves and/or inner flow control components.

Prosthetic heart valves can pose challenges for delivery and deployment within a heart, particularly for delivery by catheters through the patient's vasculature rather than through a surgical approach. Delivery of traditional transcatheter prosthetic valves generally includes compressing the valve in a radial direction and loading the valve into a delivery catheter such that a central annular axis of the valve is parallel to a lengthwise axis of the delivery catheter. The valves are deployed from the end of the delivery catheter and expanded outwardly in a radial direction from the central annular axis. The expanded size (e.g., diameter) of traditional valves, however, can be limited by the internal diameter of the delivery catheter. The competing interest of minimizing delivery catheter size presents challenges to increasing the expanded diameter of traditional valves (e.g., trying to compress too much material and structure into too little space).

Some transcatheter prosthetic valves can be configured for side and/or orthogonal delivery, which can have an increased expanded diameter relative to traditional valves. For example, in side and/or orthogonal delivery, the valve and/or valve frame is compressed and loaded into a delivery catheter such that a central annular axis of the valve and/or valve frame is substantially orthogonal to the lengthwise axis of the delivery catheter, which can allow the valve to be compressed laterally and extended longitudinally (e.g., in a direction parallel to the lengthwise axis of the delivery catheter). In such implementations, it is desirable to provide an inner flow control component that is compatible with the lateral compression and/or longitudinal extension experienced during delivery. Moreover, in some implementations, it is desirable to provide a prosthetic valve with an outer portion or frame that has a size and/or shape that corresponds to a size and/or shape of the annulus of the native valve while providing an inner flow control component that has a substantially cylindrical shape that allows for optimal function of the prosthetic valve leaflets included therein.

Accordingly, a need exists for prosthetic heart valves and/or the inner flow control components thereof, and methods for the delivery and/or deployment of such prosthetic heart valves and/or inner flow control components.

SUMMARY

The embodiments described herein relate generally to transcatheter prosthetic heart valves and/or the inner flow control components thereof, and methods for delivering and/or deploying the same. In some embodiments, a side-deliverable prosthetic heart valve includes an outer frame and a flow control component. The outer frame defines a central channel that extends along a central axis of the outer frame. The flow control component is disposed within the central channel and coupled to the outer frame. The flow control component has an inner frame and a set of leaflets coupled to the inner frame. The prosthetic valve is configured to be folded along a longitudinal axis and compressed along the central axis to place the prosthetic valve in a compressed configuration for delivery via a delivery catheter. The longitudinal axis is substantially parallel to a lengthwise axis of the delivery catheter when the prosthetic valve is disposed therein. The prosthetic valve is configured to transition to an expanded configuration when the prosthetic valve is released from the delivery catheter. The flow control component elastically deforms from a substantially cylindrical configuration to a substantially flattened configuration when the prosthetic valve is placed in the compressed configuration.

BRIEF DESCRIPTION OF THE DRAWINGS

FIGS. 1A and 1B are front view schematic illustrations of a side-delivered transcatheter prosthetic heart valve (also referred to herein as "prosthetic valve") according to an embodiment, and shown in an expanded configuration and a compressed configuration, respectively.

FIG. 1E is a schematic illustration of the prosthetic valve of FIGS. 1A-1D deployed within an annulus of a native heart valve.

FIGS. 78A and 78B are a top view illustration and a front view illustration, respectively, of a laser cut workpiece of a shape memory alloy material configured to be formed into an inner frame of a flow control component according to an embodiment.

FIG. 78C is an enlarged top view illustration of a portion of the laser cut workpiece identified by the circled region in FIG. 78A.

FIG. 112 is a flowchart illustrating a method of compressing a side-delivered prosthetic heart valve for transcatheter delivery to a desired location in the body according to an embodiment.

DETAILED DESCRIPTION

Figure 1C:
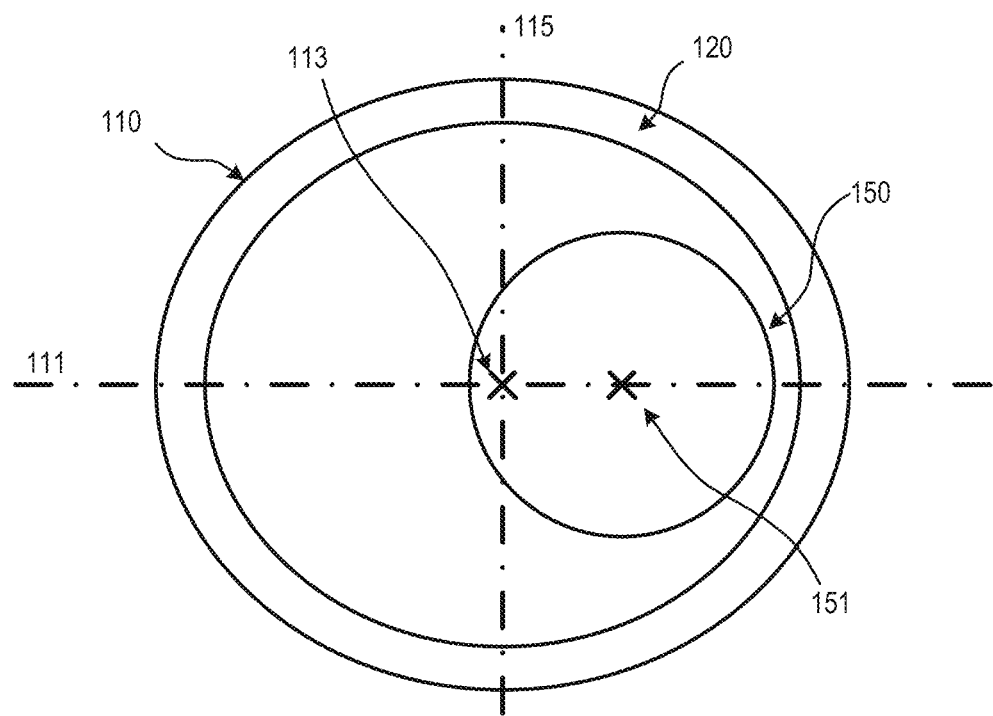
FIGS. 1C and 1D are top view schematic illustrations of the prosthetic valve of FIGS. 1A and 1B, and shown in the expanded configuration and the compressed configuration, respectively.

Disclosed embodiments are directed to transcatheter prosthetic heart valves and/or components thereof, and methods of manufacturing, loading, delivering, and/or deploying the transcatheter prosthetic valves and/or components thereof. In some embodiments, a side-deliverable prosthetic heart valve includes an outer frame and a flow control component. The outer frame defines a central channel that extends along a central axis of the outer frame. The flow control component is disposed within the central channel and coupled to the outer frame. The flow control component has an inner frame and a set of leaflets coupled to the inner frame. The prosthetic valve is configured to be folded along a longitudinal axis and compressed along the central axis to place the prosthetic valve in a compressed configuration for delivery via a delivery catheter. The longitudinal axis is substantially parallel to a lengthwise axis of the delivery catheter when the prosthetic valve is disposed therein. The prosthetic valve is configured to transition to an expanded configuration when the prosthetic valve is released from the delivery catheter. The flow control component elastically deforms from a substantially cylindrical configuration to a substantially flattened configuration when the prosthetic valve is placed in the compressed configuration.

In some embodiments, a side-deliverable prosthetic heart valve includes an outer frame and a flow control component. The outer frame defines a central channel that extends along a central axis of the outer frame. The flow control component has an inner frame and a set of leaflets coupled to the inner frame. The flow control component is configured to be disposed within the central channel and coupled to the outer frame such that an axis defined by the inner frame of the flow control component is offset from the central axis of the outer frame.

In some embodiments, a method for compressing a side-deliverable prosthetic heart valve for transcatheter delivery to a desired location in the body includes folding the side-deliverable prosthetic heart valve along a longitudinal axis. The side-deliverable prosthetic heart valve has an outer frame that defines a central channel and a flow control component disposed within the central channel and coupled to the outer frame. The flow control component has an inner frame and a plurality of leaflets coupled to the inner frame. The flow control component is configured to elastically deform from a first configuration in which a perimeter of the inner frame is substantially cylindrical to a second configuration in which a perimeter of the inner frame is substantially flattened in response to the folding. The side-deliverable prosthetic heart valve is compressed along a central axis of the outer frame to place the side-deliverable prosthetic heart valve in a compressed configuration. The central axis is orthogonal to the longitudinal axis and the central channel extends in the direction of the central axis. The side-deliverable prosthetic heart valve is inserted into a lumen of a delivery catheter such that the longitudinal axis of the side-deliverable prosthetic heart valve is substantially parallel to a lengthwise axis of the delivery catheter.

General Description

As described in detail herein, prosthetic heart valves can have a valve frame and a flow control component mounted within a central lumen or aperture of the valve frame. The flow control component can be configured to permit blood flow in a first direction through an inflow end of the valve and block blood flow in a second direction, opposite the first direction, through an outflow end of the valve. The valves can be compressible and expandable along a long-axis (e.g., a longitudinal axis) substantially parallel to a lengthwise cylindrical axis of a delivery catheter used to deliver the valves. The valves can be configured to transition between a compressed configuration for introduction into the body using the delivery catheter, and an expanded configuration for implanting at a desired location in the body.

Any of the prosthetic heart valves described herein can be a relatively low profile, side-deliverable implantable prosthetic heart valve. Any of the prosthetic heart valves can be transcatheter prosthetic heart valves configured to be delivered into a heart via a delivery catheter. The prosthetic heart valves can have at least an annular outer valve frame and an inner flow control component (e.g., a 2-leaflet or 3-leaflet valve, sleeve, and/or the like) mounted in the valve frame. In some embodiments, the prosthetic heart valves can be a single or a dual-tab prosthetic heart valve. For example, a prosthetic heart valve can include an outer frame that includes or is coupled to a distal anchoring element (e.g., a sub-annular distal anchoring tab or the like) configured to extend into a right or a left ventricular outflow tract (RVOT or LVOT, respectively). In some implementations, a prosthetic heart valve can include a distal anchoring element and a proximal anchoring element (e.g., a sub-annular proximal anchoring tab) configured to extend into the proximal sub-annular space, preferably between the anterior and the posterior leaflets of the heart.

Any of the prosthetic heart valves described herein can be configured to transition between an expanded configuration and a compressed configuration. For example, any of the embodiments described herein can be a balloon-inflated prosthetic heart valve, a self-expanding prosthetic heart valve, and/or the like.

Any of the prosthetic heart valves described herein can be compressible—into the compressed configuration—in a lengthwise or orthogonal direction relative to the central axis of the flow control component that can allow a large diameter valve (e.g., having a height of about 5-60 mm and a diameter of about 20-80 mm) to be delivered and deployed from the inferior vena cava directly into the annulus of a native mitral or tricuspid valve using, for example, a 24-36Fr delivery catheter and without delivery and deployment from the delivery catheter at an acute angle of approach.

Any of the prosthetic heart valves described herein can have a central axis that is co-axial or at least substantially parallel with blood flow direction through the valve. In some embodiments, the compressed configuration of the valve is orthogonal to the blood flow direction. In some embodiments, the compressed configuration of the valve is parallel to or aligned with the blood flow direction. In some embodiment, the valve can be compressed to the compressed configuration in two directions—orthogonal to the blood flow direction (e.g., laterally) and parallel to the blood flow direction (e.g., axially). In some embodiments, a long-axis or longitudinal axis is oriented at an intersecting angle of between 45-135 degrees to the first direction when in the compressed configuration and/or the expanded configuration.

Any of the prosthetic heart valves described herein can include an anchoring element extending from a distal side of a valve frame, which can be used, for example, as a Right Ventricular Outflow Tract ("RVOT") tab or a Left Ventricular Outflow Tract ("LVOT") tab. Any of the valves described herein can also include an anchoring element extending from a proximal sided of the valve frame, which can be used, for example, to anchor the valve to a proximal sub-annular space. The anchoring elements can include and/or can be formed from a wire loop or wire frame, an integrated frame section, and/or a stent, extending from about 10-40 mm away from the tubular frame.

Any of the prosthetic heart valves described herein can include (i) an upper anchoring element attached to a distal upper edge of the tubular frame, the upper anchoring element can include or be formed from a wire loop or wire frame extending from about 2-20 mm away from the tubular frame, and (ii) a lower anchoring element (e.g., used as a RVOT tab) extending from a distal side of the tubular frame, the lower anchoring element can include and/or can be formed from a wire loop or wire frame extending from about 10-40 mm away from the tubular frame.

Any of the prosthetic heart valves described herein can include a distal lower anchoring element configured to be positioned into the RVOT of the right ventricle and a proximal lower anchoring element configured to be positioned into a sub-annular position in contact with and/or adjacent to sub-annular tissue of the right ventricle. The transcatheter prosthetic heart valve can also include a distal upper anchoring element configured to be positioned into a supra-annular position in contact with and/or adjacent to supra-annular tissue of the right atrium. The distal upper anchoring element can provide a supra-annular downward force in the direction of the right ventricle and the distal and proximal lower anchoring elements can provide a sub-annular upward force in the direction of the right atrium.

Any of the prosthetic hear valves described herein can include an outer support frame comprised of a set of compressible wire cells having an orientation and cell geometry substantially orthogonal to the central axis to minimize wire cell strain when the outer support frame is in a compressed configuration, a rolled and compressed configuration, or a folded and compressed configuration.

In some embodiments, an outer support frame has a lower body portion and an upper collar portion. The lower body portion forms a shape such as a funnel, cylinder, flat cone, or circular hyperboloid when the outer support frame is in an expanded configuration. In some embodiments, the outer support frame is comprised of a wire, a braided wire, or a laser-cut wire frame, and is covered with a biocompatible material. The biocompatible material can be covered such that an inner surface is covered with pericardial tissue, an outer surface is covered with a woven synthetic polyester material, and/or both the inner surface is covered with pericardial tissue and the outer surface is covered with a woven synthetic polyester material.

In some embodiments, an outer support frame has a side profile of a flat cone shape having an outer diameter R of 40-80 mm, an inner diameter r of 20-60 mm, and a height of 5-60 mm. In some embodiments, an annular support frame has a side profile of an hourglass shape having a top diameter R1 of 40-80 mm, a bottom diameter R2 of 50-70 mm, an internal diameter r of 20-60 mm, and a height of 5-60 mm.

Any of the prosthetic heart valves described herein and/or any component, feature, and/or aspect thereof can be similar to and/or substantially the same as the prosthetic heart valves (or components, features, and/or aspects thereof) described in International Patent Application No. PCT/US2019/051957, entitled "Transcatheter Deliverable Prosthetic Heart Valves and Method of Delivery," filed Sep. 19, 2019 (referred to herein as "the '957 PCT") and/or International Patent Application No. PCT/US2019/067010, entitled "Transcatheter Deliverable Prosthetic Heart Valves and Methods of Delivery," filed Dec. 18, 2019 (referred to herein as "the '010 PCT"), the disclosures of which are incorporated herein by reference in their entireties.

Any of the prosthetic hear valves described herein can include an inner flow control component that has a leaflet frame with 2-4 flexible leaflets mounted thereon. The 2-4 leaflets are configured to permit blood flow in a first direction through an inflow end of the flow control component and block blood flow in a second direction, opposite the first direction, through an outflow end of the flow control component. The leaflet frame can include two or more panels of diamond-shaped or eye-shaped wire cells made from heat-set shape memory alloy material such as, for example, Nitinol. The leaflet frame can be configured to be foldable along a z-axis (e.g., a longitudinal axis) from a rounded or cylindrical configuration to aflattened cylinder configuration, and compressible along a vertical y-axis (e.g., a central axis) to a compressed configuration. In some implementations, the leaflet frame can include a pair of hinge areas, fold areas, connection points, etc. that can allow the leaflet frame to be folded flat along the z-axis prior to the leaflet frame being compressed along the vertical y-axis. The inner frame can be, for example, a single-piece structure with two or more living hinges (e.g., stress concentration riser and/or any suitable structure configured to allow for elastic/non-permanent deformation of the inner frame). In other implementations, the inner frame can be a two-piece structure where the hinge areas are formed using a secondary attachment method (e.g. sutures, fabrics, molded polymer components, etc.)

In some embodiments, the inner flow control component in an expanded configuration forms a shape such as a funnel, cylinder, flat cone, or circular hyperboloid. In some embodiments, the inner flow control component has a leaflet frame comprised of a wire, a braided wire, or a laser-cut wire. In some embodiments, a leaflet frame can have a side profile of a flat cone shape having an outer diameter R of 20-60 mm, an inner diameter r of 10-50 mm, where diameter R is great than diameter r, and a height of 5-60 mm.

Any method for manufacturing prosthetic heart valves described herein can include using additive or subtractive metal or metal-alloy manufacturing to produce a self-expanding outer support frame having a central channel and an outer perimeter wall circumscribing a central vertical axis. A collapsible flow control component is mounted within the outer support frame and configured to permit blood flow in a first direction through an inflow end of the valve and block blood flow in a second direction, opposite the first direction, through an outflow end of the valve. The flow control component has a leaflet frame with 2-4 flexible leaflets mounted. The leaflet frame can be formed using additive or subtractive metal or metal-allow manufacturing. The additive metal or metal-alloy manufacturing can be 3D printing, direct metal laser sintering (powder melt), and/or the like. The subtractive metal or metal-alloy manufacturing is photolithography, laser sintering/cutting, CNC machining, electrical discharge machining, and/or the like. In some embodiments, a process of manufacturing can further include mounting the flow control component within the outer support frame, and covering an outer surface of the outer support frame with a pericardium material or similar biocompatible material.

Any method for delivering prosthetic heart valves described herein can include orthogonal delivery of the prosthetic heart valve to a desired location in the body that includes (i) advancing a delivery catheter to the desired location in the body and (ii) delivering the prosthetic heart valve to the desired location in the body by releasing the valve from the delivery catheter. The valve is in a compressed configuration when in the delivery catheter and transitions to an expanded configuration when released from the delivery catheter.

Any method for delivering prosthetic heart valves described herein can include at least one of (i) compressing the valve along a central vertical axis to reduce a vertical dimension of the valve from top to bottom to place the valve in a compressed configuration, (ii) unilaterally rolling the valve into a compressed configuration from one side of the annular support frame, (iii) bilaterally rolling the valve into a compressed configuration from two opposing sides of the annular support frame, (iv) flattening the valve into two parallel panels that are substantially parallel to the long-axis, (v) flattening the valve into two parallel panels that are substantially parallel to the long-axis and then rolling the flattened valve into a compressed configuration, or (vi) flattening the valve into two parallel panels that are substantially parallel to the long-axis and then compressing the valve along a central vertical axis to reduce a vertical dimension of the valve from top to bottom to place the valve in a compressed configuration.

Any method for delivering prosthetic heart valves described herein can include attaching a pulling wire (e.g., a rigid elongated pulling/pushing rod or draw wire) to a sidewall or an anchoring element (e.g., a distal anchoring element) of the prosthetic heart valve and pulling the valve into and/or through a delivery catheter.

Any method for delivering prosthetic heart valves described herein can include releasing the valve from the delivery catheter by (i) pulling the valve out of the delivery catheter using a pulling wire or rod that is releasably connected to a sidewall or an anchoring element, wherein advancing the pulling wire away from the delivery catheter pulls the compressed valve out of the delivery catheter, or (ii) pushing the valve out of the delivery catheter using a pushing wire or rod that is releasably connected to a sidewall or an anchoring element, wherein advancing the pushing wire or rod out of from the delivery catheter pushes the compressed valve out of the delivery catheter.

Any method for delivering prosthetic heart valves described herein can include releasing the valve from a delivery catheter while increasing blood flow during deployment of the valve by (i) partially releasing the valve from the delivery catheter to establish blood flow around the partially released valve and blood flow through the flow control component; (ii) completely releasing the valve from the delivery catheter while maintaining attachment to the valve to transition to a state with increased blood flow through the flow control component and decreased blood flow around the valve; (iii) deploying the valve into a final mounted position in a native annulus to transition to a state with complete blood flow through the flow control component and minimal or no blood flow around the valve; and (iv) disconnecting and withdrawing a positioning catheter, pulling or pushing wire or rod, and/or the delivery catheter.

Any method for delivering prosthetic heart valves described herein can include orthogonal delivery of the prosthetic heart valve to a native annulus of a human heart that includes at least one of (i) advancing the delivery catheter to the tricuspid valve or pulmonary artery of the heart through the inferior vena cava (IVC) via the femoral vein, (ii) advancing to the tricuspid valve or pulmonary artery of the heart through the superior vena cava (SVC) via the jugular vein, or (iii) advancing to the mitral valve of the heart through a trans-atrial approach (e.g., fossa ovalis or lower), via the IVC-femoral or the SVC jugular approach; and (iv) delivering the prosthetic heart valve to the native annulus by releasing the valve from the delivery catheter.

Any method for delivering prosthetic heart valves described herein can positioning the distal anchoring tab of the heart valve prosthesis into a ventricular outflow tract of the left or right ventricle. In some embodiments, the method can further include positioning an upper distal anchoring tab into a supra-annular position, where the upper distal anchoring tab provides a supra-annular downward force in the direction of the ventricle and the distal anchoring tab (e.g., the lower distal anchoring tab) provides a sub-annular upward force in the direction of the atrium. In some embodiments, the method can further include anchoring one or more tissue anchors attached to the valve into native tissue.

Any method for delivering prosthetic heart valves described herein and/or any portion thereof can be similar to and/or substantially the same as one or more methods for delivering prosthetic heart valves (or portion(s) thereof) described in the '957 PCT and/or the '010 PCT.

The terminology used herein is for the purpose of describing particular embodiments only and is not intended to limit the full scope of the claims. As used herein, the singular forms "a", "an" and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," etc.). Similarly, the terms "comprises" and/or "comprising," when used in this specification, specify the presence of stated features, integers (or fractions thereof), steps, operations, elements, and/or components, but do not preclude the presence or addition of one or more other features, integers (or fractions thereof), steps, operations, elements, components, and/or groups thereof. As used in this document, the term "comprising" means "including, but not limited to."

As used herein the term "and/or" includes any and all combinations of one or more of the associated listed items. It should be understood that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All ranges disclosed herein also encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

The term "valve prosthesis," "prosthetic heart valve," and/or "prosthetic valve" can refer to a combination of a frame and a leaflet or flow control structure or component, and can encompass both complete replacement of an anatomical part (e.g., a new mechanical valve replaces a native valve), as well as medical devices that take the place of and/or assist, repair, or improve existing anatomical parts (e.g., the native valve is left in place).

The disclosed valves include a member (e.g., a frame) that can be seated within a native valve annulus and can be used as a mounting element for a leaflet structure, a flow control component, or a flexible reciprocating sleeve or sleevevalve. It may or may not include such a leaflet structure or flow control component, depending on the embodiment. Such members can be referred to herein as an "annular support frame," "tubular frame," "wire frame," "valve frame," "flange," "collar," and/or any other similar terms.

The term "flow control component" can refer in a non-limiting sense to a leaflet structure having 2-, 3-, 4-leaflets of flexible biocompatible material such a treated or untreated pericardium that is sewn or joined to a annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating." The flow control component is contemplated to include a wide variety of (bio)prosthetic artificial heart valves. Bioprosthetic pericardial valves can include bioprosthetic aortic valves, bioprosthetic mitral valves, bioprosthetic tricuspid valves, and bioprosthetic pulmonary valves.

Any of the disclosed valve embodiments may be delivered by a transcatheter approach. The term "transcatheter" is used to define the process of accessing, controlling, and/or delivering a medical device or instrument within the lumen of a catheter that is deployed into a heart chamber (or other desired location in the body), as well as an item that has been delivered or controlled by such as process. Transcatheter access is known to include cardiac access via the lumen of the femoral artery and/or vein, via the lumen of the brachial artery and/or vein, via lumen of the carotid artery, via the lumen of the jugular vein, via the intercostal (rib) and/or sub-xiphoid space, and/or the like. Moreover, transcatheter cardiac access can be via the inferior vena cava (IVC), superior vena cava (SVC), and/or via a trans-atrial (e.g., fossa ovalis or lower). Transcatheter can be synonymous with transluminal and is functionally related to the term "percutaneous" as it relates to delivery of heart valves. As used herein, the term "lumen" can refer to the inside of a cylinder or tube. The term "bore" can refer to the inner diameter of the lumen.

The mode of cardiac access can be based at least in part on "body channel" may be used to define a blood conduit or vessel within the body, the particular application of the disclosed embodiments of prosthetic valves determines the body channel at issue. An aortic valve replacement, for example, would be implanted in, or adjacent to, the aortic annulus. Likewise, a tricuspid or mitral valve replacement would be implanted at the tricuspid or mitral annulus. Certain features are particularly advantageous for one implantation site or the other. However, unless the combination is structurally impossible, or excluded by claim language, any of the valve embodiments described herein could be implanted in any body channel.

The term "expandable" as used herein may refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Any of the disclosed valve embodiments may be delivered via traditional transcatheter delivery techniques or via orthogonal delivery techniques. For example, traditional delivery of prosthetic valves can be such that a central cylinder axis of the valve is substantially parallel to a length-wise axis of the delivery catheter. Typically, the valves are compressed in a radial direction relative to the central cylinder axis and advanced through the lumen of the delivery catheter. The valves are deployed from the end of the delivery catheter and expanded outwardly in a radial direction from the central cylinder axis.

As used herein the terms "side-delivered," "side-delivery," "orthogonal delivery," "orthogonally delivered," and/or so forth can be used interchangeably to describe such a delivery method and/or a valve delivered using such a method. Orthogonal delivery of prosthetic valves can be such that the central cylinder axis of the valve is substantially orthogonal to the length-wise axis of the delivery catheter. With orthogonal delivery, the valves are compressed (or otherwise reduced in size) in a direction substantially parallel to the central cylinder axis and/or in a lateral direction relative to the central cylinder axis. As such, a length-wise axis (e.g., a longitudinal axis) of an orthogonally delivered valve is substantially parallel to the length-wise axis of the delivery catheter. In other words, an orthogonally delivered prosthetic valve is compressed and/or delivered at a roughly 90 degree angle compared to traditional processes of compressing and delivering transcatheter prosthetic valves. Moreover, prosthetic valves configured to be orthogonally delivered and the processes of delivering such valves are described in detail in the '957 PCT and/or the '010 PCT incorporated by reference hereinabove.

Mathematically, the term "orthogonal" refers to an intersecting angle of 90 degrees between two lines or planes. As used herein, the term "substantially orthogonal" refers to an intersecting angle of 90 degrees plus or minus a suitable tolerance. For example, "substantially orthogonal" can refer to an intersecting angle ranging from 75 to 105 degrees.

Any of the prosthetic valves and/or components thereof may be fabricated from any suitable biocompatible material or combination of materials. For example, an outer valve frame, an inner valve frame (e.g., of an inner flow control component), and/or components thereof may be fabricated from biocompatible metals, metal alloys, polymer coated metals, and/or the like. Suitable biocompatible metals and/or metal alloys can include stainless steel (e.g., 316 L stainless steel), cobalt chromium (Co—Cr) alloys, nickel-titanium alloys (e.g., Nitinol®), and/or the like. Moreover, any of the outer or inner frames described herein can be formed from superelastic or shape-memory alloys such as nickel-titanium alloys (e.g., Nitinol®). Suitable polymer coatings can include polyethylene vinyl acetate (PEVA), poly-butyl methacrylate (PBMA), translute Styrene Isoprene Butadiene (SIBS) copolymer, polylactic acid, polyester, polylactide, D-lactic polylactic acid (DLPLA), polylactic-co-glycolic acid (PLGA), and/or the like. Some such polymer coatings may form a suitable carrier matrix for drugs such as, for example, Sirolimus, Zotarolimus, Biolimus, Novolimus, Tacrolimus, Paclitaxel, Probucol, and/or the like.

Some biocompatible synthetic material(s) can include, for example, polyesters, polyurethanes, polytetrafluoroethylene (PTFE) (e.g., Teflon), and/or the like. Where a thin, durable synthetic material is contemplated (e.g., for a covering), synthetic polymer materials such expanded PTFE or polyester may optionally be used. Other suitable materials may optionally include elastomers, thermoplastics, polyurethanes, thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene (LDPE), high-density polyethylene (HDPE), ultra-high density polyethylene (UHDPE), polyolefins, polyethylene-glycols, polyethersulphones, polysulphones, polyvinylpyrrolidones, polyvinylchlorides, other fluoropolymers, polyesters, polyethylene-terephthalate (PET) (e.g., Dacron), Poly-L-lactic acids (PLLA), polyglycolic acid (PGA), poly(D, L-lactide/glycolide) copolymer (PDLA), silicone polyesters, polyamides (Nylon), PTFE, elongated PTFE, expanded PTFE, siloxane polymers and/or oligomers, and/or polylactones, and block co-polymers using the same.

Any of the outer valve frames, inner valve frames (e.g., of the flow control components), and/or portions or components thereof can be internally or externally covered, partially or completely, with a biocompatible material such as pericardium. A valve frame may also be optionally externally covered, partially or completely, with a second biocompatible material such as polyester or Dacron®. Disclosed embodiments may use tissue, such as a biological tissue that is a chemically stabilized pericardial tissue of an animal, such as a cow (bovine pericardium), sheep (ovine pericardium), pig (porcine pericardium), or horse (equine pericardium). Preferably, the tissue is bovine pericardial tissue. Examples of suitable tissue include that used in the products Dura-Guard®, Peri-Guard®, and Vascu-Guard®, all products currently used in surgical procedures, and which are marketed as being harvested generally from cattle less than 30 months old.

DRAWINGS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein. Rather, these embodiments are provided so that this disclosure will be thorough and complete, and will fully convey the scope of the inventive concepts to those skilled in the art. Like numbers refer to like elements throughout.

FIGS. 1A-1E are various schematic illustrations of a transcatheter prosthetic valve 102 according to an embodiment. The transcatheter prosthetic valve 102 is configured to be deployed in a desired location within a body (e.g., of a human patient) and to permit blood flow in a first direction through an inflow end of the transcatheter prosthetic valve 102 and to block blood flow in a second direction, opposite the first direction, through an outflow end of the transcatheter prosthetic valve 102. For example, the transcatheter prosthetic valve 102 can be a transcatheter prosthetic heart valve configured to be deployed within the annulus of a native tricuspid valve or native mitral valve of a human heart to supplement and/or replace the functioning of the native valve.

The transcatheter prosthetic valve 102 (also referred to herein as "prosthetic valve" or simply "valve") is compressible and expandable in at least one direction relative to a long-axis 111 of the valve 102 (also referred to herein as "horizontal axis," "longitudinal axis," or "lengthwise axis"). The valve 102 is configured to compressible and expandable between an expanded configuration (FIGS. 1A, 1C, and 1E) for implanting at a desired location in a body (e.g., a human heart) and a compressed configuration (FIGS. 1B and 1D) for introduction into the body using a delivery catheter 172.

In some embodiments, the valve 102 can be centric, or radially symmetrical. In other embodiments, the valve 102 can be eccentric, or radially (y-axis) asymmetrical. In some eccentric embodiments, the valve 102 (or an outer frame thereof) may have a D-shape (viewed from the top) so the flat portion can be matched to the anatomy in which the valve 102 will be deployed. For example, in some instances, the valve 102 may be deployed in the tricuspid annulus and may have a complex shape determined by the anatomical structures where the valve 102 is being mounted. In the tricuspid annulus, the circumference of the tricuspid valve may be a rounded ellipse, the septal wall is known to be substantially vertical, and the tricuspid is known to enlarge in disease states along the anterior-posterior line. In other instances, the valve 102 may be deployed in the mitral annulus (e.g., near the anterior leaflet) and may have a complex shape determined by the anatomical structures where the valve 102 is being mounted. For example, in the mitral annulus, the circumference of the mitral valve may be a rounded ellipse, the septal wall is known to be substantially vertical, and the mitral is known to enlarge in disease states.

In some embodiments, the valve 102 (and/or at least a portion thereof) may start in a roughly tubular configuration, and be heat-shaped to provide an upper atrial cuff or flange for atrial sealing and a lower transannular tubular or cylindrical section having an hourglass cross-section for about 60-80% of the circumference to conform to the native annulus along the posterior and anterior annular segments while remaining substantially vertically flat along 20-40% of the annular circumference to conform to the septal annular segment. While the valve 102 is shown in FIGS. 1A-1E as having a given shape, it should be understood that the size and/or shape of the valve 102 (and/or at least a portion thereof) can be based on a size and/or shape of the anatomical structures of the native tissue.

As shown, the valve 102 generally includes an annular support frame 110 and a flow control component 150. In addition, the valve 102 and/or at least the annular support frame 110 of the valve 102 optionally can include one or more anchoring element. For example, in the embodiment shown in FIGS. 1A-1E, the annular support frame 110 optionally includes at least a distal anchoring element 132 and a proximal anchoring element 134. In some implementations, the distal anchoring element 132 and the proximal anchoring element 134 can be lower anchoring elements and the valve 102 and/or the annular support frame 110 can include a distal upper anchoring element and a proximal upper anchoring element (not shown). In some implementations, the valve 102 and/or aspects or portions thereof can be similar to and/or substantially the same as the valves (and/or the corresponding aspects or portions thereof) described in detail in the '957 PCT and/or the '010 PCT incorporated by reference hereinabove. Accordingly, certain aspects, portions, and/or details of the valve 102 may not be described in further detail herein.

The annular support frame 110 (also referred to herein as "tubular frame," "valve frame," "wire frame," "outer frame," or "fame") can have or can define an aperture or central channel 114 that extends along a central axis 113. The central channel 114 (e.g., a central axial lumen or channel) can be sized and configured to receive the flow control component 150 across a portion of a diameter of the central channel 114. The frame 110 may have an outer circumferential surface for engaging native annular tissue that may be tensioned against an inner aspect of the native annulus to provide structural patency to a weakened native annular ring.

The frame 110 includes a cuff or collar (not shown) and a tubular, transannular, and/or body section (not shown). The cuff or collar (referred to herein as "collar") can be attached to and/or can form an upper edge of the frame 110. When the valve 102 is deployed within a human heart, the collar can be an atrial collar. The collar can be shaped to conform to the native deployment location. In a mitral valve replacement, for example, the collar will be configured with varying portions to conform to the native valve and/or a portion of the atrial floor surrounding the mitral valve. In one embodiment, the collar will have a distal and proximal upper collar portion. The distal collar portion can be larger than the proximal upper collar portion to account for annular geometries, supra-annular geometries, and/or subannular geometries. Examples of collars are described below with reference to specific embodiments.

The frame 110 may optionally have a separate atrial collar attached to the upper (atrial) edge of the frame 110, for deploying on the atrial floor that is used to direct blood from the atrium into the flow control component 150 and to seal against blood leakage (perivalvular leakage) around the frame 110. The frame 110 may also optionally have a separate ventricular collar attached to the lower (ventricular) edge of the frame 110, for deploying in the ventricle immediately below the native annulus that is used to prevent regurgitant leakage during systole, to prevent dislodging of the valve 102 during systole, to sandwich or compress the native annulus or adjacent tissue against the atrial cuff or collar, and/or optionally to attach to and support the flow control component 150. Some embodiments may have both an atrial collar and a ventricular collar, whereas other embodiments either include a single atrial collar, a single ventricular collar, or have no additional collar structure.

The frame 110 and/or at least the transannular or body section thereof can be a ring, or cylindrical or conical tube. In some embodiments, the frame 110 and/or at least the transannular or body section thereof may have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. The frame 110 may have a height in the range of about 5-60 mm, may have an outer diameter dimension, R, in the range of about 20-80 mm, and may have an inner diameter dimension in the range of about 21-79 mm, accounting for the thickness of the frame 110 (e.g., a wire material forming the frame 110).

The frame 110 is compressible for delivery and when released it is configured to return to its original (uncompressed) shape. The frame 110 may be compressed for transcatheter delivery and may be expandable using a transcatheter expansion balloon. In other implementations, the frame 110 can include and/or can be formed of a shape-memory element allowing the frame 110 to be self-expanding. In some instances, suitable shape-memory materials can include metals and/or plastics that are durable and biocompatible. For example, the frame 110 can be made from superelastic metal wire, such as a Nitinol wire or other similarly functioning material. In some embodiments, the frame 110 can be formed from stainless steel, cobalt-chromium, titanium, and/or other functionally equivalent metals and/or alloys.

The frame 110 may be constructed as a wire, a braided wire, or a laser cut wire frame. In some embodiments, the frame 110 can include and/or can form a set of compressible wire cells having an orientation and cell geometry substantially orthogonal to the central vertical axis 113 to minimize wire cell strain when the frame 110 is in a vertical compressed configuration, a rolled and compressed configuration, or a folded and compressed configuration.

The frame 110 may also have and/or form additional functional elements (e.g., loops, anchors, etc.) for attaching accessory components such as biocompatible covers, tissue anchors, releasable deployment and retrieval control guides, knobs, attachments, rigging, and so forth. The frame 110 may be optionally internally or externally covered, partially or completely, with a biocompatible material such as pericardium, polyester, Dacron®, and/or the like. In some implementations, the frame 110 (or aspects and/or portions thereof) can be structurally and/or functionally similar to the frames (or corresponding aspects and/or portions thereof) described in detail in the '957 PCT and/or the '010 PCT.

As described above, the frame 110 and/or the valve 102 can include at least a distal anchoring element 132 and a proximal anchoring element 134. The anchoring elements of the valve 102 and/or the frame 110 can be any suitable shape, size, and/or configuration such as any of those described in detail in the '957 PCT and/or the '010 PCT, and/or any of those described herein with respect to specific embodiments. For example, the distal and proximal anchoring elements 132 and 134 can be, for example, lower anchoring elements (e.g., coupled to and/or included in a lower portion of the frame 110). In some embodiments, the frame 110 and/or the valve 102 can also optionally include one or more of a distal upper anchoring element and a proximal upper anchoring element. The anchoring elements of the frame 110 can include and/or can be formed from a wire loop or wire frame, an integrated frame section, and/or a stent, extending about 10-40 mm away from the frame 110.

The anchoring elements of the valve 102 can be configured to engage a desired portion of the annular tissue to mount the frame 110 to the annulus of the native valve in which the valve 102 is deployed. For example, the distal anchoring element 132 can extend from a lower distal side of the frame 110 and can act, for example, as a Right Ventricular Outflow Tract ("RVOT") anchor or a Left Ventricular Outflow Tract ("LVOT") anchor. The proximal anchoring element 134 can be, for example, a proximal lower anchoring element and can be configured to engage subannular tissue of the ventricle to aid in the securement of the valve 102 in the annulus. In some implementations, at least the proximal anchoring element 134 can be configured to transition between a first configuration in which the proximal anchoring element 134 is maintained in a compressed, undeployed, and/or restrained state, to a second configuration in which the proximal anchoring element 134 is expanded, extended, deployed, and/or unrestrained, which can aid in the deployment of the valve 102 in the native annulus, as described in detail in the '010 PCT.

In some embodiments, the frame 110 can include a guidewire collar (not shown) configured to selectively engage and/or receive a portion of a guidewire or a portion of a guidewire assembly and/or can have any suitable configuration. In certain embodiments, the distal lower anchoring element 132 can form and/or can include a feature that forms the guidewire collar. In other implementations, the guidewire collar can be attached to any suitable portion of the frame 110, to the proximal anchoring element 134, and/or to any other anchoring elements and/or features of the frame 110 (e.g., a distal or proximal upper anchoring element). In some embodiments, the guidewire collar is configured to allow a portion of the guidewire to extend through an aperture of the guidewire, thereby allowing the valve 102 to be advanced over or along the guidewire. In some embodiments, the guidewire collar can selectively allow the guidewire to be advanced therethrough while blocking or preventing other elements and/or components such as a pusher or the like.

The flow control component 150 can refer in a non-limiting sense to a device for controlling fluid flow therethrough. In some embodiments, the flow control component 150 can be a leaflet structure having 2-leaflets, 3-leaflets, 4-leaflets, or more, made of flexible biocompatible material such a treated or untreated pericardium. The leaflets can be sewn or joined to a support structure such as an inner frame, which in turn, can be sewn or joined to the outer frame 110.

Figure 1D:
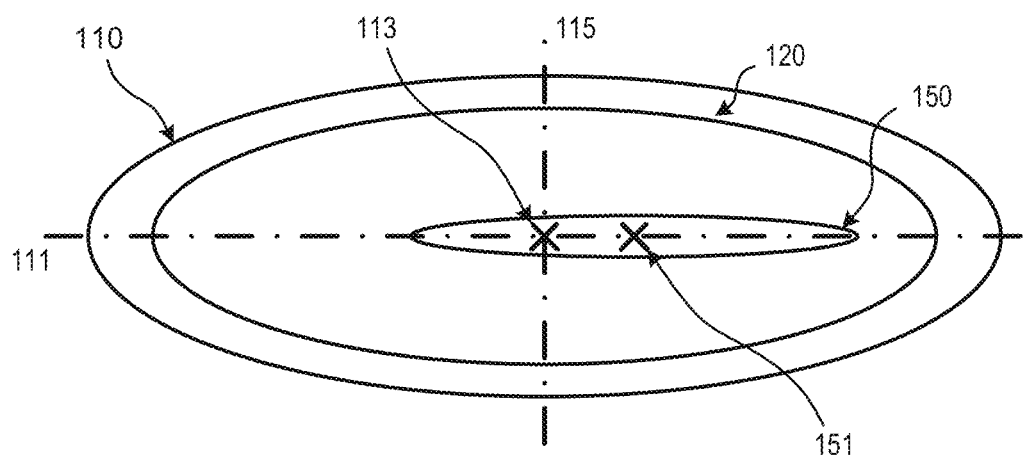

In some embodiments, the flow control component 150 and/or the inner frame thereof can have a substantially cylindrical or tubular shape when the valve 102 is in the expanded configuration (see e.g., FIG. 1C) and can be configured to elastically deform when the valve 102 is placed in the compressed configuration (see e.g., FIGS. 1B and 1D). The inner frame and/or portions or aspects thereof can be similar in at least form and/or function to the outer frame 110 and/or portions or aspects thereof. For example, the inner frame can be compressible for delivery and when released it is configured to return to its original (uncompressed) shape. The inner frame can be formed of a shape-memory element allowing the inner frame to be self-expanding. In some instances, suitable shape-memory materials can include metals and/or plastics that are durable and biocompatible such as, for example, Nitinol.

In some embodiments, an amount of non-elastic (e.g., permanent) deformation can be maintained below a deformation threshold. For example, in some embodiments, the inner frame can be deformed such that a maximum strain during folding and/or compression is about 6% or less. In some implementations, a deformation threshold can be an amount of difference between major and minor axes of the cylindrical frame post-delivery (e.g., less than about 5% difference). In some implementations, an amount of deflection of one or more portions of the inner frame is less than about 5%. On the other hand, the inner frame can be sufficiently stiff to reduce and/or substantially minimize commissure motion in a vertical direction under pulsatile loads (e.g., associated with the opening and closing of the leaflets). In general, the vertical motion (deflection) at the commissures under hemodynamic pressures (e.g., maximum hemodynamic pressures) can be less than about 5% of the overall valve height. In some implementations, the frame can provide sufficient radial stiffness to limit a radial motion of the commissures. In general, the radial motion (deflection) at the commissures under hemodynamic pressures can be less than about 5% of the diameter of the inner frame.

The inner frame may be constructed as a wire, a braided wire, or a laser cut wire frame. In some embodiments, the inner frame can include and/or can form a set of compressible wire cells having an orientation and cell geometry substantially orthogonal to an axis 151 of the flow control component 150 to minimize wire cell strain when the inner frame is in a compressed configuration. For example, in some embodiments, the inner frame can have any suitable number of elastically deformable diamond-shaped or eye-shaped wire cells, and/or the like. Although not shown in FIGS. 1A-1E, in some embodiments, the inner frame can include and/or can be formed with two halves that can be coupled together to allow the inner frame to elastically deform in response to lateral compression or folding along or in a direction of a lateral axis 115, as described in further detail herein.

The flow control component 150 can be mounted within the frame 110 and configured to permit blood flow in a first direction through an inflow end of the valve and block blood flow in a second direction, opposite the first direction, through an outflow end of the valve. For example, the flow control component 150 can be configured such that the valve 102 functions, for example, as a heart valve, such as a tricuspid valve, mitral valve, aortic valve, or pulmonary valve, that can open to blood flowing during diastole from atrium to ventricle, and that can close from systolic ventricular pressure applied to the outer surface. Repeated opening and closing in sequence can be described as "reciprocating."

As shown in FIGS. 1A-1D, the flow control component 150 is mounted within the central channel 114 of the frame 110. More specifically, the flow control component 150 can be mounted within the central channel 114 such that the axis 151 of the flow control component 150 that extends in the direction of blood flow through the flow control component 150 is substantially parallel to and offset from the central axis 113 of the frame 110. That is to say, the flow control component 150 is disposed in an off-center position within the central channel 114. In some embodiments, for example, the central channel 114 can have a diameter and/or perimeter that is larger than a diameter and/or perimeter of the flow control component 150. Although not shown in FIGS. 1A-1E, in some embodiments, the valve 102 can include a spacer or the like that can be disposed within the central channel 114 adjacent to the flow control component 150. In other embodiments, a spacer can be a cover or the like coupled to a portion of the frame 110 and configured to cover a portion of the central channel 114. In some instances, the spacer can be used to facilitate the coupling of the flow control component 150 to the frame 110.

In some embodiments, the coupling of the flow control component 150 to the frame 110 (e.g., to a drum, collar portion, transannular section, and/or the like) can include coupling the flow control component 150 to a collar of the frame 110 via tissue or a biocompatible mesh or the like; coupling the flow control component 150 to a collar of the frame 110 via tissue or a biocompatible mesh or the like and one or more superelastic or shape-memory alloy structures; coupling the flow control component 150 to a collar of the frame 110 via tissue or a biocompatible mesh or the like and one or more superelastic or shape-memory alloy structures that is integrated into the atrial collar; coupling the flow control component 150 to a collar of the frame 110 via tissue, biocompatible mesh, or the like and one or more woven or knitted fabrics; coupling the flow control component 150 to a collar of the frame 110 via tissue, biocompatible mesh, or the like, which is sutured and/or sewn into place; coupling the flow control component 150 to a collar of the frame 110 via tissue, biocompatible mesh, or the like with a structural and/or fabric cross member that can be folded in the fold direction; and/or any other suitable coupling method.

As described above, the valve 102 is compressible and expandable between the expanded configuration and the compressed configuration. The valve 102 can have a first height or size along the central axis 113 when in the expanded configuration and can have a second height or size, less than the first height or size, along the central axis 113 when in the compressed configuration. The valve 102 can also be compressed in additional directions. For example, the valve 102 can be compressed along the lateral axis 115 that is perpendicular to both the longitudinal axis 111 and the central axis 113.

The valve 102 is compressed during delivery of the valve 102 and is configured to expand once released from the delivery catheter. More specifically, the valve 102 is configured for transcatheter orthogonal delivery to the desired location in the body (e.g., the annulus of a native valve), in which the valve 102 is compressed in an orthogonal or lateral direction relative to the dimensions of the valve 102 in the expanded configuration (e.g., along the central axis 113 and/or the lateral axis 115). During delivery, the longitudinal axis 111 of the valve 102 is substantially parallel to a longitudinal axis of the delivery catheter. In orthogonal delivery, the longitudinal axis 111 is oriented at an intersecting angle between 45 and 135 degrees relative to the central axis 113 (e.g., perpendicular or at about 90 degrees) and is in a substantially parallel orientation relative to a lengthwise cylindrical axis of the delivery catheter.

The valve 102 is in the expanded configuration prior to being loaded into the delivery catheter and/or after being released from the delivery catheter and deployed or implanted (or ready to be deployed or implanted) at the desired location in the body. The shape of the expanded valve 102 can be that of a large diameter shortened cylinder with an extended collar (e.g., the collar). When in the expanded configuration shown in FIGS. 1A, 1C, and 1E, the valve 102 has an extent in any direction orthogonal or lateral to the longitudinal axis 111 (e.g., along the central axis 113 and/or the lateral axis 115) that is larger than a diameter of the lumen of the delivery catheter used to deliver the valve 102. For example, in some embodiments, the valve 102 can have an expanded height (e.g., along the central axis 113) of 5-60 mm. In certain embodiments, the valve 102 can have an expanded height including, for example, 5 mm, 10 mm, 15 mm, 20 mm, 25 mm, 30 mm, 35 mm, 40 mm, 45 mm, 50 mm, 55 mm, and 60 mm, and/or any size or fraction of a size therebetween. In some embodiments, the valve 102 can have an expanded diameter length (e.g., along the longitudinal axis 111) and width (e.g., along the lateral axis 115) of about 20-80 mm, or about 40-80 mm. In certain embodiments, the valve 102 can have an expanded length and/or width including, for example, 20 mm, 25 mm, 30 mm, 35 mm, 40 mm, 45 mm, 50 mm, 55 mm, 60 mm, 65 mm, 70 mm, 75 mm, and 80 mm, and/or any size or fraction of a size therebetween.

When in the compressed configuration shown in FIGS. 1B and 1D, the valve 102 has an extent in any direction orthogonal or lateral to the longitudinal axis 111 (e.g., along the central axis 113 and/or the lateral axis 115) that is smaller than the diameter of the lumen of the delivery catheter, allowing the valve 102 to be delivered therethrough. For example, in some embodiments, the valve 102 can have a compressed height (e.g., along the central axis 113) and a compressed width (e.g., along the lateral axis 115) of about 6-15 mm, about 8-12 mm, or about 9-10 mm. In certain embodiments, the valve 102 can have a compressed height and/or width including, for example, 6 mm, 7 mm, 8 mm, 9 mm, 10 mm, 11 mm, 12 mm, 13 mm, 14 mm, and 15 mm, and/or any size or faction of a size therebetween. The valve 102 can be compressed by compressing, rolling, folding, and/or any other suitable manner, or combinations thereof, as described in detail in the '957 PCT and/or '010 PCT. It is contemplated in some embodiments that the length of the valve 102 (e.g., along the longitudinal axis 111) is not compressed for delivery. Rather, in some embodiments, the length of the 102 can be increased in response to compression of the valve 102 along the central axis 113 and the lateral axis 115.

Although not shown in FIGS. 1A-1E, in some implementations, a delivery system can include one or more features or components configured to deliver the valve 102 to a desired location in the body (e.g., the annulus of a native valve). For example, a delivery system can include the delivery catheter, a secondary catheter, and the guidewire. The delivery system can be configured to orthogonally deliver the compressed valve 102 and/or portions of the valve 102 (e.g., the compressed frame 110 or the compressed flow control component 150) to a desired location in the body such as, for example, the annulus of a native tricuspid valve and/or the annulus of a native mitral valve of the human heart. For example, the delivery catheter can be 12-34 Fr, with any suitable corresponding internal lumen diameter and/or an internal lumen diameter sufficient to receive the prosthetic valve 102 in the compressed configuration. In some implementations, the delivery system and/or aspects or portions thereof can be substantially similar in at least form, function, and/or operation as those described in detail in the '957 PCT and/or the '010 PCT and thus, is not described in further detail herein.

As shown in FIG. 1E, the valve 102 can be delivered, for example, to an atrium of the human heart and disposed within an annulus of a native valve such as, for example, the pulmonary valve (PV), the mitral valve (MV), the aortic valve (AV), and/or the tricuspid valve (TV). As described above, the valve 102 can be in the compressed configuration and delivered to the annulus via the delivery system and can be released from the delivery system and allowed to expand to the expanded configuration. For example, the valve 102 can be delivered to the atrium of the human heart and released from the delivery catheter (not shown) via any of the delivery systems, devices, and/or methods described in detail in the '957 PCT and/or the '010 PCT.

The deployment of the valve 102 can include placing the distal anchoring element 132 (e.g., the distal lower anchoring element 132) in the ventricle (RV, LV) below the annulus while the remaining portions of the valve 102 are in the atrium (RA, LA). In some instances, the distal anchoring element 132 can be positioned in an outflow tract of the ventricle (e.g., the distal anchoring element 132 can be advanced over and/or along the guidewire). For example, in some implementations, the valve 102 can be delivered to the annulus of the native tricuspid valve (TV) and at least a portion of the distal anchoring element 132 can be positioned in a right ventricular outflow tract (RVOT). In other implementations, the valve 102 can be delivered to the annulus of the native mitral valve (MV) and at least a portion of the distal anchoring element 132 can be positioned in a left ventricular outflow tract (LVOT). In some instances, the distal anchoring element 134 can engage subannular tissue to at least partially secure the distal end portion of the valve 102 to the native annular tissue while the remainder of the valve 102 is maintained in a supra-annular position within the atrium side of the annulus.

In some implementations, the prosthetic valve 102 can be temporarily maintained in a partially deployed state. For example, the valve 102 can be partially inserted into the annulus and held at an angle relative to the annulus to allow blood to flow from the atrium to the ventricle partially through the native valve annulus around the valve 102, and partially through the valve 102, which can allow for assessment of the valve function.

The valve 102 can be placed or seated in the annulus (PVA, MVA, AVA, and/or TVA) of the native valve (PV, MV, AV, and/or TV) such that the transannular section of the valve frame 110 extends through the annulus and into the ventricle while the collar remains in the atrium in a supra-annular position. For example, in some embodiments, the secondary catheter and/or the pusher (not shown) can be used to push at least the proximal end portion of the valve 102 into the annulus. In some implementations, the proximal anchoring element 134 can be maintained in its first configuration as the valve 102 is seated in the annulus. For example, as described above, the proximal anchoring element 134 can be in contact with, adjacent to, and/or near the transannular section of the frame 110 while in the first configuration, which in turn, can limit an overall circumference of a lower portion of the frame 110, thereby allowing the transannular section of the frame 110 to be inserted through the annulus.

Once seated, the proximal anchoring element 134 can be transitioned from its first configuration to its second configuration, as described in detail in the '010 PCT. Accordingly, once the valve 102 is seated in the annulus, the proximal anchoring element 134 can be placed in its second configuration in which the proximal anchoring element 134 contacts, engages, and/or is otherwise disposed adjacent to subannular tissue. Moreover, in some implementations, the distal anchoring element 132, the proximal anchoring element 134, and the collar (or any other upper anchoring elements) can exert a compressive force on the annular tissue separating the atrium from the ventricle, thereby placing the valve 102 in a fully deployed state. While not shown in FIGS. 1A-1E, in some implementations, the valve 102 and/or the delivery system can include one or more tissue anchors that can be used to anchor one or more portions of the valve 102 to the annular tissue, as described in detail in the '957 PCT.

Provided below is a discussion of certain aspects or embodiments of transcatheter prosthetic valves (e.g., prosthetic heart valves). The transcatheter prosthetic valves (or aspects or portions thereof) described below with respect to specific embodiments can be substantially similar in at least form and/or function to the valve 102 and/or corresponding aspects or portions of the valve 102 described above with reference to FIGS. 1A-1E. Similarly, the valves described below (or aspects or portions thereof) can be similar in at least form and/or function to the valves described in detail in the '957 PCT and/or the '010 PCT. Thus, certain aspects and/or portions of the specific embodiments may not described in further detail herein.

Figure 2:
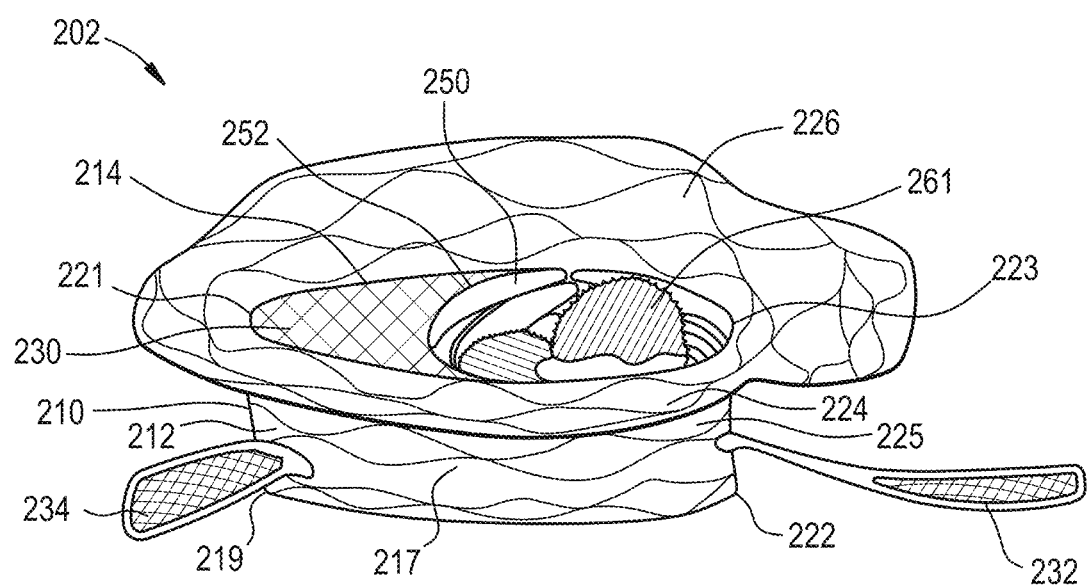
FIG. 2 is a side perspective view illustration of a prosthetic valve according to an embodiment.
Figure 2:
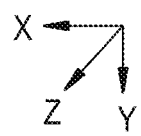
Figure 3:
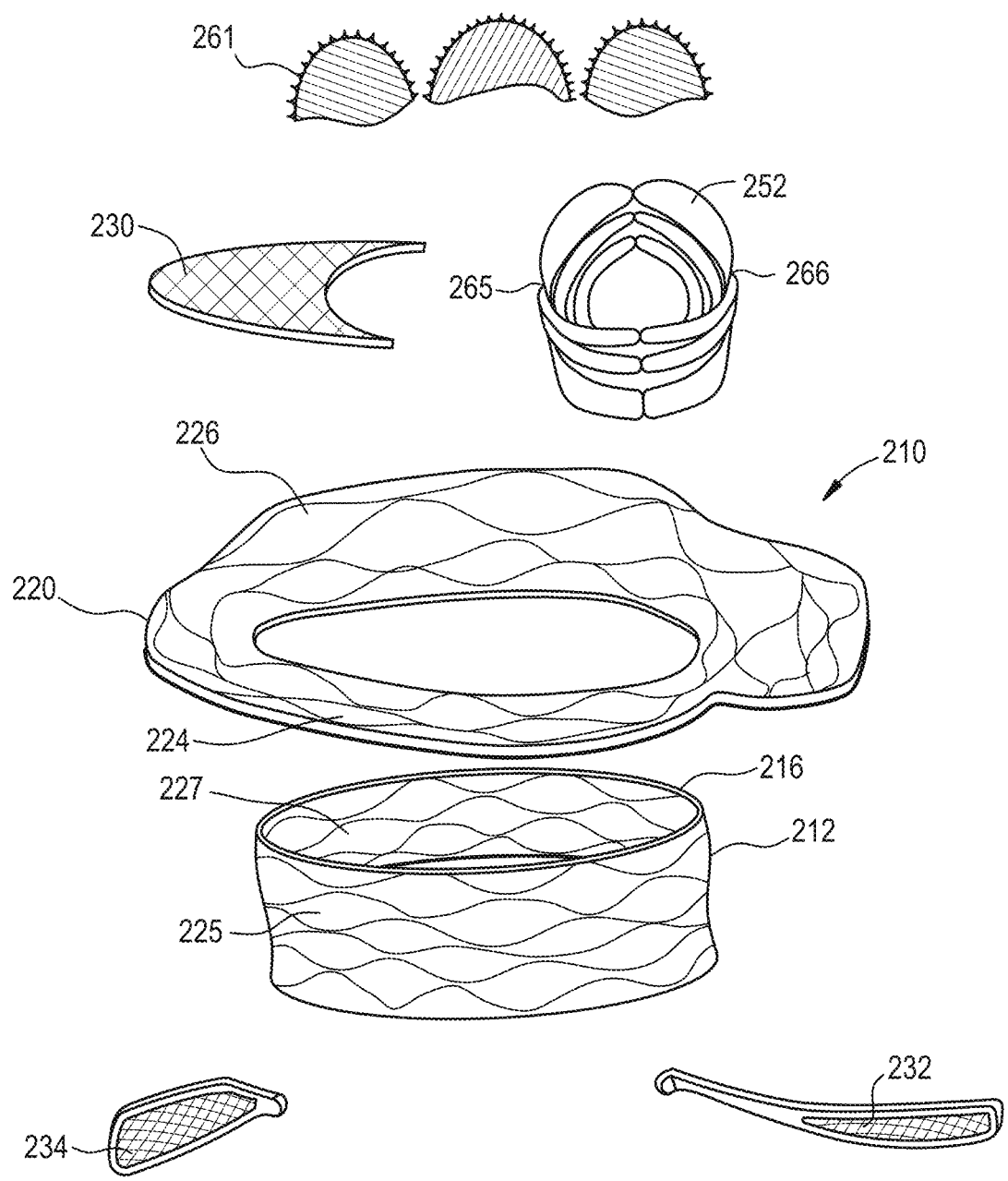
FIG. 3 is an exploded view illustration of the prosthetic valve of FIG. 2.

FIGS. 2 and 3 are illustrations of a side perspective view and an exploded view, respectively, of a side delivered transcatheter heart valve 202 with a collapsible flow control component 250 mounted within the annular outer support frame 210 according to an embodiment. The annular outer support frame 210 is made from a shape-memory material such as Nickel-Titanium alloy, forexample Nitinol, and is therefore a self-expanding structure from a compressed configuration to an expanded configuration. The annular (outer) support frame 210 has a transannular and/or body section 212 that circumscribes, forms, and/or defines a central (interior) channel 214 about and/or along a vertical or central axis (y-axis). The annular outer support frame 210 further has a distal side 222 with a distal anchoring element 232 (e.g., a superelastic wire loop distal tab) coupled to and/or extending from the distal side 222 and a proximal side 219 with a proximal anchoring element 234 (e.g., a superelastic wire loop proximal tab) coupled to and/or extending from the proximal side 219. The annular support frame 210 has an atrial collar component 220 attached circumferentially at a top edge 216 of the transannular and/or body section 212. The atrial collar 220 is shaped to conform to the native deployment location. In a tricuspid replacement, for example, the atrial collar 220 can have a tall back wall portion to conform to the septal area of the native valve, and can have a distal and proximal upper collar portion. The distal upper collar portion can be larger than the proximal upper collar portion to account for the larger flat space above (atrial) the right ventricular outflow tract (RVOT) subannulararea.

The collapsible (inner) flow control component 250 is mounted within the annular outer support frame 210 and is configured to permit blood flow in a first direction, e.g. atrial to ventricular, through an inflow end of the valve 202 and block blood flow in a second direction, opposite the first direction, through an outflow end of the valve 202. The collapsible (inner) flow control component 250 can have a foldable and compressible inner wire frame 252 (also referred to as "inner leaflet frame" or "inner frame") with a distal fold area 266 and a proximal fold area 261 (e.g., also referred to as a hinge area, coupling area, edge portion or connected edge portion, etc.). A set of 2-4 flexible leaflets 261 are mounted in or on the inner frame 252. In some embodiments, for example, the flow control component 250 has three leaflet 261 cusps or pockets mounted within the inner frame 252 (FIG. 3).

As shown in FIG. 2, the inner flow control component 250 of the valve 202 has a diameter and/or perimeter that is smaller than a diameter and/or perimeter of the central channel 214. An optional mesh component of biocompatible material that may be used as a spacer element 230 is attached to the collar 220 and is used to at least partially cover the central channel 214 not otherwise occupied by the flow control component. Moreover, a central or vertical axis (y-axis) defined by the inner frame 252 is parallel to but offset from the central or vertical axis (y-axis) defined by the outer support frame 210. In some implementations the spacer element 230 can facilitate the mounting of a portion of the flow control component 250 (e.g., an otherwise unsupported portion) to the outer support frame 210.

The inner flow control component 250, like the outer annular frame 210, is foldable and compressible. For example, the leaflet frame 252 is foldable along or in the direction of a z-axis (front to back) from a cylindrical configuration to a flattened cylinder configuration, where the fold lines are located on a distal side and on a proximal side. In some embodiments, being foldable along or in the direction of the z-axis allows the leaflet frame 252 to transition (e.g., flatten) from a ring or cylinder shape to a two-layer band (e.g., folded over on itself), or like a cylinder flattened into a rectangle or square joined along two opposing sides. In some implementations, such an arrangement allows the outer frame 210 and the flow control component 250 to reduce the radius along the z-axis until the side walls are in contact or nearly so. This also allows the outer frame 210 and the flow control component 250 to maintain a desired radius along the horizontal axis (x-axis) to minimize the number of wire cells, which make up the outer and the inner frames, that may be damaged by forces applied during folding and/or compression performed when loading the valve 202 into a delivery catheter.

The flow control component 250 (and thereby the inner leaflet frame 252), like the outer frame 210, is also vertically (y-axis) compressible, reducing the height of the entire valve 202 to fit within an inner diameter of a delivery catheter. By folding (compressing) in the direction of the z-axis and vertically compressing in the y-axis, the valve 202 is permitted to maintain a relatively large dimension along the horizontal, or x-axis. For example, a 60 mm or larger diameter valve can be delivered via transcatheter techniques. In some embodiments, the valve 202 in the expanded configuration has a height of about 5-60 mm or more and a diameter of about 25-80 mm or more. The length of the long axis (e.g., longitudinal axis or x-axis) of a valve, e.g. 60 mm, since it runs parallel to a central axis of the delivery catheter, is not limited by the relatively large amount of wire frame and cover material used for such a large valve. The use of a folded, compressed valve that is orthogonal to the traditional axial-delivery valves permits treatment options not available previously. In some embodiments, the horizontal x-axis of the valve 202 is at an intersecting angle of between 45-135 degrees to the central vertical y-axis when in an expanded configuration. In some embodiments, the horizontal x-axis of the valve 202 in the compressed configuration is substantially parallel to a length-wise cylindrical axis of the delivery catheter.

Figure 4:
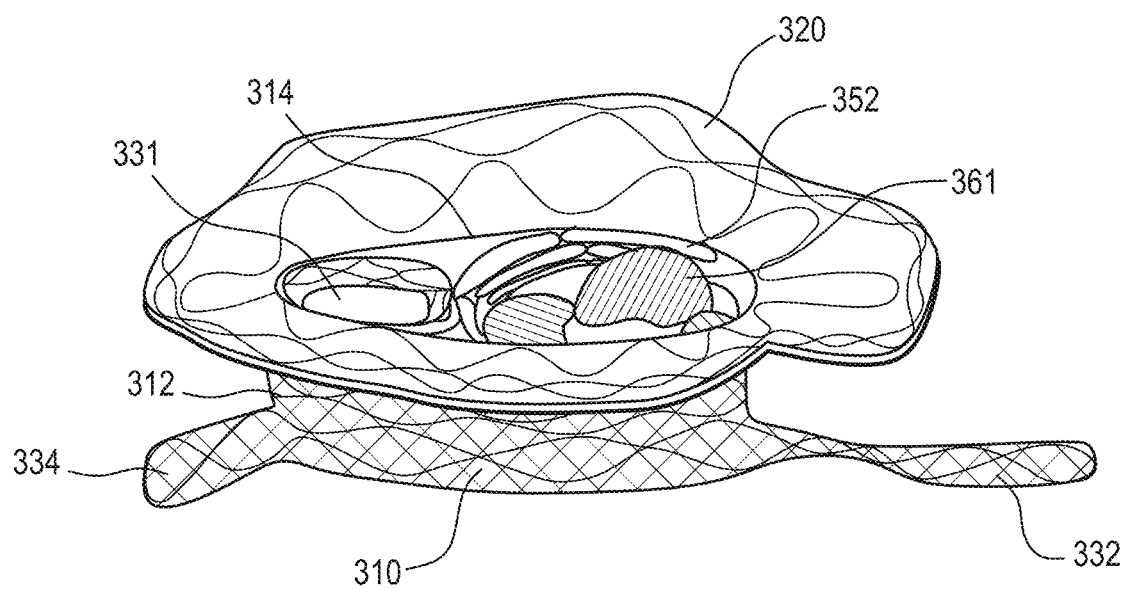
FIG. 4 is a side perspective view illustration of a prosthetic valve according to an embodiment.
Figure 5:
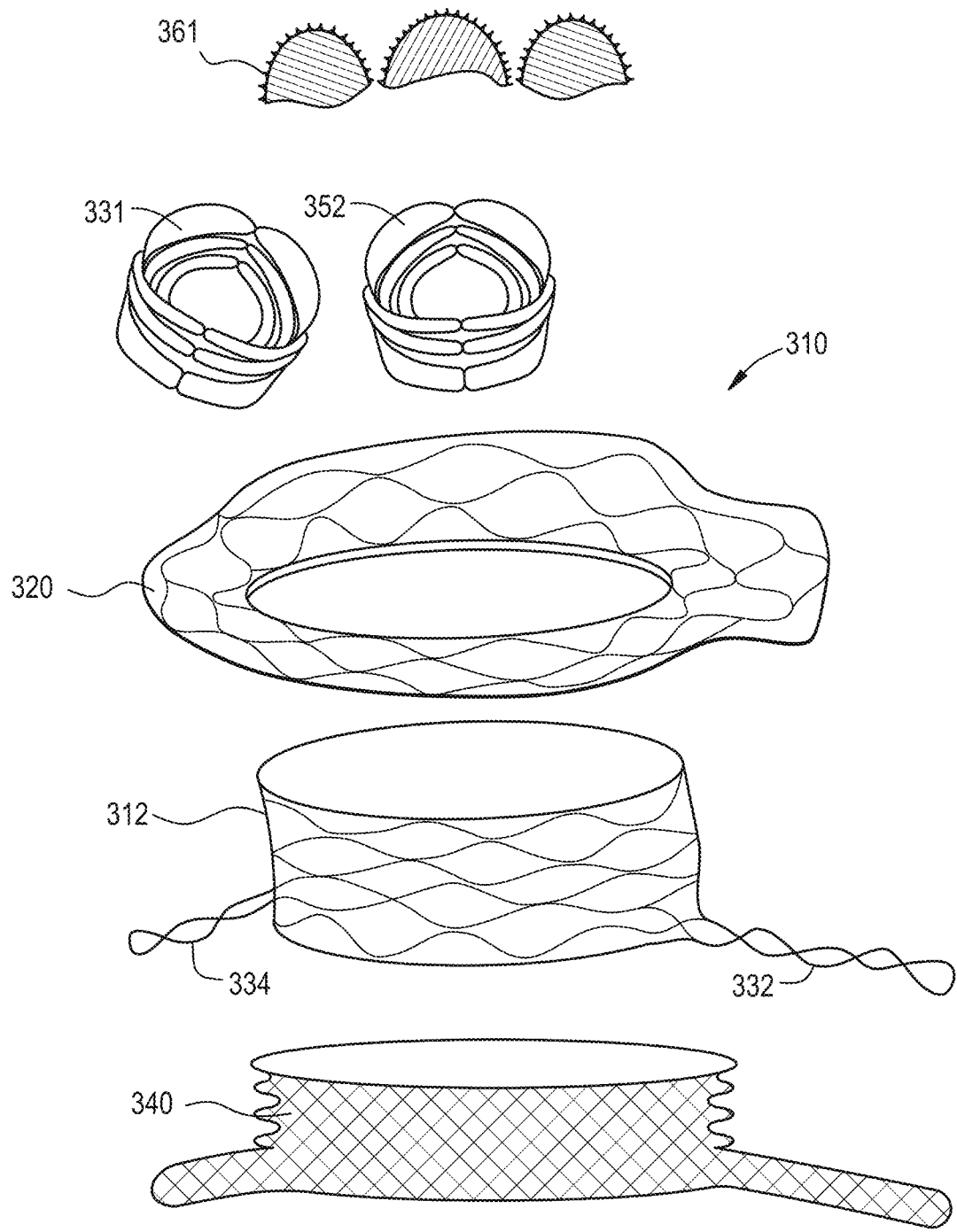
FIG. 5 is an exploded view illustration of the prosthetic valve of FIG. 4.

FIGS. 4 and 5 are illustrations of a side perspective view and an exploded view, respectively, of a side delivered transcatheter heart valve 302 with a collapsible flow control component 350 and a spacer 331 mounted within an annular outer support frame 310 according to an embodiment. The flow control component 350 is configured to permit blood flow in a first direction (e.g. atrial to ventricular) through an inflow end of the valve 302 and block blood flow in a second direction, opposite the first direction, through an outflow end of the valve 302.

The annular outer support frame 310 is made from a shape-memory material such as Nickel-Titanium alloy, for example Nitinol, and is therefore a self-expanding structure from a compressed configuration to an expanded configuration. The annular (outer) support frame 310 has a transannular and/or body section 312 that circumscribes, forms, and/or defines a central channel 314 about or along a vertical or central axis (y-axis). The annular support frame 310 has an atrial collar component 320 attached circumferentially at a top edge of the transannular and/or body section 312. The atrial collar 320 is shaped to conform to the native deployment location. In a tricuspid replacement, for example, the atrial collar 320 can have a tall back wall portion to conform to the septal area of the native valve, and can have a distal and proximal upper collar portion. The distal upper collar portion can be larger than the proximal upper collar portion to account for the larger flat space above (atrial) the right ventricular outflow tract (RVOT) sub annular area.

The outer support frame 310 has a distal anchoring element 332 (e.g., a superelastic wire loop distal tab) coupled to and/or extending from a distal side of the outer support frame 310 and a proximal anchoring element 334 (e.g., a superelastic wire loop proximal tab) coupled to and/or extending from a proximal side of the outer support frame 310. In some embodiments, the distal anchoring element 332 and the proximal anchoring element 334 can be integrated tabs that are unitarily constructed with the body section 312 of the outer frame 310. The anchoring elements 332 and 334 may vary in size and shape. For example, a distal anchoring element 332 (e.g., an RVOT tab) may be longer to reach into the entry of the pulmonary artery (in the case of a tricuspid replacement). In some embodiments, the shapes of the anchoring elements 332 and 334 are configured to conform to the A1 and A3 commissural areas of the mitral valve.

At least the outer support frame 310 of the valve 302 is covered, wrapped, and/or surrounded by a biocompatible cover 340. The biocompatible cover 340 can be a mesh material, a pericardial tissue, a woven synthetic polyester material, and/or any other suitable biocompatible material such as those described above.

The collapsible (inner) flow control component 350 is mounted within the annular outer support frame 310 adjacent to the spacer 331. The flow control component 350 has a foldable and compressible inner wire frame 352 (also referred to as "inner leaflet frame" or "inner frame") with two or more fold areas, hinge areas, coupling areas, elastically deformable regions, etc. A set of 2-4 flexible leaflets 361 are mounted in or on the inner frame 352. In some embodiments, the flow control component 350 has three leaflet 361 cusps or pockets mounted within the inner frame 352 (FIG. 5). The inner flow control component 350, like the outer annular frame 310, is foldable and compressible. For example, the leaflet frame 352 is foldable along or in the direction of a z-axis (e.g., foldable at the fold areas or the like) from a cylindrical configuration to a flattened cylinder configuration, where the fold areas are located on a distal side and on a proximal side of the inner frame 353. The flow control component 350, like the outer frame 310, is also vertically (y-axis) compressible to a shortened or compressed configuration. By folding (compressing) in the direction of the z-axis and vertically compressing in the y-axis, the valve 302 is permitted to maintain a relatively large dimension along the horizontal, or x-axis.

The flow control component 350 has a diameter and/or perimeter that is smaller than a diameter and/or perimeter of the central channel 314 of the outer frame 310. Moreover, a central or vertical axis (y-axis) defined by the inner frame 352 is parallel to but offset from the central or vertical axis (y-axis) defined by the outer support frame 310 (FIG. 4). In some implementations the spacer element 331 is disposed within the central channel 314 and can facilitate the mounting of a portion of the flow control component 350 (e.g., an otherwise unsupported portion) to the outer support frame 310. In some embodiments, the spacer element 331 can be a cylindrical tube or frame configured to support a portion of the flow control component 350. In other embodiments, the spacer element 331 can be any suitable shape, size, and/or configuration. For example, the spacer element 331 can be a wire loop or the like that can be coupled to and/or integrated with a drum or collar of the frame 310.

In some embodiments, the spacer element 331 can also provide for controlled regurgitation of the valve 302. For example, in some embodiments, the spacer 331 can be uncovered or covered with a fluid permeable mesh, cloth, and/or biocompatible material. In some embodiments, the uncovered spacer 331 can be later plugged with an inserted stent, cover, plug, and/or the like (e.g., once regurgitation is no longer desirable for the proper functioning of the heart of the patient).

In some embodiments, the spacer element 331 can be similar to or substantially the same as the inner frame 352 of the flow control component 350 without having leaflets mounted therein. In other embodiments, the spacer element 331 can include leaflets mounted therein (e.g., similar in form and/or configuration as the leaflets 361 or different in form and/or configuration from the leaflets 361). Similarly stated, the valve 302 can include two flow control components 350 with each flow control component 350 acting as a spacer with respect to the other flow control component 350.

Figure 6:
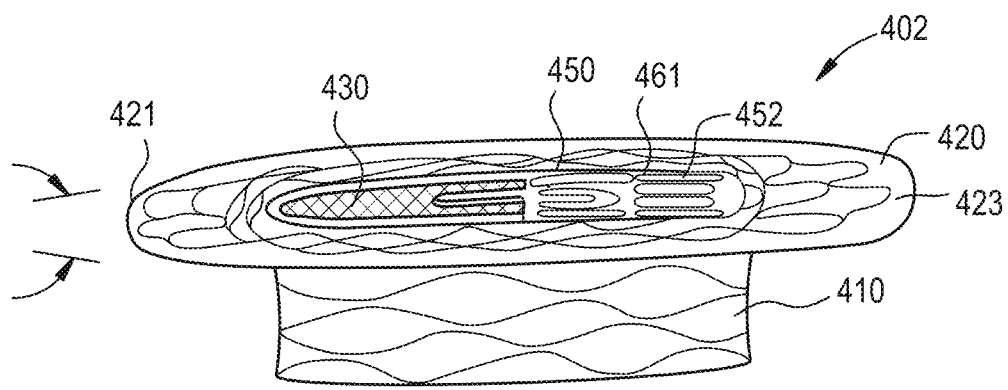
FIGS. 6-8 are side perspective views illustrating a prosthetic valve according to an embodiment, and shown being transitioned to a compressed configuration and loaded into a delivery catheter for transcatheter delivery to a native annulus of a heart.

FIGS. 6-10 illustrate a side-delivered transcatheter prosthetic heart valve 402 according to an embodiment, and shown being transitioned to a compressed configuration, loaded into a delivery catheter for transcatheter delivery to a native annulus of a heart, and partially released from the deliver catheter for deployment into the native annulus. FIG. 6 shows the prosthetic heart valve 402 in a folded configuration along the z-axis (front to back when viewed from the broader side). FIG. 6 shows an outer frame 410 with a flow control component 450 and a spacer 430 disposed within a central channel of the outer frame 410. A collar 420 of the outer frame 410 is shown folded/flattened at proximal and distal hinge points or fold areas 421 and 423. The flow control component 450 is shown including leaflets 461 that are mounted within a folded/flattened inner frame 452 of the flow control component 450.

Figure 7:
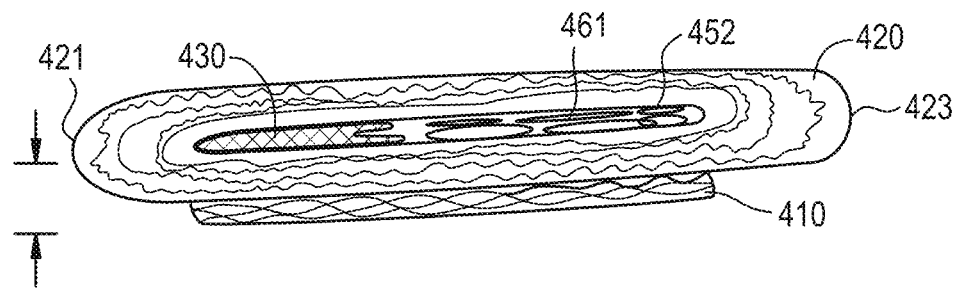

FIG. 7 shows the prosthetic heart valve 402 in a vertically compressed configuration. For example, the outer frame 410 is laterally folded (z-axis) and compressed vertically (y-axis) with the collar 420 laterally folded (z-axis) and compressed (y-axis), along a fold line between hinge points or fold areas 421 and 423. FIG. 7 also shows the spacer 430 and the flow control component 450 having the leaflets 461 mounted within inner frame 452, in the compressed configuration.

Figure 8:
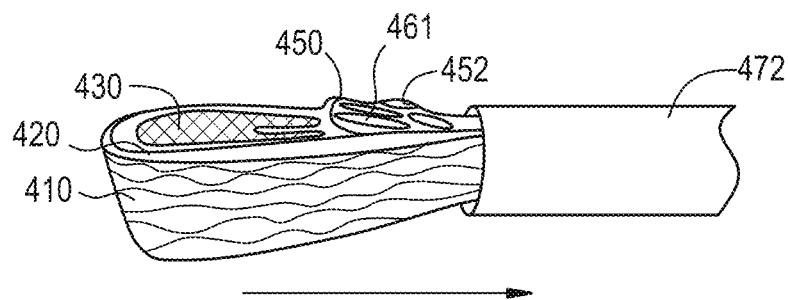

FIG. 8 shows the prosthetic heart valve 402 partially loaded into a delivery catheter 472. The outer frame 410, the folded collar 420, the spacer 430, and the flow control component 450 having the leaflets 461 and the inner frame 452 are in and/or are being transitioned into a folded and compressed configuration.

Figure 9:
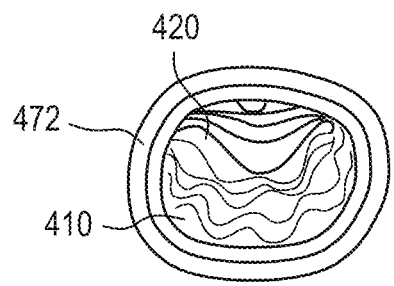
FIG. 9 is an end view illustration of the delivery catheter with the prosthetic valve of FIGS. 6-8 disposed within a lumen thereof.

FIG. 9 is an illustration of an end view of the delivery catheter 472 that shows the loaded valve 402 in the folded and compressed configuration.

Figure 10:
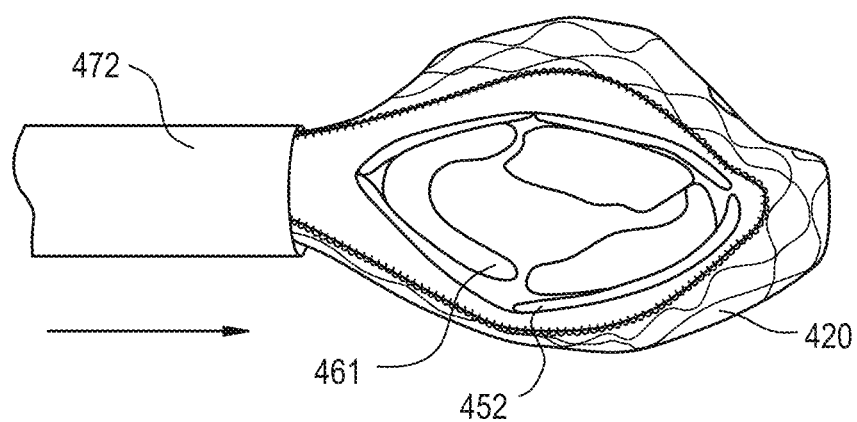
FIG. 10 is a top view illustration of the prosthetic valve of FIGS. 6-9 shown partially released from the delivery catheter for deployment into the native annulus.

FIG. 10 shows the folded and compressed valve 402 being released from the delivery catheter 472, and beginning to transition from the folded and compressed configuration to an expanded configuration for deployment into the native annulus.

Figure 11:
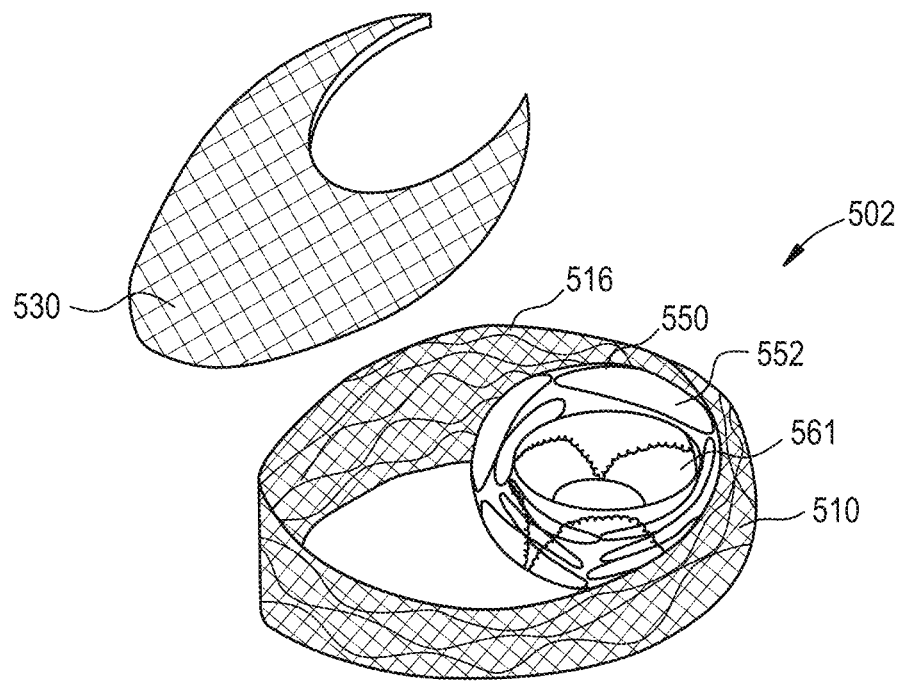
FIGS. 11 and 12 are top perspective views illustrating a prosthetic valve according to an embodiment, and shown with a spacer removed from an outer frame and with the spacer coupled to the outer frame, respectively.

FIGS. 11-14 illustrate a side-delivered transcatheter prosthetic heart valve 502 according to an embodiment. FIG. 11 shows the valve 502 with an outer frame 510 and a flow control component 550. The outer frame 510 is shown without an atrial collar. The valve 502 is further shown with a spacer element 530 (e.g., mesh spacer frame) removed for viewing. The flow control component 550 is shown mounted within a central channel of the outer frame 510. The flow control component 550 is shown in an offset position relative to a central or vertical axis of the outer frame 510. The flow control component 550 is shown including a set of leaflets 561 mounted (e.g., sewn) within an inner frame 552.

Figure 12:
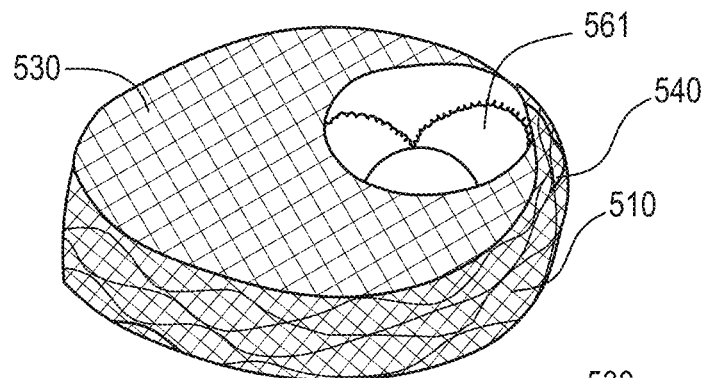

FIG. 12 is a top perspective view of the valve 502 that shows the spacer element 530 mounted to a top edge 516 of the outer frame 510. The outer frame 510 is also shown having a sidewall cover 540 formed of a biocompatible material and/or mesh.

Figure 13:
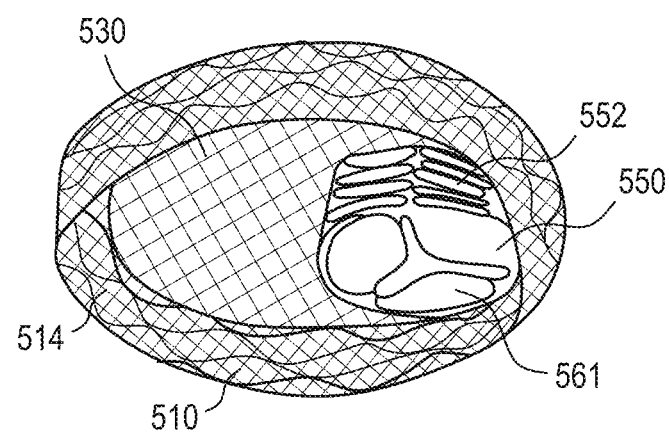
FIG. 13 is a bottom perspective view illustration of the prosthetic valve of FIG. 12.

FIG. 13 is a bottom perspective view of the valve 502 showing the flow control component, having the inner frame 552 and leaflets 561, disposed within the central channel 514 of the outer frame 510. The spacer element 530 is shown mounted on the top edge 516 of the outer frame 510.

Figure 14:
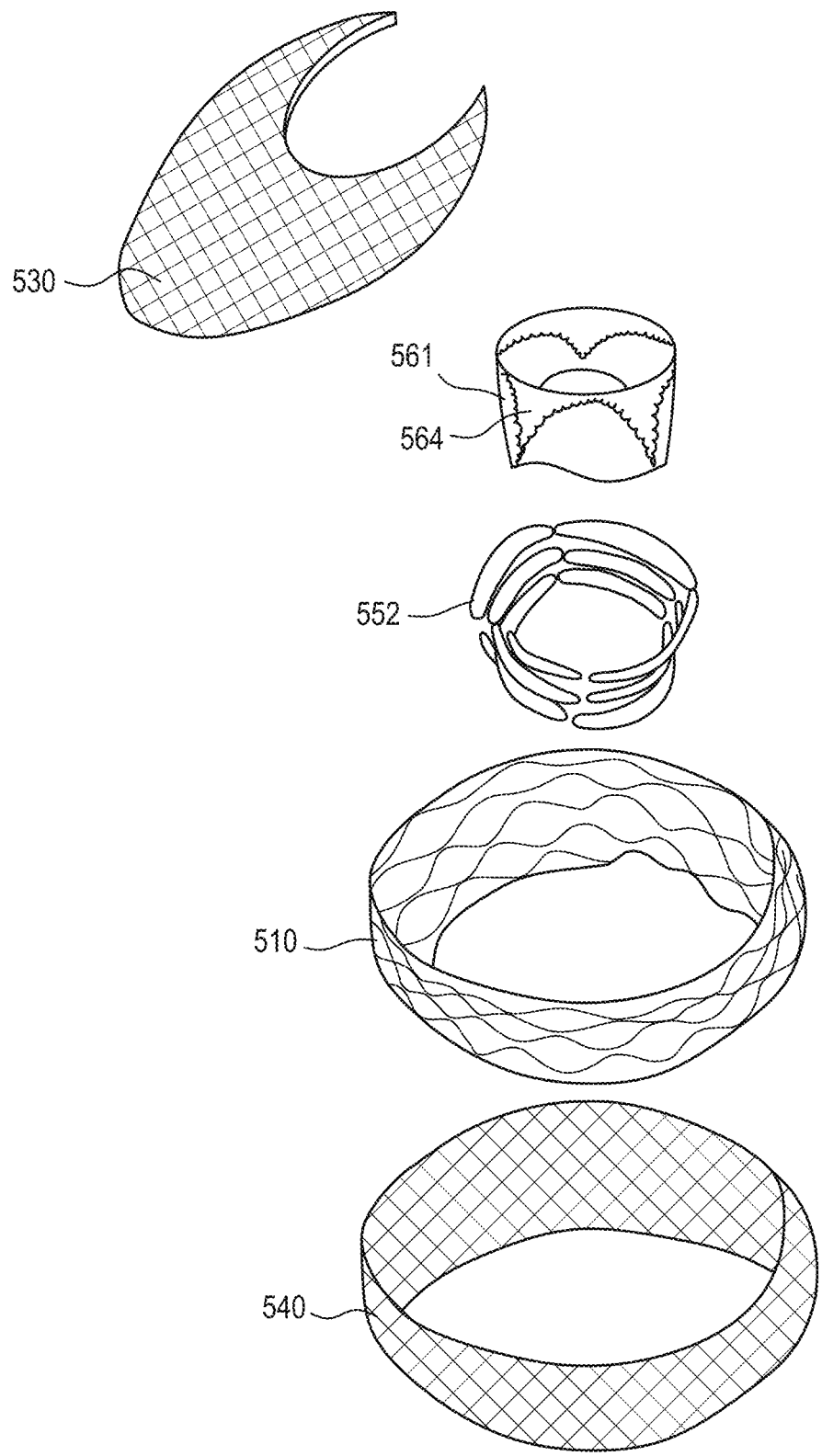
FIG. 14 is an exploded view illustration of the prosthetic valve of FIGS. 11-13.

FIG. 14 is an exploded view of the valve 502 that shows the outer frame 510 (e.g., without an atrial collar), the sidewall cover 540, the leaflets 561 mounted (e.g., sewn) on and/or into a band 564, which in turn is mounted (e.g., sewn) into the inner frame 552, and the spacer element 530.

Figure 15:
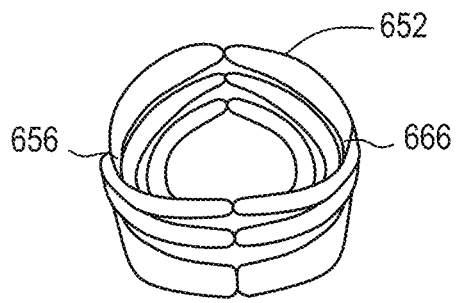
FIG. 15 is a top perspective view illustration of an inner frame of a flow control component included in a prosthetic valve according to an embodiment.

FIGS. 15-18 illustrate an inner leaflet frame 652 of a flow control component according to an embodiment. FIG. 15 is an illustration of a top perspective view of the inner leaflet frame 652. In some embodiments, the inner leaflet frame 652 is formed of two separate wireframe sheets or members that are coupled at lateral connection points 665 and 666 (e.g., fold areas, elastically deformable regions, coupled edged portions, etc.). The inner leaflet frame 652 is shown in an expanded or cylindrical configuration (e.g., prior to being folded and/or compressed).

Figure 16:
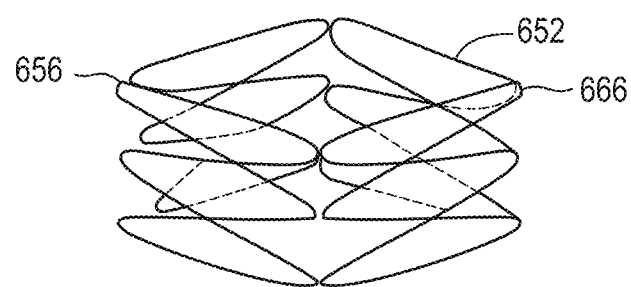
FIGS. 16-18 are various views illustrating the inner frame of FIG. 15 and shown in a partially folded configuration, a folded configuration, and a folded and compressed configuration, respectively.
Figure 17:
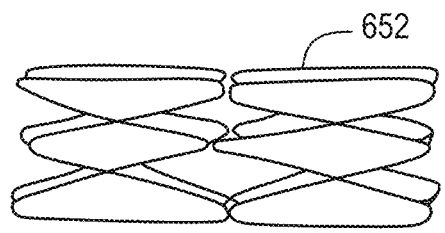

FIG. 16 shows the inner leaflet frame 652 in a partially folded configuration. The inner leaflet frame 652 is shown with wireframe sidewalls that allow for rotating or hinging at least at the lateral connection points 665 and 666. The inner leaflet frame 652 can be configured to fold as shown in response to the valve being folded and/or compressed for delivery. FIG. 17 shows the inner leaflet frame 652 in a completely folded configuration. The wireframe sidewalls have been rotated, hinged, and/or folded at their lateral connection points 665 and 666.

Figure 18:
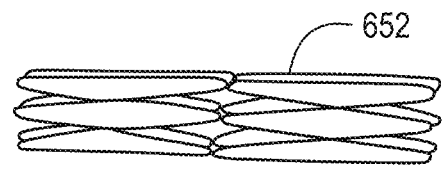

FIG. 18 shows the inner leaflet frame 652 in a folded and vertically compressed into a compressed configuration. The wireframe sidewalls can form cells (e.g., diamond-shaped cells or the like) that can oriented in a direction of compression to allow for elastic compression of the inner frame 652. In some embodiments, the inner frame 652 can be vertically compressed into a pleated or accordion (compressed) configuration.

Figure 19:
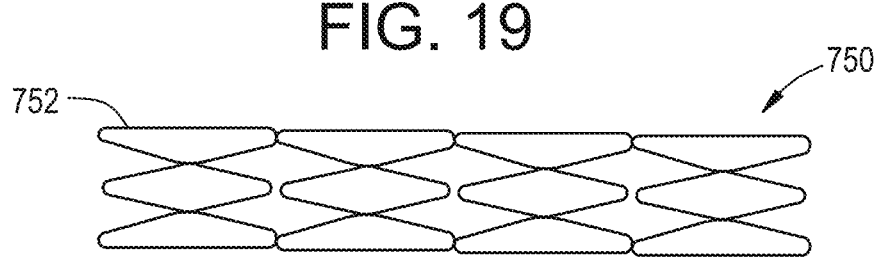
FIG. 19 is a side view illustration of an inner frame of a flow control component included in a prosthetic valve and shown as a linear wireframe sheet prior to being formed into a cylindrical configuration, according to an embodiment.
Figure 20:
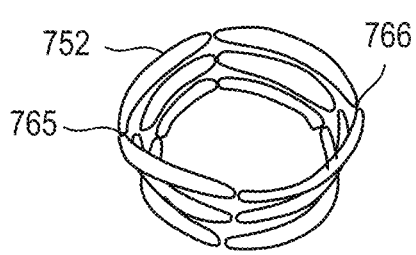
FIG. 20 is a side perspective view of the inner frame of FIG. 19 and shown in the cylindrical configuration.

FIGS. 19-25 illustrate one or more portions of an inner flow control component 750 according to an embodiment. FIG. 19 is an illustration of a side view of an inner leaflet frame 752 of the flow control component. The inner leaflet frame 752 is configured as and/or otherwise forms a linear wireframe sheet prior to being further assembled into a cylinder structure. FIG. 20 shows the inner leaflet frame 752 in the cylinder structure or configuration (or a conical structure or configuration) with edge portions of the linear wireframe sheet being connected or coupled at lateral connection points 765 and 766 (e.g., hinge areas, fold areas, etc.). Moreover, the inner leaflet frame 752 can be expanded (e.g., driven, formed, bent, etc.) from the linear sheet configuration into the cylinder structure or configuration.

Figure 21:
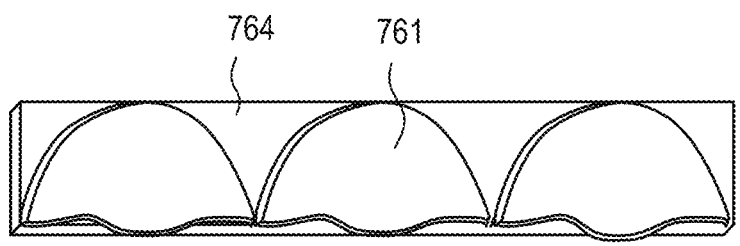
FIG. 21 is a side view illustration of a leaflet band of the inner flow control component having leaflet pockets sewn into a structural band of pericardial tissue and shown in a linear configuration.
Figure 22:
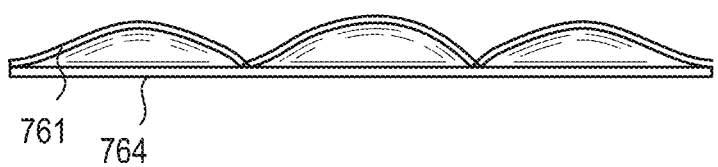
FIG. 22 is a bottom view illustration of the leaflet band of FIG. 23 and shown in the linear configuration.

FIGS. 21 and 22 are side view and a bottom view, respectively, illustrating a structural band 764 of pericardial tissue with leaflet pockets 761 sewn into the structural band 764, before assembly into a cylindrical leaflet component and before mounting on and/or into the inner frame 752 to form the collapsible (foldable, compressible) flow control component 750.

Figure 23:
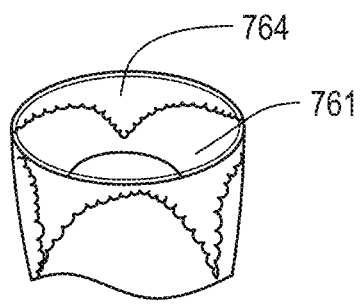
FIG. 23 is a side perspective view illustration of the leaflet band of FIGS. 21 and 22, and shown in a cylindrical configuration suitable for coupling to the inner frame of FIG. 20.

FIG. 23 is an illustration of a side perspective view of the structural band 764 formed of pericardial tissue with the leaflet pockets 761 sewn into the structural band 764, after assembly into the cylindrical leaflet configuration, the leaflet pockets 761 being disposed on an inner surface of the structural band 764.

Figure 24:
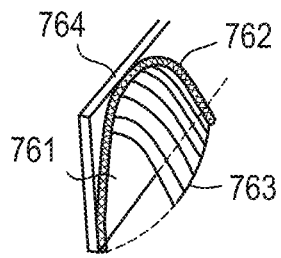
FIG. 24 is a side perspective view illustration of a portion of the leaflet band of FIG. 22 showing a single leaflet pocket sewn into the structural band.

FIG. 24 is an illustration of a side perspective view of part of the structural band 764 of pericardial tissue showing a single leaflet pocket 761 sewn into the structural band 764. The leaflet pocket 761 is shown with partial coaptation of the leaflet pocket 761 to the structural band 764 such that an open edge 763 extends outward and a sewn edge 762 forms a closed top parabolic edge providing attachment.

Figure 25:
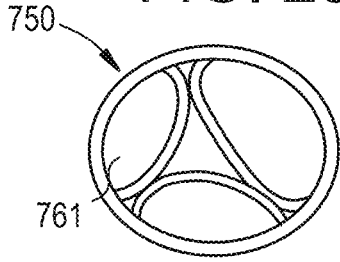
FIG. 25 is a bottom view illustration of the leaflet band of FIGS. 20-24 in the cylindrical configuration (shown in FIG. 21) and showing partial coaptation of the leaflets to form a partially closed fluid-seal.

FIG. 25 is an illustration of a bottom view of the flow control component 750. The cylindrical structural band 764 and leaflet components 761 are shown with partial coaptation towards forming a closed fluid-seal.

Figure 26:
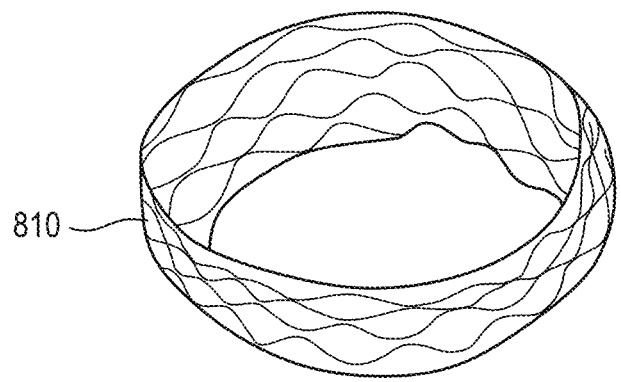
FIG. 26 is a top perspective view illustration of an outer frame of a prosthetic valve in a cylindrical configuration according to an embodiment.
Figure 27:
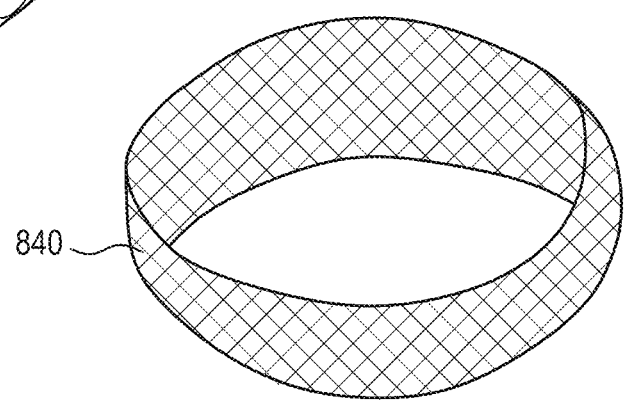
FIG. 27 is a top perspective view illustration of a biocompatible mesh configured to be coupled to the outer frame of FIG. 26.

FIGS. 26-30 illustrate one or more portions of an annular outer support frame 810 included in a prosthetic valve according to an embodiment. FIG. 26 is an illustration of a top perspective view of the outer wire frame 810 in a cylinder or expanded configuration. FIG. 27 is an illustration of a top perspective view of a biocompatible cover 340 configured to be coupled to, wrap, surround, and/or otherwise cover the outer wire frame 810. The biocompatible cover 340 can be a mesh material, a pericardial tissue, a woven synthetic polyester material, and/or any other suitable biocompatible material such as those described above.

Figure 28:
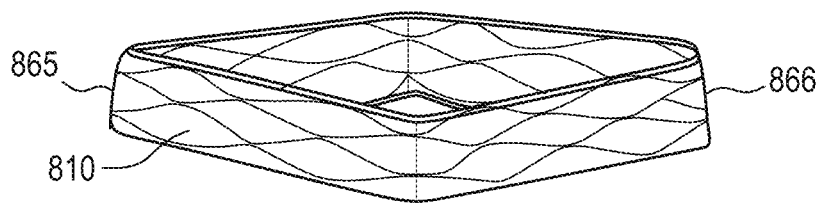
FIGS. 28-30 are side perspective views illustrating the outer frame of FIG. 26 and the biocompatible mesh of FIG. 27 coupled thereto, and shown in a partially folded configuration, a folded configuration, and a folded and compressed configuration, respectively.

FIG. 28 is an illustration of a top perspective view of the outer wire frame 810 in a partially folded configuration. The outer frame 810 includes lateral connection points 865 and 866, which can form and/or act a discontinuities, fold areas, hinge areas, elastically deformable regions, etc. The lateral connection points 865 and 866 can allow the outer wire frame 810 to be folded along or relative to a fold line or axis that extends through the lateral connection points 865 and 866. More specifically, the lateral connections points 865 and 866 can allow for elastic (i.e., non-permanent) deformation along the lateral connection points 865 and 866 that can allow the outer frame 810 to transition to the folded configuration without permanent deformation of or damage to the outer frame 810.

Figure 29:

FIG. 29 is an illustration of a side view of an outer frame 810 in a completely folded configuration with the wireframe sidewalls of the outer frame 810 rotated or hinged at their lateral connection points 865 and 866. In some implementations, the outer frame 810 can be folded to a substantially flat configuration without permanent deformation of the outer frame 810.

Figure 30:
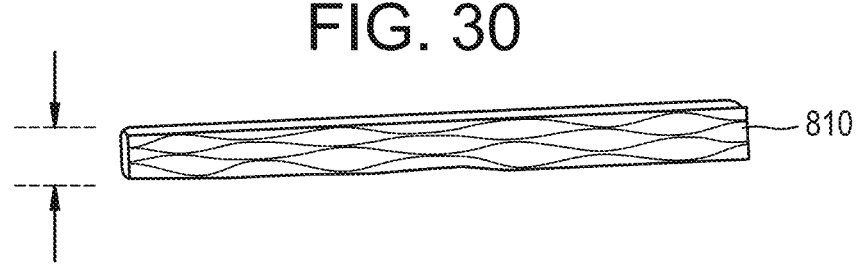

FIG. 30 is an illustration of a side view of the outer frame 810 in a folded and vertically compressed configuration with the wireframe sidewalls of the outer frame 810 laterally folded (FIG. 29) and vertically compressed. In some implementations, laterally folding and vertically (axially) compressing the outer frame 810 can place the outer frame 810 in the folded and compressed configuration (or said more simply, the compressed configuration).

Figure 31:
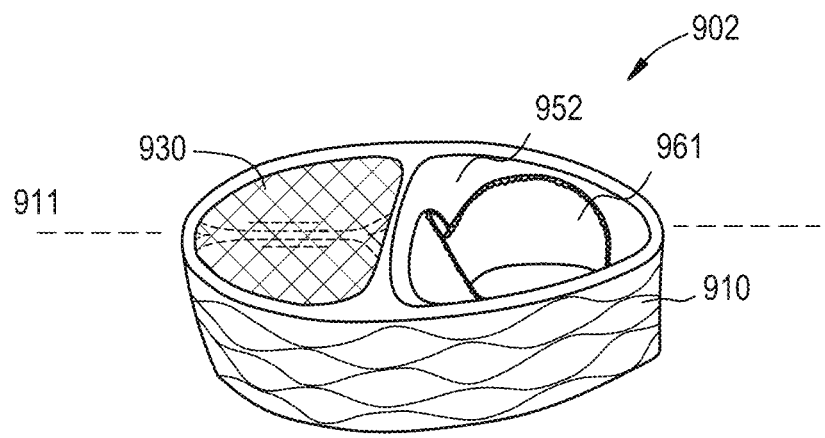
FIG. 31 is a top perspective view illustration of a prosthetic valve according to an embodiment.

FIG. 31 is an illustration of a top perspective view of an assembled valve 902 with an outer frame 910, a flow control component 950 having an inner leaflet frame 952 and three sewn leaflet pockets/cusps 961, an inner spacer element 930 having a mesh cover over a frame of the spacer element 930. A fold-line 911 (e.g., a x-axis or a longitudinal axis) is shown as a dashed line.

Figure 32:
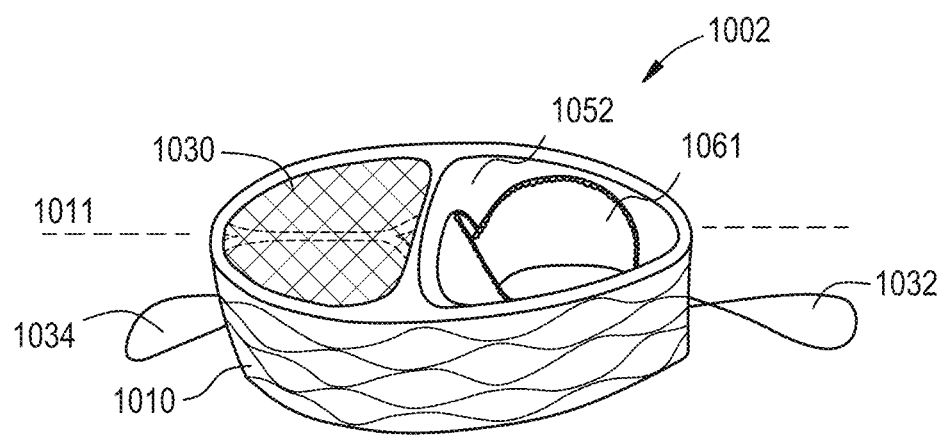
FIGS. 32 and 33 are a top perspective view illustration and a bottom perspective view illustration, respectively, of a prosthetic valve according to an embodiment.

FIG. 32 is an illustration of a top perspective view of an assembled valve 1002 with an outer frame 1010, a distal sub-annular anchoring/positioning element 1032 mounted on the outer frame 1010 adjacent a flow control component 1050, a proximal sub-annular anchoring/positioning element 1034 mounted on the outer frame 1010 in a different location, and an inner spacer frame 1030 having a mesh cover 1041 over the spacer frame 1030. The flow control component 1050 has an inner leaflet frame 1052 and three sewn leaflet pockets/cusps 1061. A fold-line 1011 is shown as a dashed line.

Figure 33:
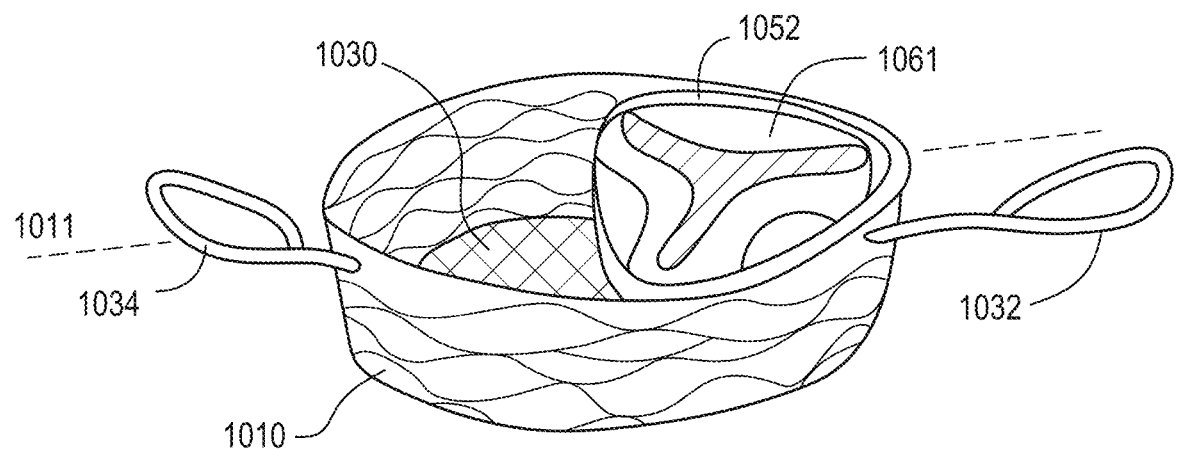

FIG. 33 is an illustration of a bottom perspective view of the assembled valve 1002 showing the outer frame 1010, the distal sub-annular anchoring/positioning element 1032 mounted on the outer frame 1010, the proximal sub-annular anchoring/positioning element 1034, the flow control component 1050 having the inner leaflet frame 1052 and three sewn leaflet pockets/cusps 1061, the spacer element 1030, and the fold-line 1011 shown as a dashed line. A hemodynamic washing cavity is shown under the spacer element 1030.

Figure 34:
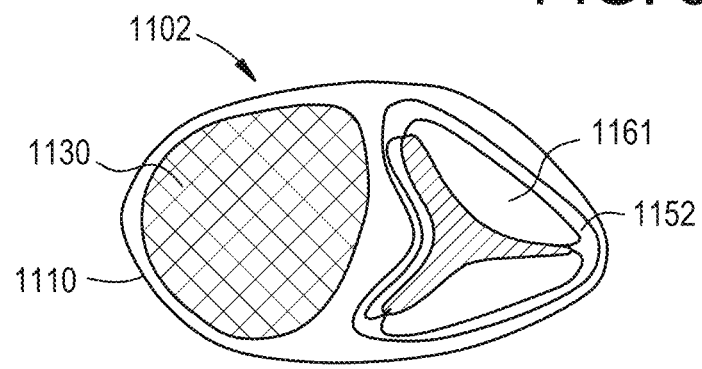
FIGS. 34 and 35 are top view illustrations of a prosthetic valve, each according to a different embodiment.

FIG. 34 is an illustration of a top view of an assembled valve 1102 with an outer frame 1110, a flow control component 1150 having an inner leaflet frame 1152 and three sewn leaflet pockets/cusps 1161, and a cover/spacer element 1130.

Figure 35:
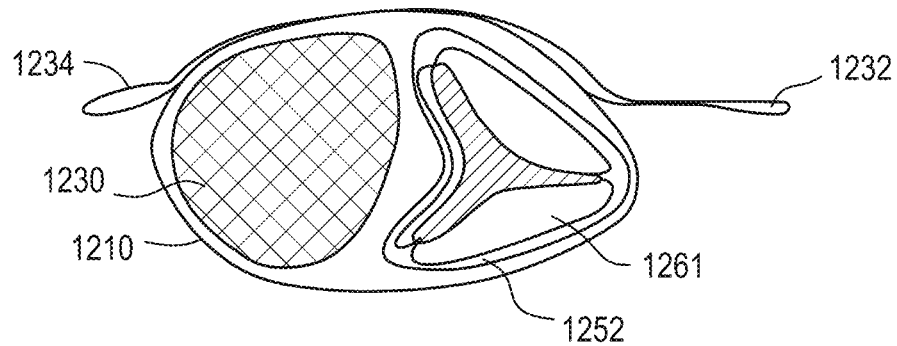

FIG. 35 is an illustration of a top view of an assembled valve 1202 with an outer frame 1210, a flow control component 1250 having an inner leaflet frame 1252 and three sewn leaflet pockets/cusps 1261 positioned in a central channel of the outer frame 1210, a cover/spacer element 1230, a distal sub-annular anchoring/positioning element 1232 mounted on the outer frame 1210 adjacent the flow control component 1250, and a proximal sub-annular anchoring/positioning element 1234 mounted on the outer frame 1210 adjacent the cover/spacer element 1230.

Figure 36:
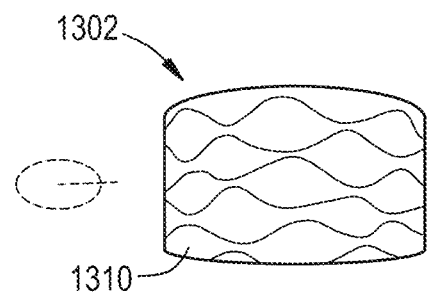
FIGS. 36-38 are a front plan view illustration, a front anterior plan view illustration, and a front septal plan view illustration of a prosthetic valve according to an embodiment.
Figure 37:
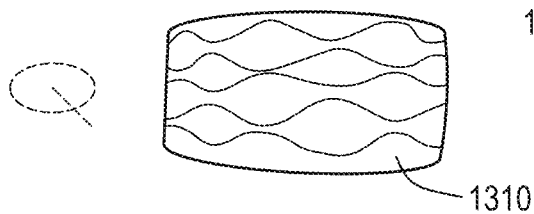
Figure 38:
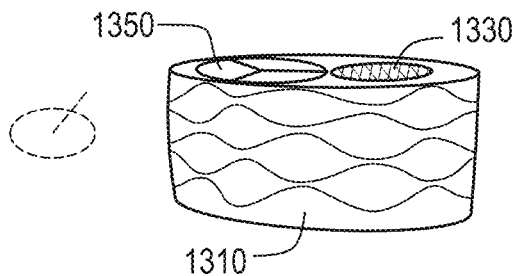

FIGS. 36-38 illustrate a non-tabbed valve 1302 according to an embodiment. FIG. 36 is an illustration of a front plan view of the non-tabbed valve 1302 having a foldable and compressible wire frame 1310 visible. FIG. 37 is an illustration of a front anterior plan view of the non-tabbed valve 1302 with the foldable and compressible wire frame 1310 visible. FIG. 38 is an illustration of a front septal plan view of the non-tabbed valve 1302 with the foldable and compressible wire frame 1310, a foldable and compressible inner flow control component 1350 in a distal position relative to the frame 1310 and a mesh-covered spacer element 1330 in a proximal location relative to the frame 1310.

Figure 39:
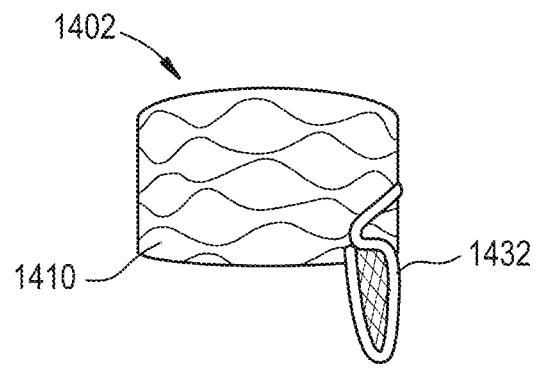
FIGS. 39-41 are a front plan view illustration, a front anterior plan view illustration, and a front septal plan view illustration of a prosthetic valve according to an embodiment.
Figure 40:
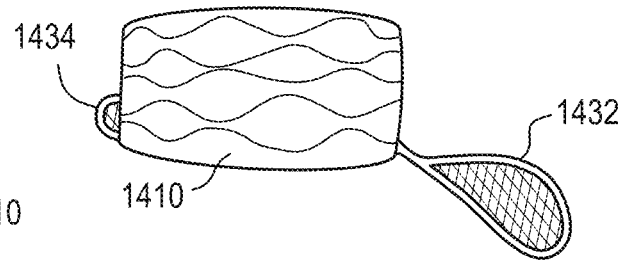
Figure 41:
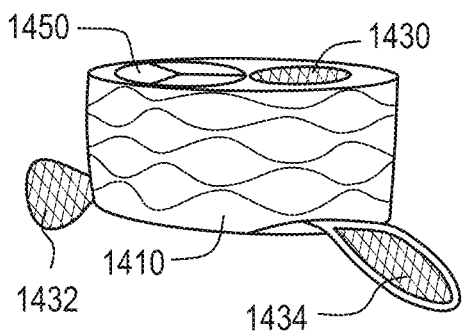

FIGS. 39-41 illustrate a tabbed valve 1402 according to an embodiment. FIG. 39 is an illustration of a front plan view of the tabbed valve 1402 having a foldable and compressible wire frame 1410 and a distal sub-annular anchoring and/or positioning element 1432 coupled to the frame 1410 and extending towards the viewer. FIG. 40 is an illustration of a front anterior plan view of the tabbed valve 1402 showing the foldable and compressible wire frame 1410, the distal sub-annular anchoring and/or positioning element 1432 coupled to the frame 1410 and extending towards the viewer, and a proximal sub-annular anchoring and/or positioning element 1434 coupled to the frame 1410 and extending away from the viewer. FIG. 41 is an illustration of a front septal plan view of the tabbed valve 1402 showing the foldable and compressible wire frame 1410, the distal sub-annular anchoring and/or positioning element 1432 coupled to the frame 1410 and extending to the left, and the proximal sub-annular anchoring and/or positioning element 1434 coupled to the frame 1410 and extending to the right. A foldable and compressible inner flow control component 1450 is shown in a distal position relative to the frame 1410 and a mesh-covered spacer element 1430 is shown in a proximal position relative to the frame 1410.

Figure 42:
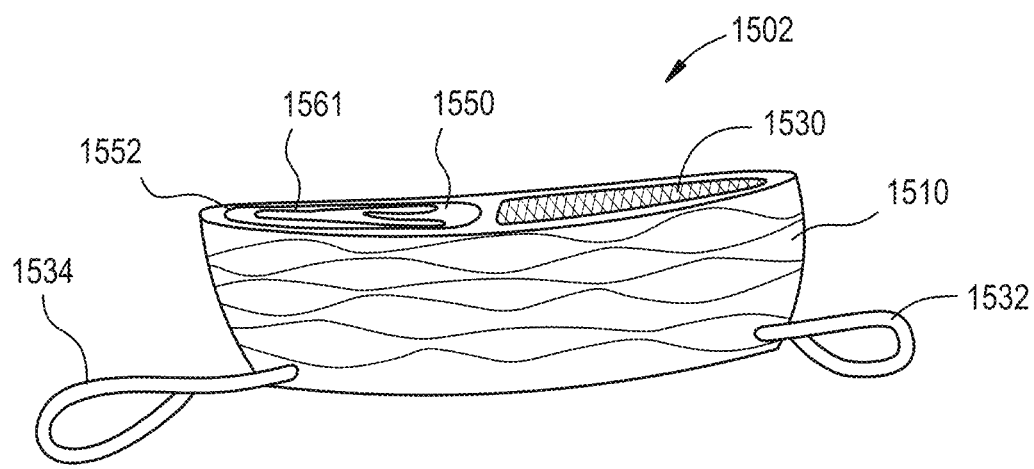
FIGS. 42-44 are a side septal plan view illustration, a top view illustration, and a bottom view illustration, respectively, of a prosthetic valve according to an embodiment.
Figure 43:
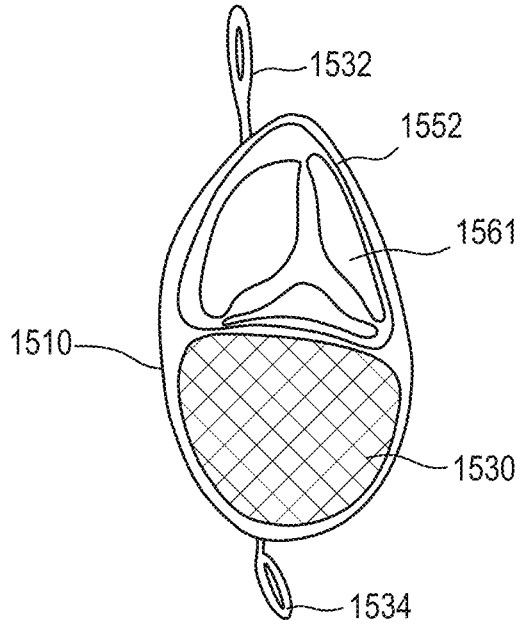
Figure 44:
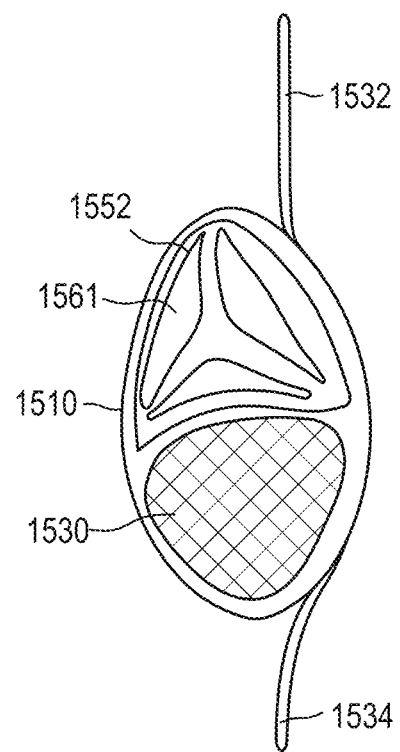

FIGS. 42-44 illustrate a tabbed valve 1502 according to an embodiment. FIG. 42 is an illustration of a side septal plan view of the tabbed valve 1502 having a foldable and compressible wire frame 1510, a distal sub-annular anchoring and/or positioning element 1532 coupled to the frame 1510 and extending towards a distal side, and a proximal sub-annular anchoring and/or positioning element 1534 coupled to the frame and extending away to a proximal side. A foldable and compressible inner flow control component 1550 is shown with an inner frame 1552 and a set of leaflets 1561 mounted thereon. A mesh covered spacer element 1530 is shown adjacent the flow control component 1550. FIGS. 43 and 44 are a top view and a bottom view, respectively, illustrating the assembled valve 1502 and showing the outer frame 1510, the distal sub-annular anchoring/positioning element 1532, the proximal sub-annular anchoring/positioning element 1534, the flow control component 1550 with the inner leaflet frame 1552 and three sewn leaflet pockets/cusps 1561, and mesh covered spacer element 1530.

Figure 45:
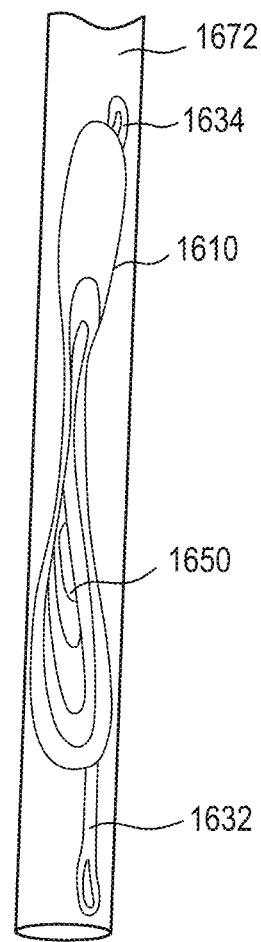
FIGS. 45 and 46 are top view illustrations of a prosthetic valve according to an embodiment and shown in a compressed configuration within a delivery catheter and partially released from the delivery catheter, respectively.
Figure 46:
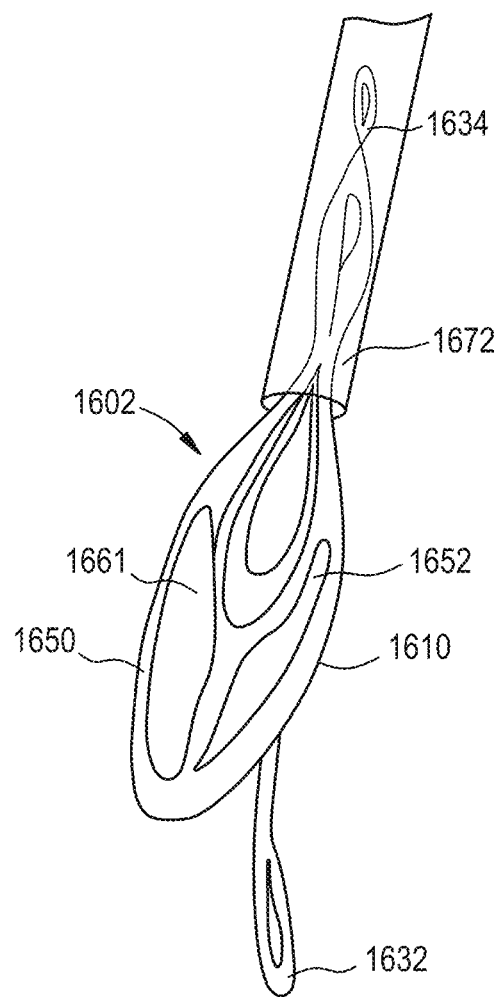

FIGS. 45 and 46 illustrate a valve 1602 according to an embodiment. FIG. 45 is an illustration of a top view of the valve 1602 shown in a compressed configuration and disposed (e.g., orthogonally loaded) within a delivery catheter 1672. The valve 1602 includes an outer frame 1610 having a first tab 1632 (e.g., a distal tab) extending forward along an x-axis and a second trailing tab 1634 (e.g., a proximal tab) extending backwards along the x-axis. A flow control component 1650 is shown disposed within the outer frame 1610.

FIG. 46 is an illustration of a top view of the valve 1602 partially released from the delivery catheter 1672. The distal tab 1632 is shown leading the valve 1602 (along a guide wire not shown in FIG. 46) to a deployment location. The flow control component 1650 is shown beginning to open and showing two of three leaflets 1661 opening from a folded, lie-flat configuration with the third leaflet opening from a folded configuration where it is folded back on itself when in the delivery catheter 1672.

Figure 47:
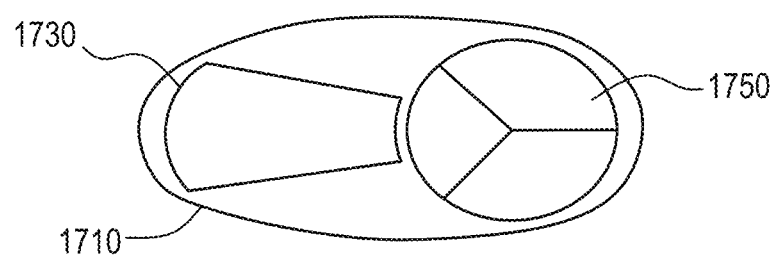
FIGS. 47-49 are top view illustrations of prosthetic valves according to various embodiments.

FIG. 47 is an illustration of a top view of a valve having an outer frame 1710, an off-center inner flow control component 1750 (leaflet in frame) mounted within the frame 1710, and an irregularly shaped spacer/support frame 1730 mounted within the frame 1710 adjacent the flow control component 1750, according to an embodiment.

Figure 48:
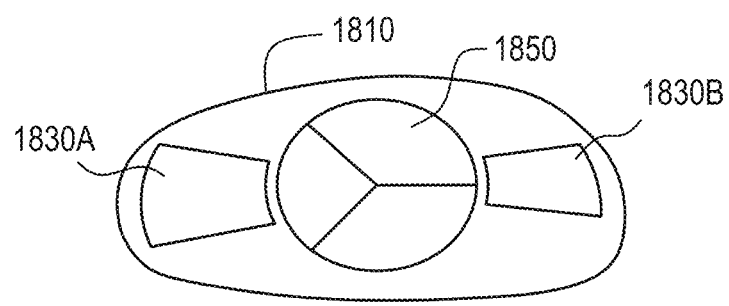

FIG. 48 is an illustration of a top view of a valve having an outer frame 1810, a centrally located inner flow control component 1850 (leaflet in frame) mounted within the frame 1810, and with a pair of irregularly shaped spacer/support frames 1830A, 1830B mounted on opposing sides of the inner flow control component 1850, according to an embodiment.

Figure 49:
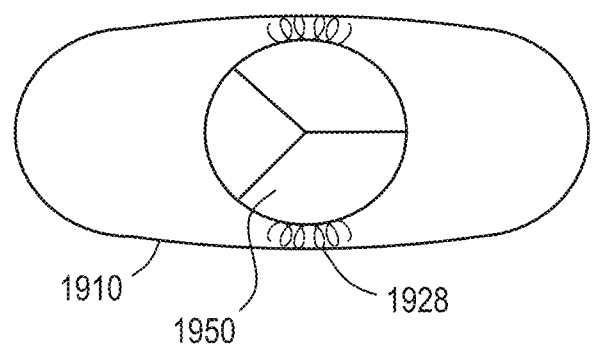

FIG. 49 is an illustration of a top view of a valve having an outer frame 1910, and a centrally located inner flow control component 1950 (leaflet in frame) mounted within the frame 1810, with a set of sewn attachment points 1928 configured to couple the inner flow control component to the outer frame 1910, according to an embodiment.

Figure 50:
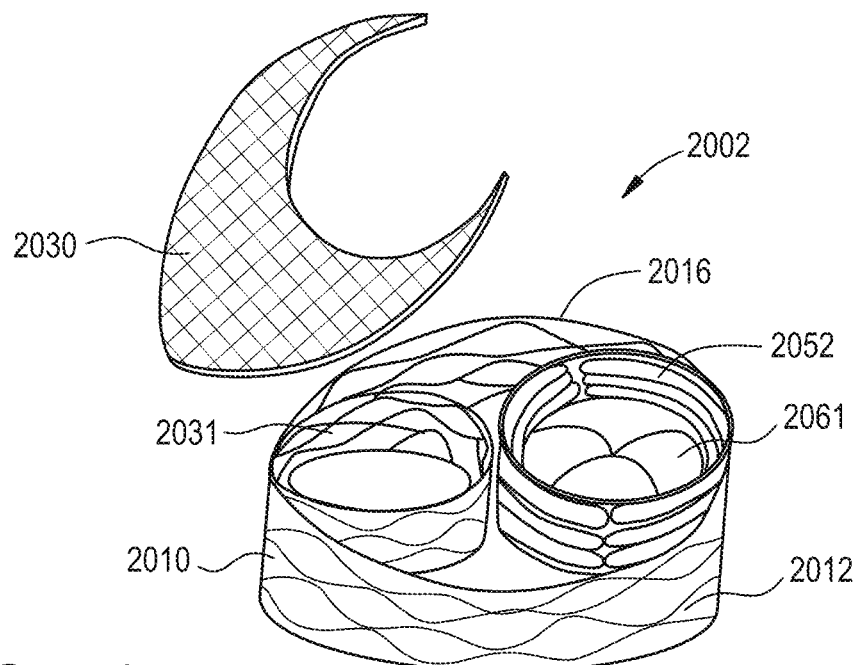
FIGS. 50 and 51 are top perspective views illustrating a prosthetic valve according to an embodiment, and shown with a spacer removed from an outer frame and with the spacer coupled to the outer frame, respectively.
Figure 51:
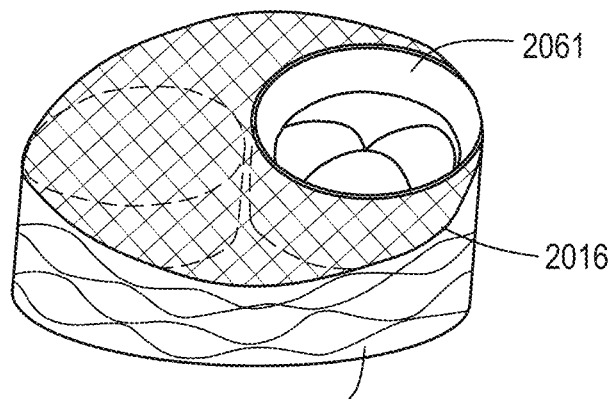
Figure 52:
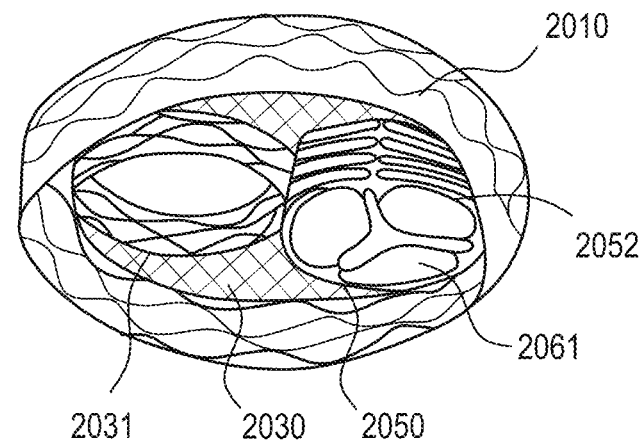
FIG. 52 is a bottom perspective view illustration of the prosthetic valve of FIG. 51.

FIGS. 50-52 illustrate a side-delivered transcatheter prosthetic heart valve 2002 according to an embodiment. FIG. 50 shows the valve 2002 with an outer frame 2010 and a flow control component 2050. The outer frame 2010 is shown without an atrial collar. The valve 2002 is further shown with a first spacer element 2030 (e.g., mesh covered spacer element) removed for viewing inside the frame 2010. The flow control component 2050 is shown mounted within a central channel of the outer frame 2010. The flow control component 2050 is shown in an offset position relative to a central or vertical axis of the outer frame 2010. The flow control component 2050 is shown including a set of leaflets 2061 mounted (e.g., sewn) within an inner frame 2052. A second spacer element 2031 (e.g., a cylindrical wireframe spacer or the like) is shown disposed within the central channel adjacent to the flow control component. The frame 2010, the flow control component 2050, and the first and second spacer elements 2030 and 2031 are foldable along the same x-axis and vertically compressible along the same y-axis.

FIG. 51 is a top perspective view of the valve 2002 that shows the first spacer element 2030 mounted to a top edge 2016 of the outer frame 2010.

FIG. 52 is a bottom perspective view of the valve 2002 showing the flow control component 2050, having the inner frame 2052 and leaflets 2061, disposed within the central channel 2014 of the outer frame 2010. The second spacer element 2031 is shown within the central channel 2014 adjacent the flow control component 2050. The first spacer element 2030 is shown mounted on the top edge 2016 of the outer frame 2010.

Figure 53:
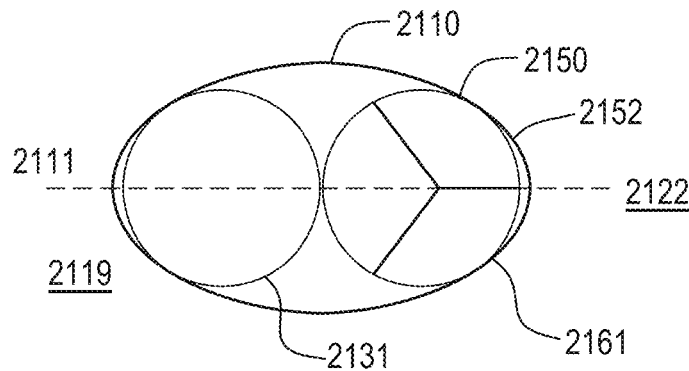
FIGS. 53-56 are top view illustrations of prosthetic valves according to various embodiments.

FIG. 53 is an illustration of a top view of a valve having an outer frame 2110, a distally located off-center inner flow control component 2150 having an inner frame 2152 and leaflets 2161 mounted in the inner frame 2152, and a proximal-side inner spacer frame 2131, with all three structures being foldable along the same x-axis 2111, according to an embodiment.

Figure 54:
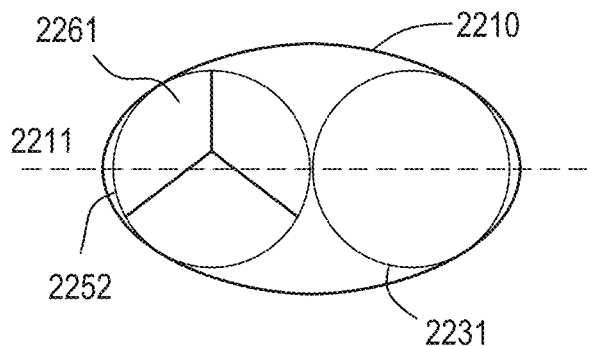

FIG. 54 is an illustration of a top view of a valve having an outer frame 2210, a proximally located off-center inner flow control component 2250 having an inner frame 2252 and leaflets 2261 mounted in the inner frame 2252, and a distal-side inner spacer frame 2231, with all three structures being foldable along the same x-axis 2211, according to an embodiment.

Figure 55:
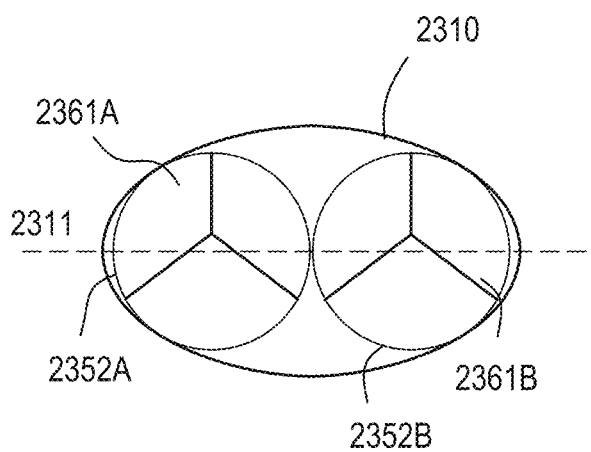

FIG. 55 is an illustration of a top view of a valve having an outer frame 2310, a proximally located off-center inner flow control component 2350A having an inner frame 2352A and leaflets 2361A mounted in the inner frame 2352A, and a distally located off-center inner flow control component 2350B having an inner frame 2352B and leaflets 2361B mounted in the inner frame 2352B, with all three structures being foldable along the same x-axis 2311, according to an embodiment. The proximal flow control component 2350A and the distal flow control component 2350B can be substantially the same size, shape, and/or configuration. In other embodiments, the proximal flow control component 2350A can have a first configuration and the distal flow control component 2350B can have a second configuration different from the first configuration. In some embodiments, the proximal flow control component 2350A can be configured to function as a replacement of a native valve while the distal flow control component 2350B can be configured to function to control regurgitation through the valve, or vice versa. In other embodiments, both flow control components 2350A and 2350B can be structurally and/or functionally similar to any of the flow control components described herein.

Figure 56:
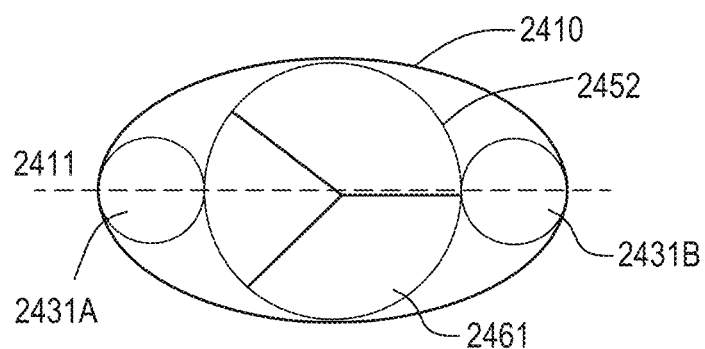

FIG. 56 is an illustration of a top view of a valve having an outer frame 2410, a centrally positioned inner flow control component 2450 having an inner frame 2452 and leaflets 2461 mounted in the inner frame 2452, and a pair of smaller cylindrical inner spacer frames 2431A and 2431B mounted on opposing sides of the inner flow control component 2450 to provide support within the interior dimension of the outer frame 2410, with all four structures being foldable along the same x-axis 2411, according to an embodiment.

Figure 57:
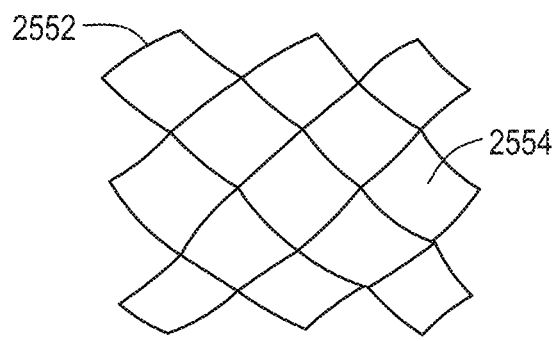
FIGS. 57-59 are side views illustrating portions of a wireframe with variable cell geometries according to various embodiments.

FIG. 57 is an illustration of a side view of a section of an inner wireframe 2552 of a flow control component showing that cell geometries can be variable from top to bottom and along a perimeter, with wire cells 2554 being shown in a uniform configuration, according to an embodiment.

Figure 58:
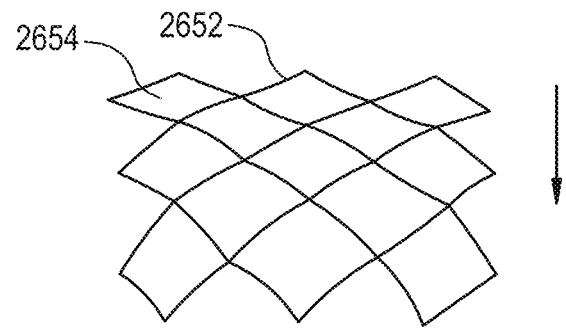

FIG. 58 is an illustration of a side view of a section of an inner wireframe 2652 of a flow control component showing that cell geometries can be variable from top to bottom and along the perimeter, with wire cells 2654 being shown in a non-uniform (height) configuration such that the wire cells 2654 have an increasing cell height from top (least) to bottom (most), according to an embodiment.

Figure 59:
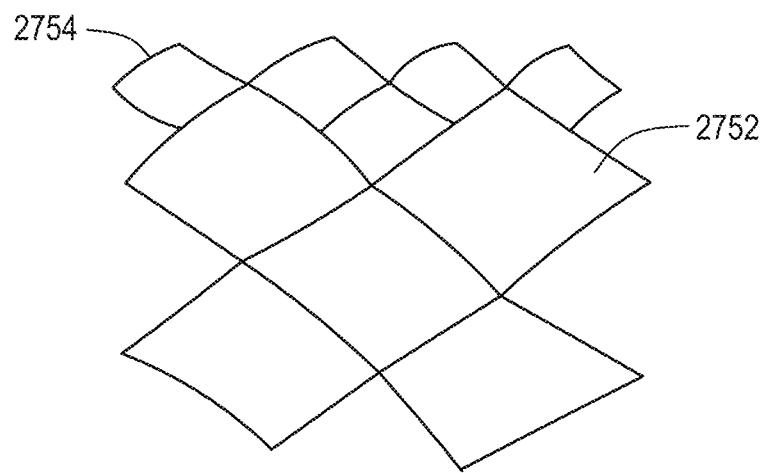

FIG. 59 is an illustration of a side view of a section of an inner wireframe 2752 of a flow control component showing that cell geometries can be variable from top to bottom and along the perimeter, with wire cells 2754 being shown in a non-uniform configuration where the individual cells 2754 are varying in size and shape, according to an embodiment.

Figure 60:
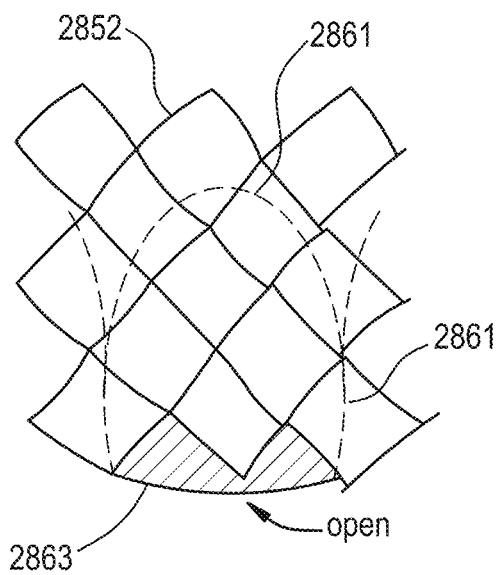
FIGS. 60 and 61 are side views illustrating a portion of a wireframe attached to a leaflet structure according to an embodiment and shown in an expanded configuration and a compressed configuration, respectively.
Figure 61:
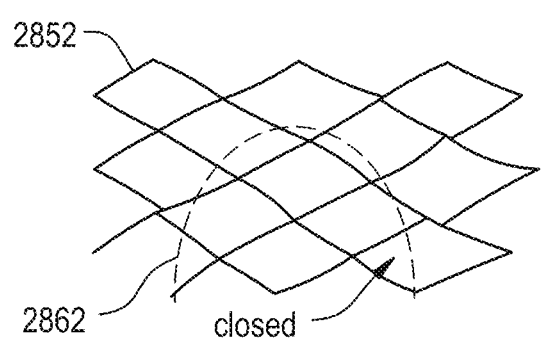

FIGS. 60 and 61 illustrate a portion of a flow control component according to an embodiment. FIG. 60 is a side view that shows a section of an inner wireframe 2852 that, during an elongation phase of a compressive cycle (e.g., when the valve is in deployed in a heart and subjected to compressive forces), the cell geometries can be tailored to work dynamically with a leaflet structure 2861 along a sewn edge 2762 to dampen the forces and to increase coaptation of the prosthetic leaflets 2861 along an open edge 2763.

FIG. 61 is a side view of a section of the inner wireframe 2852 in a compressed configuration that, during a compression phase of a compressive cycle (e.g., when the valve is in deployed in a heart and subjected to compressive forces), the cell geometries can be tailored to work dynamically with the leaflet structure 2861 along the sewn edge 2762 to dampen the forces and to increase coaptation of the prosthetic leaflets 2861.

Figure 62:
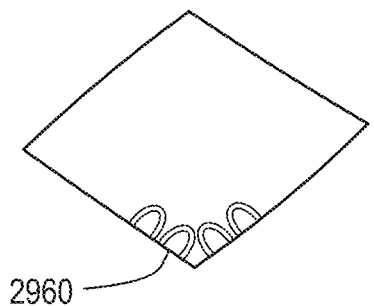
FIGS. 62-64 are side views illustrating a wire frame cell having a commissure attachment feature each according to an embodiment.

FIG. 62 is an illustration of a side view of a wire frame cell including an attachment feature 2960, such as eyelets, at a lower part of the diamond cell that can allow for consistent commissure attachment and valve compressibility, according to an embodiment.

Figure 63:
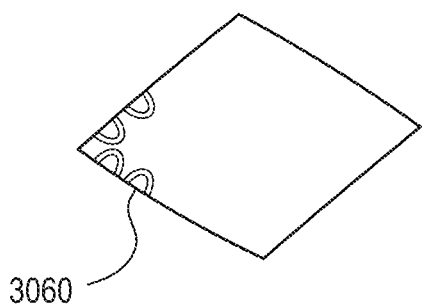

FIG. 63 is an illustration of a side view of a wire frame cell including an attachment feature 3060, such as eyelets, at a lateral part of the diamond cell that can allow for consistent commissure attachment and valve compressibility, according to an embodiment.

Figure 64:
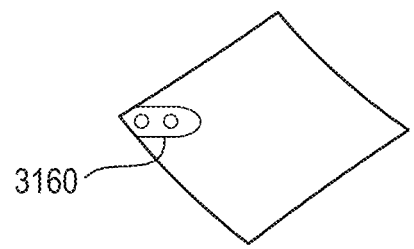

FIG. 64 is an illustration of a side view of a wire frame cell including an attachment feature 3160, such as laser-cut tabs, at a lateral part of the diamond cell that can allow for consistent commissure attachment and valve compressibility, according to an embodiment.

Figure 65:
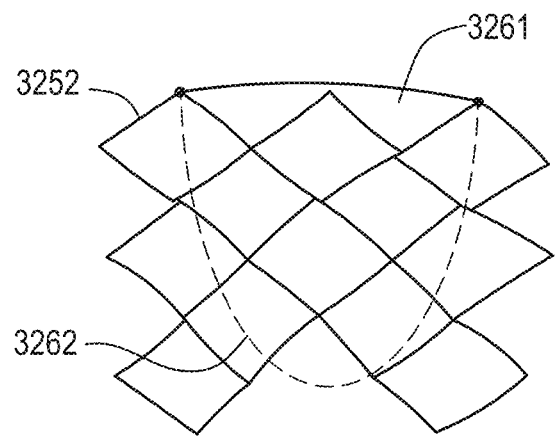
FIGS. 65 and 66 are side views illustrating a portion of a wireframe attached to a leaflet structure according to an embodiment and shown in an expanded configuration and a compressed configuration, respectively.

FIG. 65 is an illustration of a side view of a section of an inner wireframe 3252 of a flow control component showing that, during an elongation phase of a compressive cycle (e.g., when the valve is in deployed in a heart and subjected to compressive forces), a suture attachment line (e.g., a sewn edge 3262) for mounting a leaflet 3261 on the inner frame 3252 can be tailored to work dynamically with leaflet structure to reduce damage to the prosthetic leaflets during valve delivery, according to an embodiment.

Figure 66:
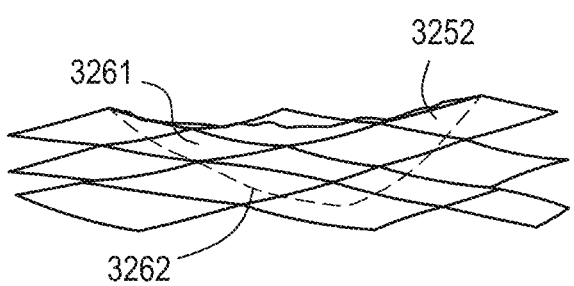

FIG. 66 is an illustration of a side view of a section of the inner wireframe 3252 shown in a compressed configuration that, during a compression phase of a compressive cycle (e.g., when the valve is in deployed in a heart and subjected to compressive forces), the suture attachment line (e.g., the sewn edge 3262) for mounting the leaflet 3261 on the inner frame 3252 can be tailored to work dynamically with leaflet structure to reduce damage to the prosthetic leaflets during valve delivery.

Figure 67:
FIG. 67 is a top view illustration of a free edge of the leaflet structure of FIG. 65 bowing open relative to the wireframe when in the expanded configuration.

FIG. 67 is an illustration of a top view of a leaflet free edge 3363 bowing open during expansion, where the free edge 3363 is not mounted to a portion of an inner wire frame 3352 of a flow control component, according to an embodiment.

Figure 68:
FIG. 68 is a top view illustration of the free edge of the leaflet structure of FIG. 65 laying flat relative to the wireframe when in the compressed configuration.

FIG. 68 is an illustration of a top view of the leaflet free edge 3363 laying flat during compression, where the free edge 3363 is not mounted to a portion of the compressed inner wire frame 3352.

Figure 69:
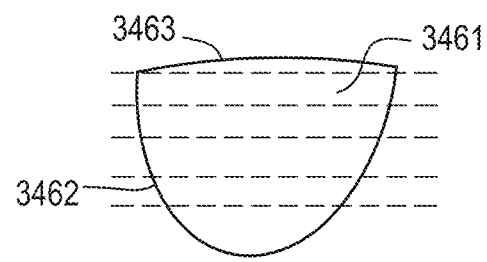
FIG. 69 is a top view illustration of the leaflet structure of FIG. 65 indicating optimization of a leaflet shape at multiple planes.

FIG. 69 is an illustration of a top view of a leaflet 3461 showing that leaflet shape is optimized at multiple planes between a free edge 3463 of the leaflet 3461 and a sewn edge 3462 (e.g., belly portion), and is based on the dynamic foreshortening of an inner wire frame of a flow control component (not shown), according to an embodiment.

Figure 70:
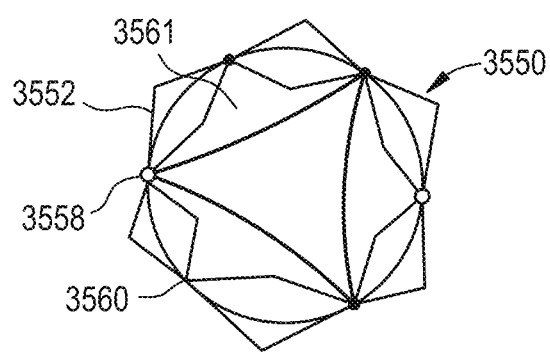
FIGS. 70 and 71 are top views illustrating a flow control component included in a prosthetic valve according to different embodiments.

FIG. 70 is an illustration of a top view of a flow control component 3550 showing locations of commissures 3560 of a set of prosthetic leaflets 3561 attaching to an inner wireframe 3552, which are adjustable to allow for optimized leaflet shape and commissure attachment, according to an embodiment. FIG. 70 also shows one or more hinge areas 3558 as a design element for successful folding the inner wire frame 3552.

Figure 71:
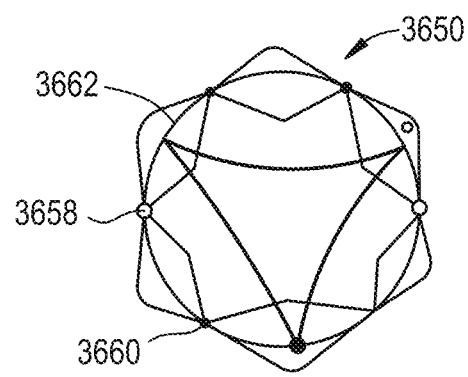

FIG. 71 is another illustration of a top view of a flow control component 3650 showing locations of commissures 3660 of a set of prosthetic leaflets 3661 attaching to an inner wireframe 3652, which are adjustable to allow for optimized leaflet shape and commissure attachment, according to an embodiment. FIG. 71 also shows one or more hinge areas 3658 as a design element for successful folding the inner wire frame 3652.

Figure 72:
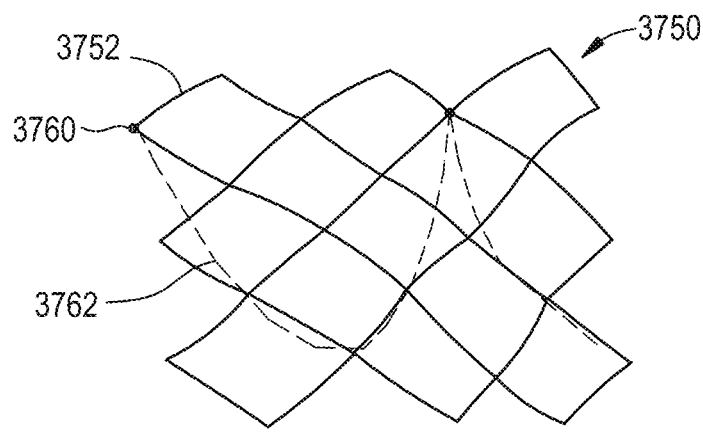
FIG. 72 is a side view illustration of a portion of a flow control component according to an embodiment, and showing adjustable commissure attachment of one or more leaflets to wireframe.

FIG. 72 is an illustration of a side view of a part of a flow control component 3750 showing locations of commissures 3760 of a set of prosthetic leaflets 3761 attaching to an inner wireframe 3752, which are adjustable to allow for optimized leaflet shape and commissure attachment to the inner wireframe 3752, according to an embodiment.

Figure 73:
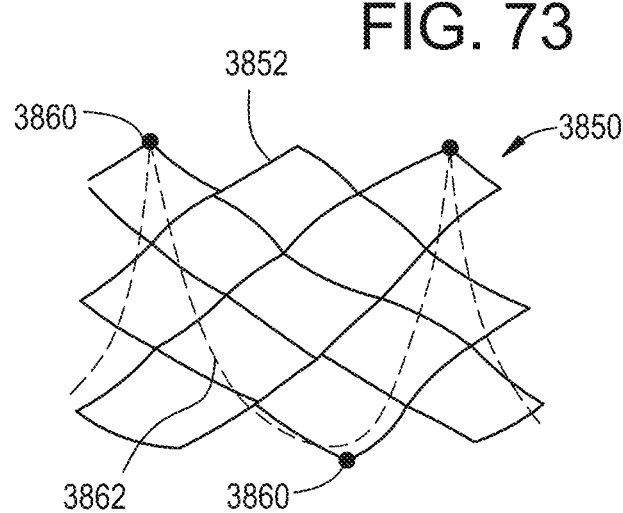
FIG. 73 is a side view illustration of a portion of a flow control component according to an embodiment, and showing adjustable commissure attachment of one or more leaflets to wireframe.

FIG. 73 is another illustration of a side view of a part of a flow control component 3850 showing locations of commissures 3860 of a set of prosthetic leaflets 3761 attaching to an inner wire frame 3852, which are adjustable to allow for optimized leaflet shape and commissure attachment to the inner wireframe 3852, according to an embodiment.

Figure 74:
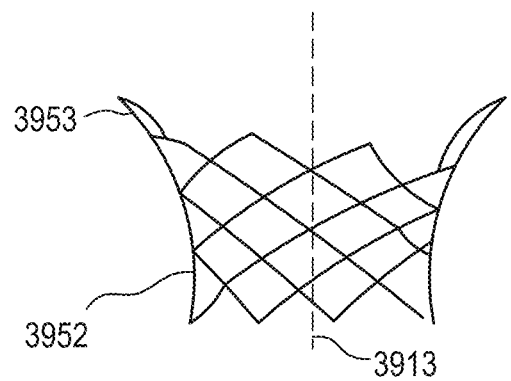
FIG. 74 is a side view illustration of a non-cylindrical inner frame of a flow control component according to an embodiment.

FIG. 74 is an illustration of a side view of an inner frame 3952 of a flow control component having a non-cylindrical configuration according to an embodiment. The inner frame 3952 has a flared cuff-like portion 3953 in an atrial-facing section to allow for better blood flow and smooth transition from an outer frame component of the valve (not shown). Fold line 3913 (e.g., central or vertical axis) shows how the flared embodiment is designed to fold flat for size reduction used for trans-catheter delivery, according to an embodiment.

Figure 75:
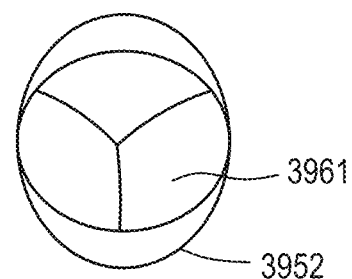
FIG. 75 is a top view illustration of a non-cylindrical flow control component according to an embodiment and showing an inner frame and a set of leaflets mounted therein.

FIG. 75 is an illustration of a top view of the inner frame 3952 showing a set of leaflet cusps 3961 mounted therein.

Figure 76:
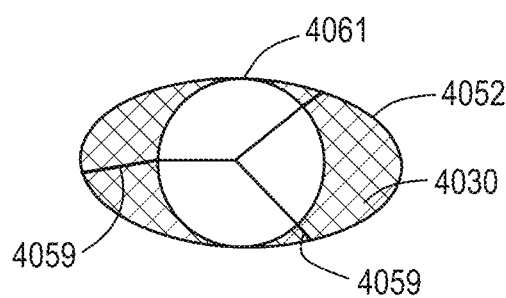
FIG. 76 is a top view illustration of a non-cylindrical flow control component according to and embodiment and showing an inner frame, a set of leaflets mounted therein, and a covered mesh support coupled between the inner frame and the leaflets.

FIG. 76 is an illustration of a top view of an inner frame 4052 of a flow control component having a non-cylindrical configuration according to an embodiment. The inner frame 4052 is shown having an oval shape with a set of leaflet cusps 4061 attached by additional support tabs or structures 4059. The non-leaflet areas of the interior aspect of the inner frame 4052 are filled or covered with a spacer element 4030 such as a biocompatible mesh.

Figure 77:
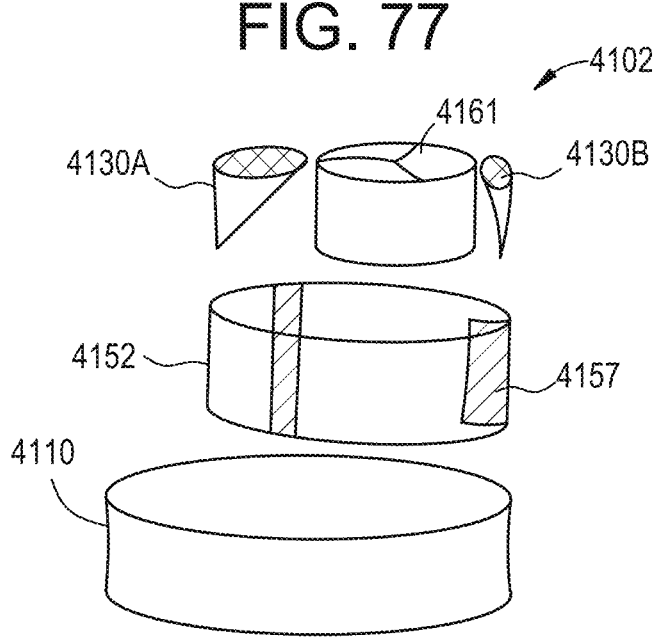
FIG. 77 is a side exploded view illustration of a prosthetic valve having an outer frame and a flow control component with an inner frame, a set of leaflets, and a set of covered mesh supports according to an embodiment.

FIG. 77 is an illustration of a side exploded view of a valve 4102 having an oval outer frame 4110, with a smaller oval inner frame 4152 (e.g., of a flow control component) that has tissue or polymer supports 4157 used to attach to a smaller tissue leaflet component 4161, which is blocked in on opposing sides with spacer elements 4130A and 4130B (e.g., mesh), according to an embodiment.

Figure 78D:
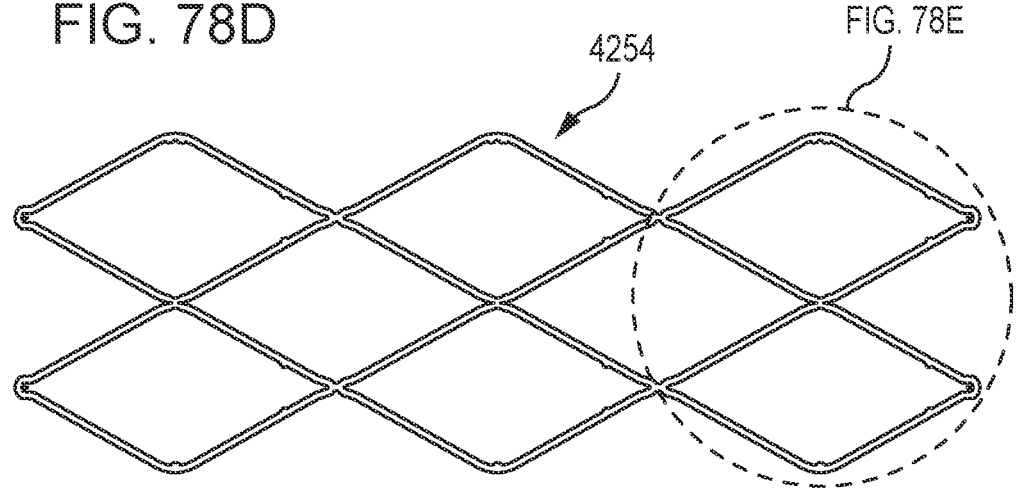
FIG. 78D is a top view of a portion of the inner frame of the flow control component formed by the laser cut workpiece of FIG. 78A.

FIGS. 78A-78F illustrate processes and/or structures for forming at least a portion of an inner frame of a flow control component according to an embodiments. FIG. 78A is a top view of a laser cut workpiece 4255, at least a portion of which can be formed into one or more portions of an inner frame. The laser cut workpiece 4255 can be formed of any suitable biocompatible material. In some implementations, the laser cut workpiece 4255 is formed of a shape-memory alloy such as, for example, Nitinol or the like. The workpiece 4255 can be laser cut to include any suitable feature, shape, opening, etc. Moreover, FIG. 78A shows the laser cut workpiece 4255 prior to further manufacturing configured to draw, stretch, expand, and/or deform the workpiece 4255 into a desired shape. In some embodiments, the laser cut workpiece 4255 can define a series of slits, openings, cuts, etc., which when the workpiece 4255 is further processed, are circumscribed by a wireframe cell, as described in further detail herein.

FIG. 78B is a front view of the laser cut workpiece 4255 that shows the laser cut workpiece 4255 as a relative thin and flat sheet. In other embodiments, the laser cut workpiece 4255 can be any suitable non-flat shape (e.g., the workpiece 4255 can be circular or cylindrical tubing). The laser cut workpiece 4255 can have any suitable thickness such as, for example, about 0.5 mm to about 0.7 mm, about 0.6 mm to about 0.65 mm, about 0.6 mm to about 0.62 mm, or any size or range of sizes therebetween.

FIG. 78C is a detailed top view of the laser cut workpiece 4255 that shows attachment features 4260 cut or formed into the workpiece 4255, which can be used to attach a cover or mesh formed of a biocompatible material to the inner frame. In some embodiments, the attachment features 4260 can be, for example, eyelets or the like that can allow the biocompatible material to be sutured to the inner frame. FIG. 78C further shows alignment tabs 4268 formed by and/or cut into the laser cut workpiece 4255. The alignment tabs 4268 can be configured to allow secure attachment of the biocompatible material to the inner frame and can limit and/or substantially prevent strut-to-strut bypass (e.g., the undesired movement of a first portion of the inner frame relative to a second portion of the inner frame).

FIG. 78D is a front view illustration of the laser cut workpiece 4255 after further manufacturing processes. For example, the workpiece 4255 can be expanded axially (e.g., vertically) to an expanded configuration. FIG. 78D shows that the workpiece 4255 can be radially expanded such that struts, wires, and/or portions of the workpiece 4255 form diamond-shaped wire cells 4254. In some implementations, the workpiece 4255 can be expanded into a wireframe in which the wires or portions of the workpiece 4255 have thickness of about 0.45 mm to about 0.072 mm and a width of about 0.17 mm to about 0.36 mm. In some embodiments, an inner frame can be formed by two separate members that are flexibly coupled to allow the inner frame to elastically deform during folding and/or compression. FIG. 78D shows that a member forming a first portion of the inner frame can include two rows of diamond-shaped cells 4254, each of which includes a set of three diamond-shaped cells 4254. FIG. 78D further shows that the portion or member of the inner frame is permanently deformed, expanded, elongated, stretched, etc. (e.g., via heat setting or the like). That is to say the portion or member of the inner frame is biased into the expanded configuration such that the portion or member stays in the expanded configuration until a force is exerted to cause the portion or member to deform (e.g., fold, compress, and/or the like). The alignment and/or orientation of the diamond-shaped cells can, for example, allow an inner frame of the flow control component to elastically deform in response to the valve being folded (compressed) laterally and/or compressed axially (vertically).

Figure 78E:
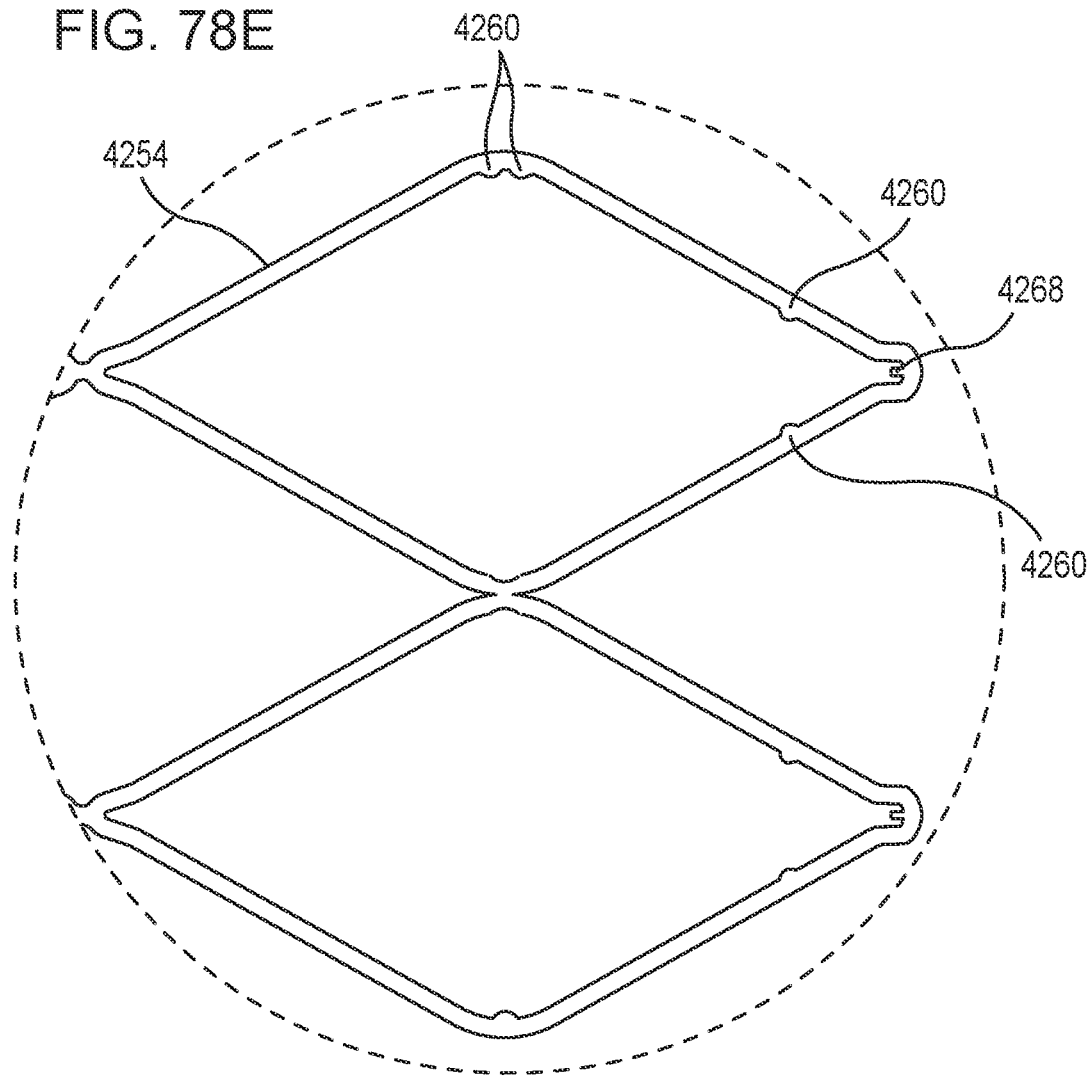
FIG. 78E is an enlarged top view illustration of a portion of the inner frame identified by the circled region in FIG. 78D.

FIG. 78E is a detailed front view illustrating a pair of diamond-shaped cells 4254 that have the attachment features 4260 and the alignment tabs 4268.

Figure 78F:
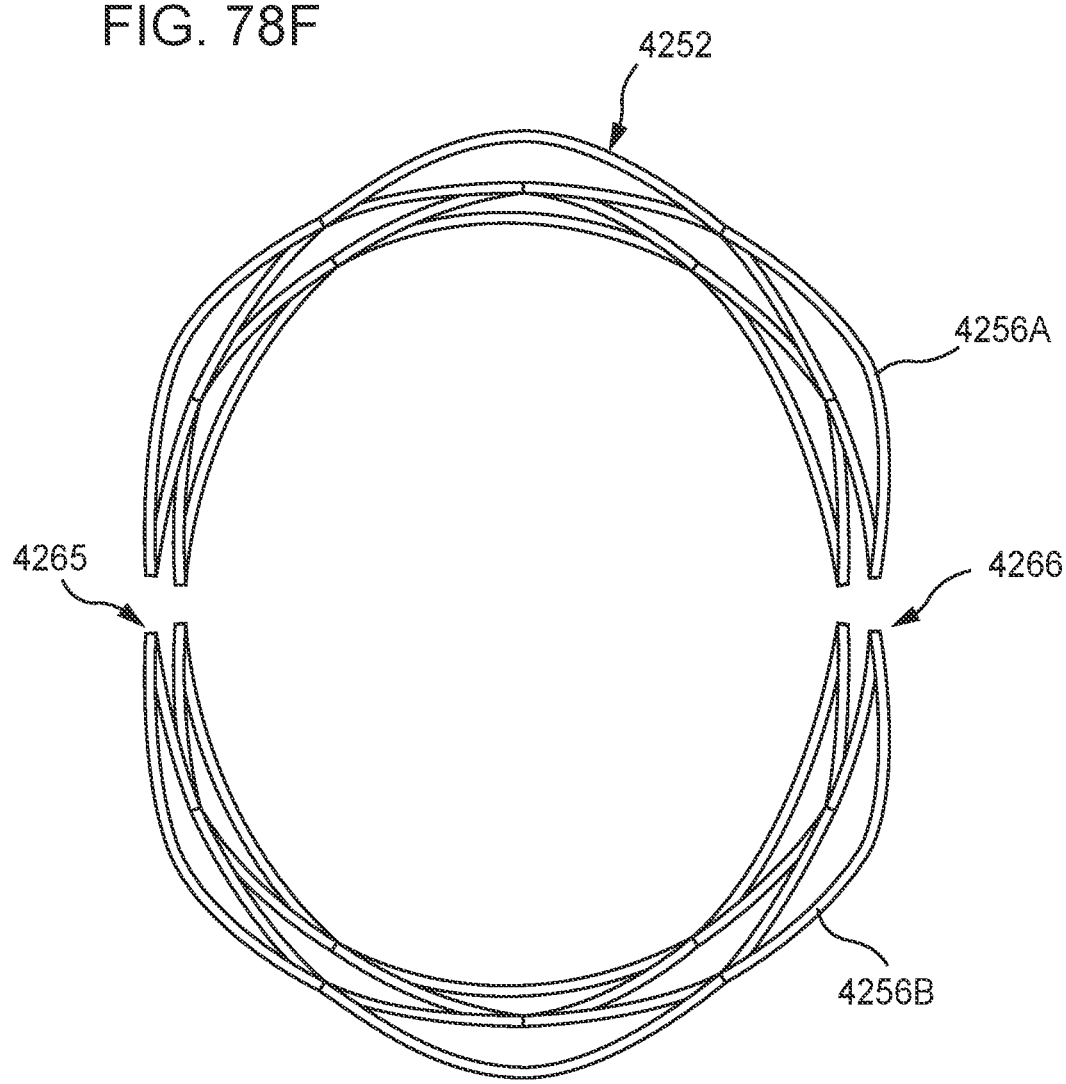
FIG. 78F is a top view of a portion of the inner frame of the flow control component having a first member and a second member that can be flexibly coupled to form the inner frame.

FIG. 78F is a top view illustration of the inner frame 4252 that includes a first member 4256A and a second member 4256B that can be coupled at a proximal lateral connection point 4265 and a distal lateral connection point 4266 (e.g., fold areas, coupling portions, edge connection points, etc.). The first member 4256A and the second member 4256B are bent into a final shape that is semi-circular, arcuate, curved, elliptical, and/or the like. In some embodiments, the combined (or coupled) first member 4256A and second member 4256B can have a substantially cylindrical shape. In some embodiments, the substantially cylindrical shape can have an inner diameter of about 20 mm to about 30 mm, about 22 mm to about 29 mm, about 24 mm to about 28 mm, about 26 mm to about 27 mm. In some embodiments, the inner diameter is about 27 mm. Although not shown in FIG. 78E, the first member 4256A can be coupled to the second member 4256B at the connection points 4265 and 4266 via any suitable coupling methods such as, for example, a fabric hinge, a number of sutures, and/or any other suitable flexible coupling. The flexible coupling of the first member 4256A to the second member 4256B and the arrangement and/or orientation of the diamond-shaped cells can allow the inner frame to elastically deform when the valve in which it is disposed is folded and/or compressed.

Figure 79:
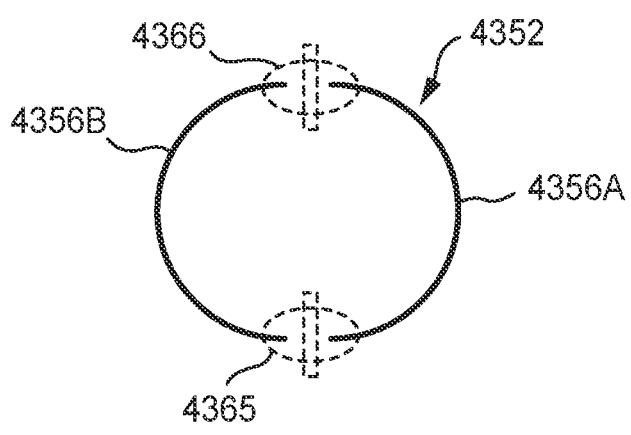
FIGS. 79 and 80 are top view illustration and a side view illustration, respectively, of a portion of an inner frame of a flow control component showing ways to couple end portions thereof, according to an embodiment.
Figure 80:
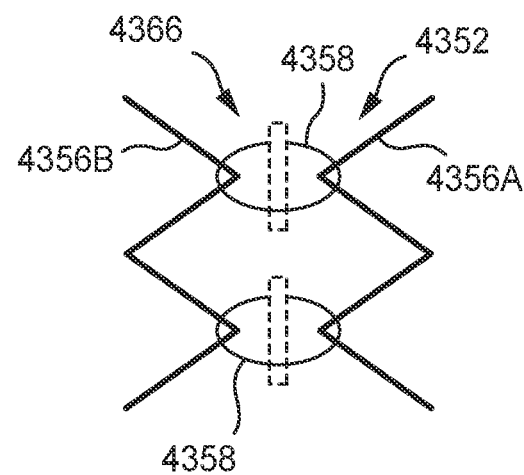

FIGS. 79 and 80 illustrate at least a portion of an inner frame 4352 of a flow control component and show a way to couple end portions thereof, according to an embodiment. FIG. 79 is an illustration of a top view of the inner frame 4352 and shows a first member 4356A and a second member 4356B coupled together at lateral connection points 4365 and 4366. FIG. 80 is an illustration of a distal side view of the inner frame 4352 showing an edge or end portion of the first member 4356A flexibly coupled to an edge or end portion of the second member 4356B and the distal lateral connection point 4366. FIG. 80 further shows that the first member 4356A is coupled to the second member 4356B via a pair of hinge connections 4358. In some embodiments, the hinge connections 4358 can be sutures, fabric, molded polymer components, and/or the like. Sutures, for example, can form loops and/or knots to secure the two members 4356A and 4356B. In some embodiments, fabric can be used as a buffer between the end portion of the members 4356A and 4356B to allow the hinge connections 4358 to roll and/or otherwise not bind. The fabric can further protect the end portions of the members 4356A and 4356B, can hold the hinge connection 4358 in a desired position, and/or can prevent slippage. Moreover, the hinge connections 4358 can allow the inner frame 4352 to elastically deform in response to being folded and/or compressed.

Figure 81A:
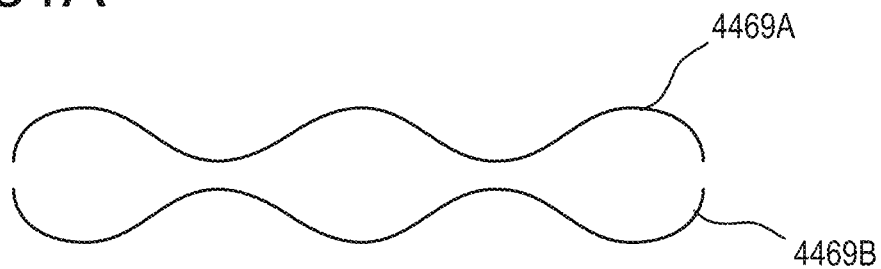
FIG. 81A is a front view illustration of a pair of wires configured to form a portion of an inner frame of a flow control component according to an embodiment.

FIG. 81A is an illustration of a front view of a pair of curved wires 4469A and 4469B that can be coupled to form a row of wire cells of an inner frame of a flow control component, according to an embodiment.

Figure 81B:
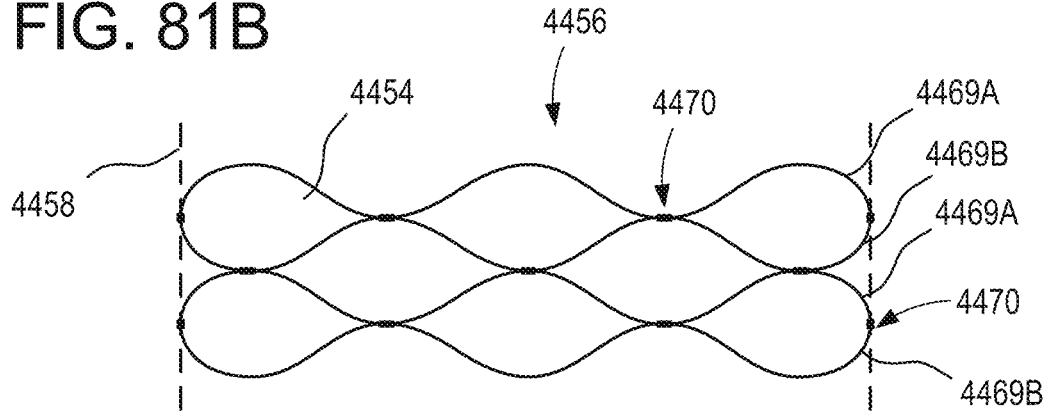
FIG. 81B is a portion of the inner frame formed by laser welding wires shown in FIG. 81A.

FIG. 81B is an illustration of a front view of a set of the curved wires 4469A and 4469B coupled together to form a member or side 4456 of an inner frame. The curved wires 4469A and 4469B can be laser welded at any number of weld points 4470 to form a number of wire cells. FIG. 81B shows the curved wires 4469A and 4469B being coupled (welded) into two rows of three wire cells. The member or side 4456 of the inner frame can be flexibly coupled to a second member or side (not shown) at lateral connection points or hinge areas 4458.

Figure 82A:
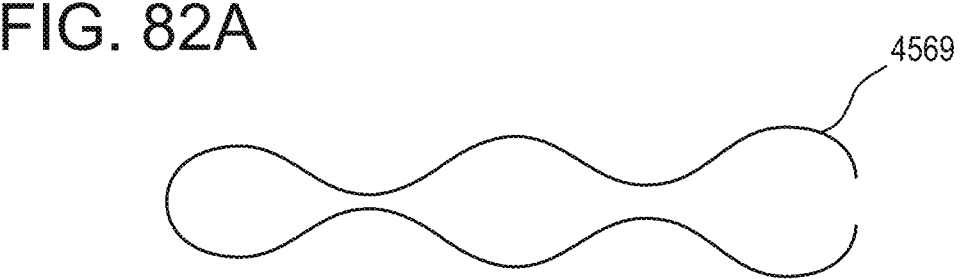
FIG. 82A is a front view illustration of a wire configured to form a portion of an inner frame of a flow control component according to an embodiment.

FIG. 82A is an illustration of a front view of a single curved wire 4569 that can be coupled (e.g., to itself at desired locations) to form a row of wire cells of an inner frame of a flow control component, according to an embodiment.

Figure 82B:
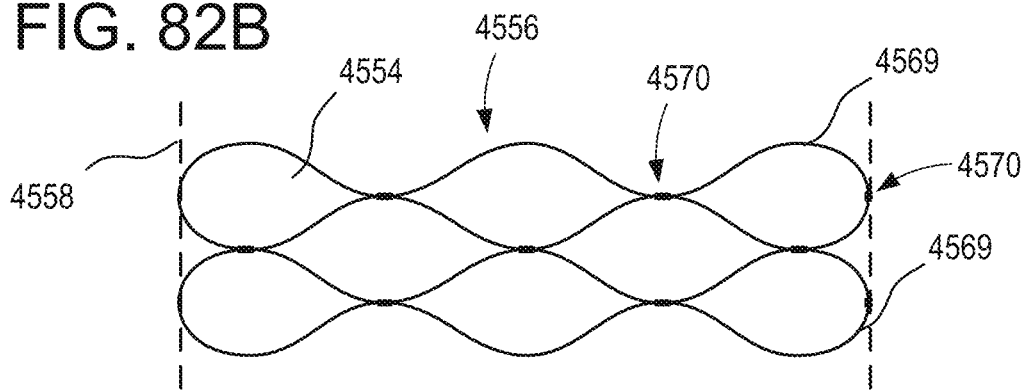
FIG. 82B is a portion of the inner frame formed by laser welding the wire shown in FIG. 82A.

FIG. 82B is an illustration of a front view of two separate curved wires 4569 that are coupled together to form a member or side 4556 of an inner frame. The curved wires 4569 are laser welded at any number of weld points 4570 to form a number of wire cells. FIG. 82B shows the curved wires 4569 being coupled (welded) into two rows of three wire cells. The member or side 4556 of the inner frame can be flexibly coupled to a second member or side (not shown) at lateral connection points or hinge areas 4558.

Figure 83:
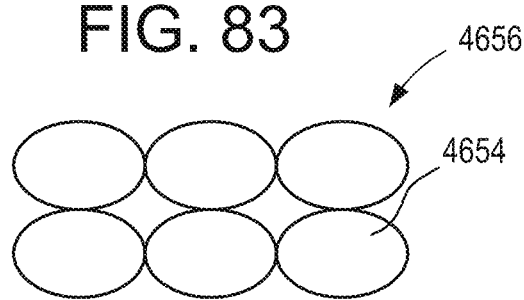
FIGS. 83-85 are front view illustrations of a portion of an inner frame of a flow control component according to various embodiments.

FIG. 83 is an illustration of a front view of a member or side 4656 of an inner frame according to an embodiment. FIG. 83 shows that the member or side 4656 of the inner frame can be formed and/or include a number or round, curved, circular, and/or elliptical wire cells 4654. The member or side 4656 includes two rows with three wire cells 4654 per row.

Figure 84:
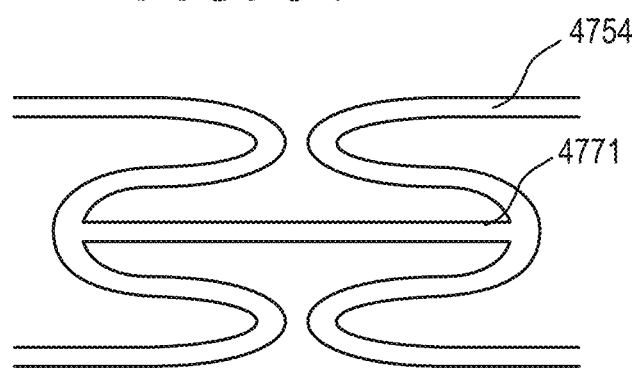

FIG. 84 is an illustration of a front view of a portion of a member or side of an inner frame according to an embodiment. FIG. 84 shows that the member or side can include curved wire cells 4754 that are separated via a spacer 4771 that connects two adjacent wire cells 4754.

Figure 85:
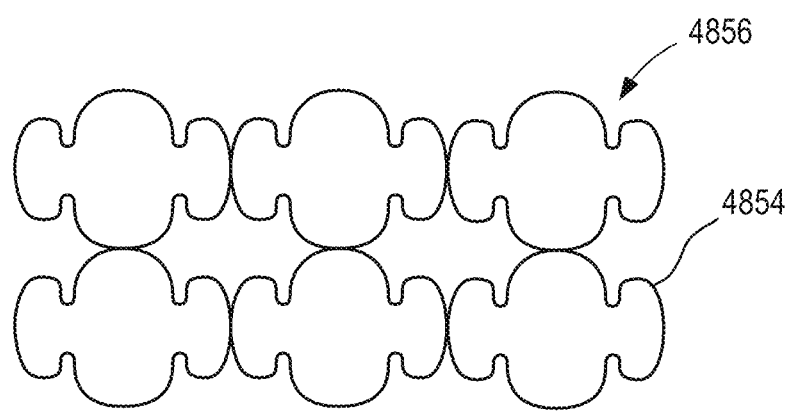

FIG. 85 is an illustration of a front view of a portion of a member or side 4856 of an inner frame according to an embodiment. FIG. 85 shows that the member or side 4856 can include wire cells 4854 that have a curved but irregular shape. In some embodiments, the irregular shape of the wire cells 4854 can be configured to distribute stress and/or strain during folding and/or compression. The member or side 4856 includes two rows with three wire cells 4854 per row.

Figure 86:
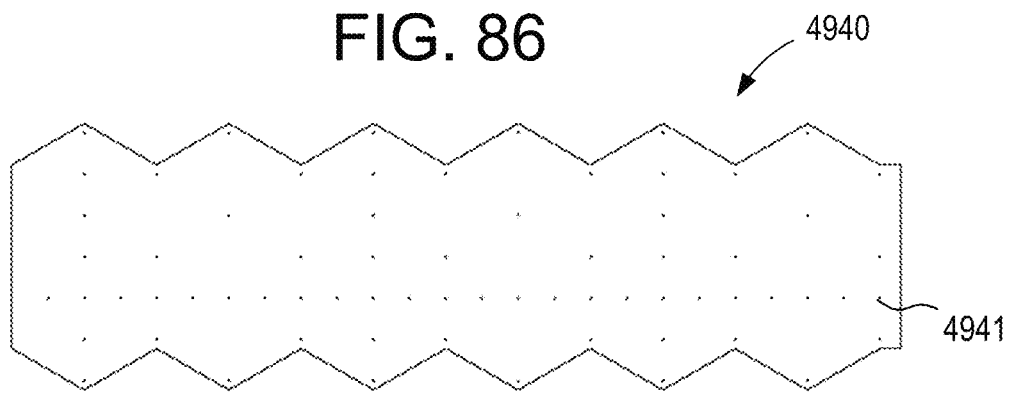
FIGS. 86-88 are front view illustrations of a biocompatible material configured to be coupled to an inner frame of a flow control component according to various embodiments.

FIG. 86 is an illustration of a front view of a biocompatible cover 4940 configured to be coupled to an inner frame of a flow control component according to an embodiment. The biocompatible cover 4940 can be formed from and/or can include pericardial tissue and/or the like. The biocompatible cover 4940 is optimized to match and/or couple to the inner frame. The shape of the cover 4940 provides adequate frame cell coverage while minimizing amount of tissue. An overlap seam facilitates manufacturing allowing a portion of the cover 4940 to be folded over and sewn at the edges to form a cylinder. The cover 4940 includes a pattern of openings 4941 and/or markings that can facilitate attachment of the cover 4940 to the inner frame. The biocompatible cover 4940 can be coupled to an inner surface of the inner frame. In some implementations, the biocompatible cover 4940 can have an axial size (e.g., a height or vertical extent) that is greater than an axial size of the inner frame, allowing a portion of the biocompatible cover 4940 to be folded over a top and bottom edge of the inner frame.

Figure 87:
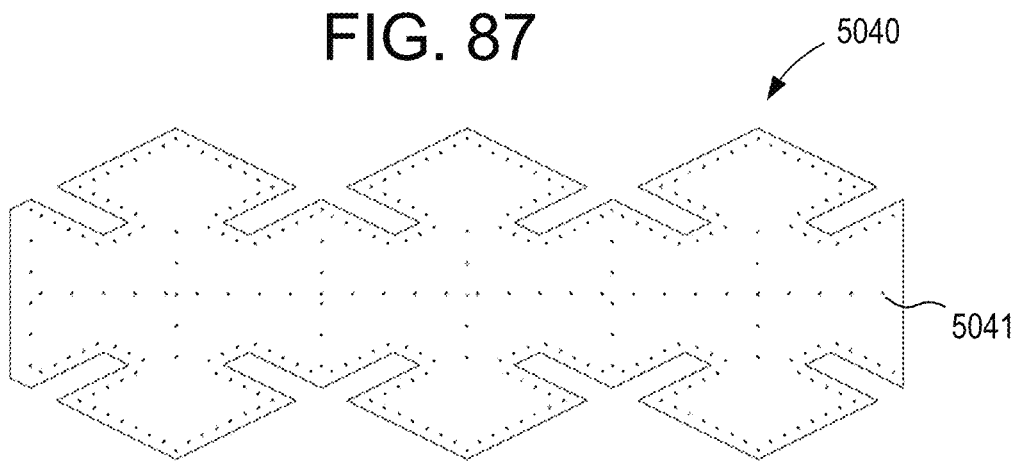

FIG. 87 is an illustration of a front view of a biocompatible cover 5040 configured to be coupled to an inner frame of a flow control component according to an embodiment. The biocompatible cover 5040 can be formed from and/or can include pericardial tissue and/or the like. The biocompatible cover 5040 is optimized to match and/or couple to the inner frame. The shape of the cover 5040 provides adequate frame cell coverage while minimizing amount of tissue. An overlap seam facilitates manufacturing allowing a portion of the cover 5040 to be folded over and sewn at the edges to form a cylinder. The cover 5040 includes a pattern of openings 5041 and/or markings that can facilitate attachment of the cover 5040 to the inner frame.

Figure 88:
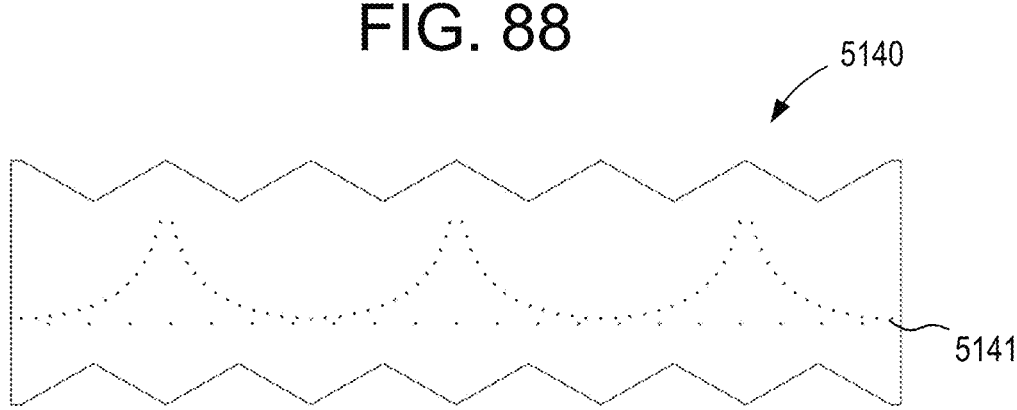

FIG. 88 is an illustration of a front view of a biocompatible cover 5140 configured to be coupled to an inner frame of a flow control component according to an embodiment. The biocompatible cover 5140 can be formed from and/or can include pericardial tissue and/or the like. The biocompatible cover 5140 is optimized to match and/or couple to the inner frame. The shape of the cover 5140 provides adequate frame cell coverage while minimizing amount of tissue. An overlap seam facilitates manufacturing allowing a portion of the cover 5140 to be folded over and sewn at the edges to form a cylinder. The cover 5140 includes a pattern of openings and/or markings 5141 that can facilitate attachment of the cover 5140 to the inner frame.

Figure 89:
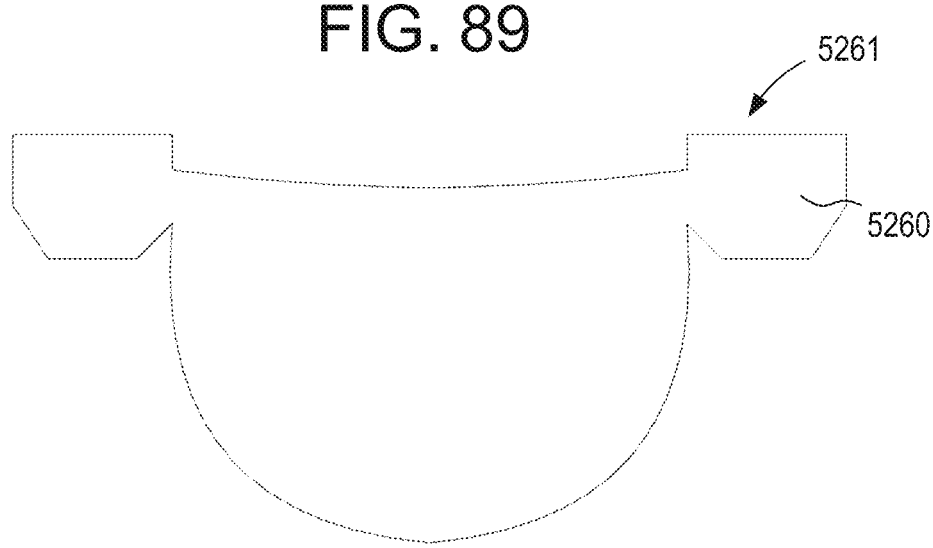
FIGS. 89-93 are front view illustrations of a biocompatible material configured to be formed into a leaflet of a flow control component according to various embodiments.

FIG. 89 is an illustration of a front view of a leaflet 5261 configured to be coupled to an inner frame of a flow control component according to an embodiment. The leaflet 5261 can be formed from a biocompatible material such as pericardial tissue and/or the like. The leaflet 5261 and/or a belly or middle portion thereof is optimized to allow for orthogonal compression, to minimize leaflet stress for increased durability, and/or the like. The leaflet 5261 can be sized and/or shaped to match and/or couple to the inner frame. The leaflet 5261 can have an upper portion that includes a pair of commissure attachments 5260 used to couple the leaflet 5261 to the inner frame. In some embodiments, the upper portion of the leaflet 5261 can be optimized for a desired opening during forward fluid flow, a desired closing and/or coaptation during backward fluid flow, a desired compliance to increase commissure durability, a handling a relatively high stress region within the leaflet 5261.

Figure 90:
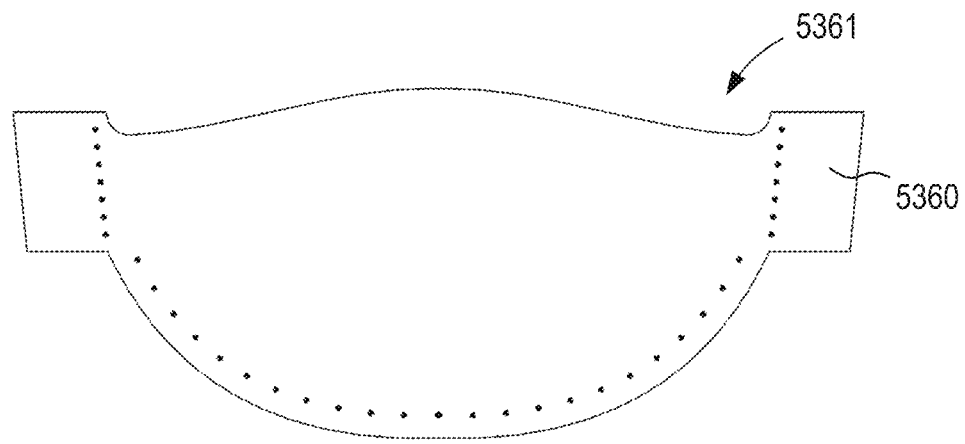

FIG. 90 is an illustration of a front view of a leaflet 5361 configured to be coupled to an inner frame of a flow control component according to an embodiment. The leaflet 5361 can be formed from a biocompatible material such as pericardial tissue and/or the like. The leaflet 5361 and/or a belly or middle portion thereof is optimized to allow for orthogonal compression, to minimize leaflet stress for increased durability, and/or the like. The leaflet 5361 can be sized and/or shaped to match and/or couple to the inner frame. The leaflet 5361 can have an upper portion that includes a pair of commissure attachments 5360 used to couple the leaflet 5361 to the inner frame. In some embodiments, the upper portion of the leaflet 5361 can be optimized for a desired opening during forward fluid flow, a desired closing and/or coaptation during backward fluid flow, a desired compliance to increase commissure durability, a handling a relatively high stress region within the leaflet 5361. The leaflet 5361 includes a pattern of openings and/or markings that can facilitate attachment of the leaflet 5361 to the inner frame.

Figure 91:
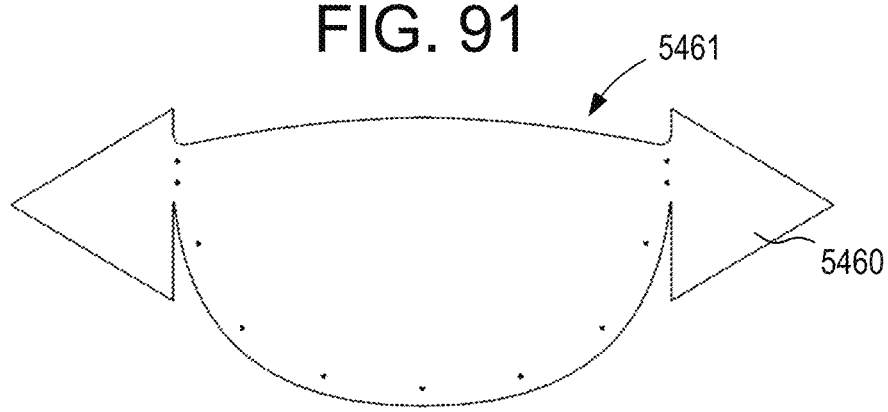

FIG. 91 is an illustration of a front view of a leaflet 5461 configured to be coupled to an inner frame of a flow control component according to an embodiment. The leaflet 5461 can be formed from a biocompatible material such as pericardial tissue and/or the like. The leaflet 5461 and/or a belly or middle portion thereof is optimized to allow for orthogonal compression, to minimize leaflet stress for increased durability, and/or the like. The leaflet 5461 can be sized and/or shaped to match and/or couple to the inner frame. The leaflet 5461 can have an upper portion that includes a pair of commissure attachments 5460 used to couple the leaflet 5461 to the inner frame. In some embodiments, the upper portion of the leaflet 5461 can be optimized for a desired opening during forward fluid flow, a desired closing and/or coaptation during backward fluid flow, a desired compliance to increase commissure durability, a handling a relatively high stress region within the leaflet 5461. The leaflet 5461 includes a pattern of openings and/or markings that can facilitate attachment of the leaflet 5461 to the inner frame.

Figure 92:
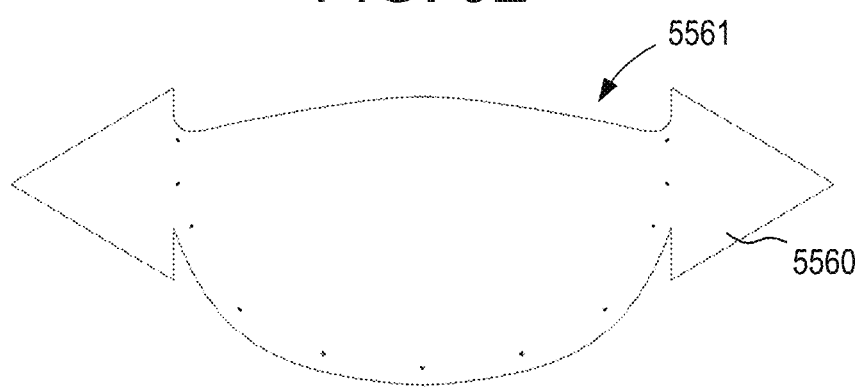

FIG. 92 is an illustration of a front view of a leaflet 5561 configured to be coupled to an inner frame of a flow control component according to an embodiment. The leaflet 5561 can be formed from a biocompatible material such as pericardial tissue and/or the like. The leaflet 5561 and/or a belly or middle portion thereof is optimized to allow for orthogonal compression, to minimize leaflet stress for increased durability, and/or the like. The leaflet 5561 can be sized and/or shaped to match and/or couple to the inner frame. The leaflet 5561 can have an upper portion that includes a pair of commissure attachments 5560 used to couple the leaflet 5561 to the inner frame. In some embodiments, the upper portion of the leaflet 5561 can be optimized for a desired opening during forward fluid flow, a desired closing and/or coaptation during backward fluid flow, a desired compliance to increase commissure durability, a handling a relatively high stress region within the leaflet 5561. The leaflet 5561 includes a pattern of openings and/or markings that can facilitate attachment of the leaflet 5561 to the inner frame.

Figure 93:
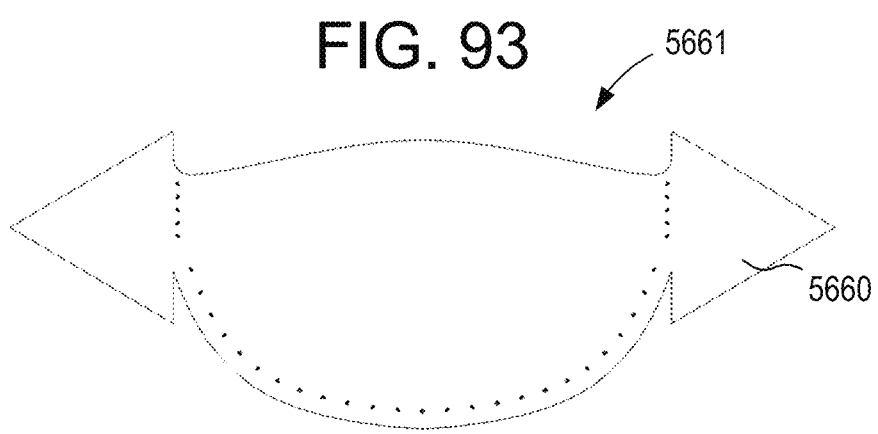

FIG. 93 is an illustration of a front view of a leaflet 5661 configured to be coupled to an inner frame of a flow control component according to an embodiment. The leaflet 5661 can be formed from a biocompatible material such as pericardial tissue and/or the like. The leaflet 5661 and/or a belly or middle portion thereof is optimized to allow for orthogonal compression, to minimize leaflet stress for increased durability, and/or the like. The leaflet 5661 can be sized and/or shaped to match and/or couple to the inner frame. The leaflet 5661 can have an upper portion that includes a pair of commissure attachments 5660 used to couple the leaflet 5661 to the inner frame. In some embodiments, the upper portion of the leaflet 5661 can be optimized for a desired opening during forward fluid flow, a desired closing and/or coaptation during backward fluid flow, a desired compliance to increase commissure durability, a handling a relatively high stress region within the leaflet 5661. The leaflet 5661 includes a pattern of openings and/or markings that can facilitate attachment of the leaflet 5661 to the inner frame.

Figure 94:
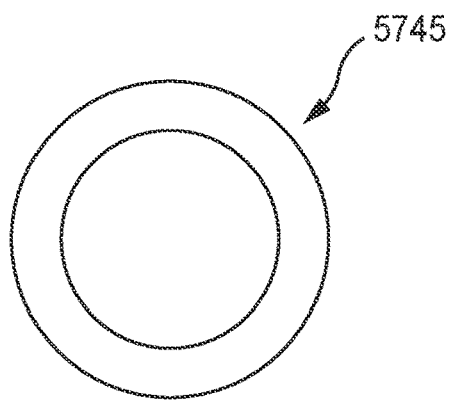
FIG. 94 is a top view schematic illustration of a band used to facilitate the coupling of a flow control component to an outer frame of a prosthetic valve according to an embodiment.

FIG. 94 is a schematic illustration of a top view of a coupling band 5745 configured to facilitate a coupling of an inner frame to an outer frame of a prosthetic valve according to an embodiment. The coupling band 5745 can be formed from a biocompatible material such as, for example, pericardial tissue. The coupling band 5745 can be attached to the inner frame and/or sewn onto a biocompatible cover coupled to the inner frame. In some implementations, the coupling band 5745 can provide a band, flange, and/or structure that can be coupled to an outer frame and/or a portion of the outer frame via sutures and/or otherwise sewn into place. In some implementations, the coupling band 5745 can be coupled to a drum, cover, and/or spacer extending over a portion of a central channel of the outer frame. A spacer or cover can be similar to, for example, the spacer 230 and/or any of the spacers included in any of the other embodiments.

Figure 95A:
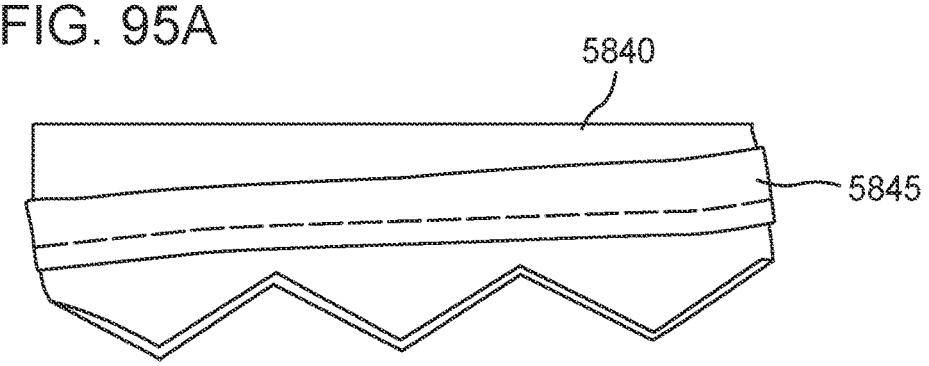
FIG. 95A is a front view illustration of a biocompatible material prior to being coupled to an inner frame according to an embodiment.

FIG. 95A is an illustration of a front view of a biocompatible cover 5840 that includes and/or that is coupled to a coupling band 5845 configured to facilitate a coupling of an inner frame to an outer frame of a prosthetic valve according to an embodiment. The coupling band 5845 is shown as being sewn onto the biocompatible cover 5840. The coupling band 5845 and the biocompatible cover 5840 can be formed from, for example, pericardial tissue and/or any other suitable biocompatible material described herein.

Figure 95B:
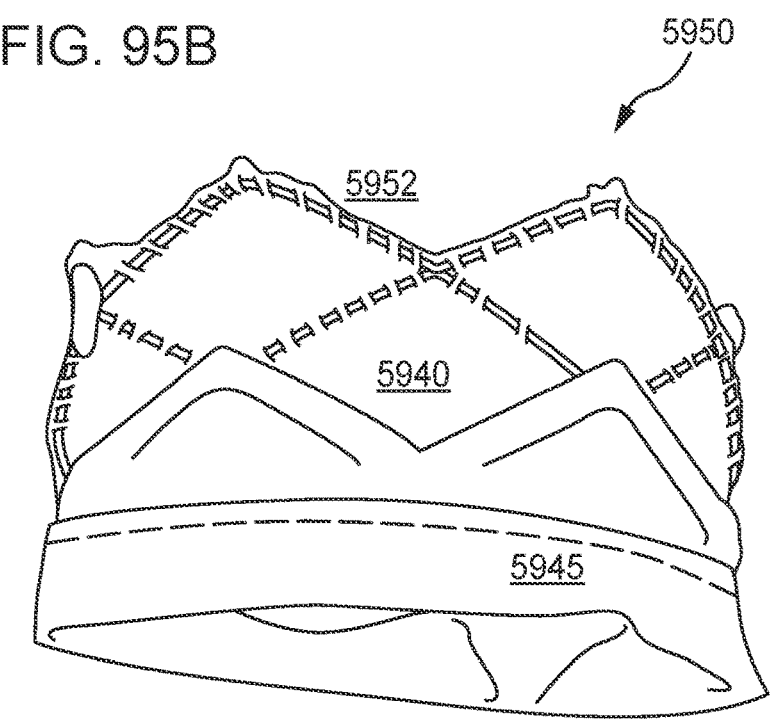
FIG. 95B is a front view illustration of a flow control component including a biocompatible material coupled to an inner frame according to an embodiment.

FIG. 95B is an illustration of a front perspective view of a flow control component 5950 according to an embodiment. The flow control component 5950 is shown as including an inner frame 5952 with a biocompatible cover 5940 coupled to (e.g., sewn on to) the inner frame 5952. A coupling band 5945 is shown coupled to the biocompatible cover 5940 and/or the inner frame. The coupling band 5945 and the biocompatible cover 5940 can be formed from, for example, pericardial tissue and/or any other suitable biocompatible material described herein.

Figure 96:
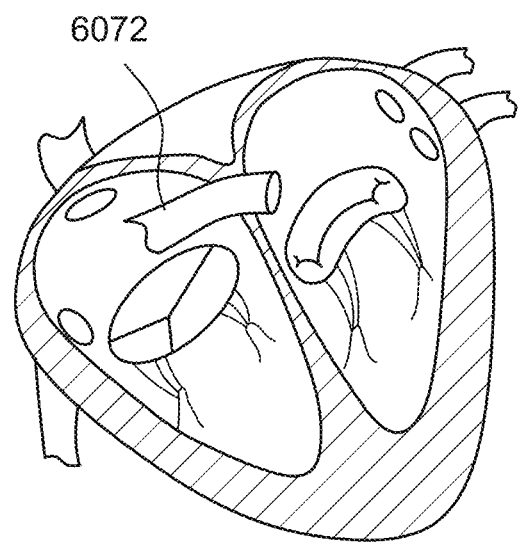
FIG. 96 is a cut-away side view illustration of a human heart having a trans-septal (trans-femoral/inferior vena cava (IVC) or superior vena cava (SVC)) delivery catheter crossing from the right atrium to the left atrium for accessing a mitral valve of the heart.
Figure 97:
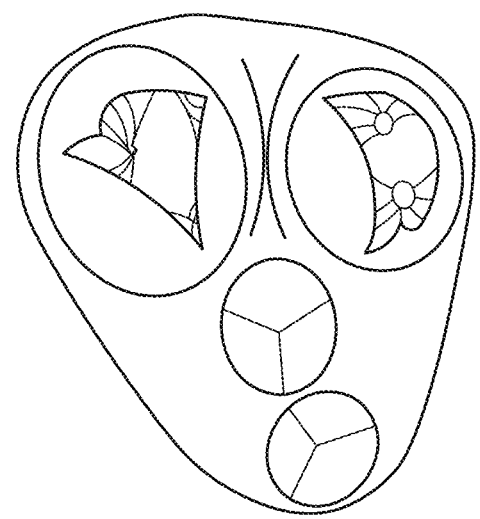
FIG. 97 is a cross-sectional view illustration of the human heart of FIG. 96 showing the relative locations of the mitral valve, the tricuspid valve, the aortic valve, and the pulmonary valve.

FIGS. 96-102 illustrate a process of delivering a side-deliverable transcatheter prosthetic heart valve to a native annulus of a human heart, according to an embodiment. FIG. 96 is a cut-away illustration of a side view of a human heart having a trans-septal (trans-femoral/IVC or SVC) delivery catheter 6072 crossing from the right atrium to the left atrium for access to the mitral valve. FIG. 97 is an illustration of a cross-sectional view of the human heart showing the relative locations of the mitral valve, the tricuspid valve, the aortic valve, and the pulmonary valve.

Figure 98:
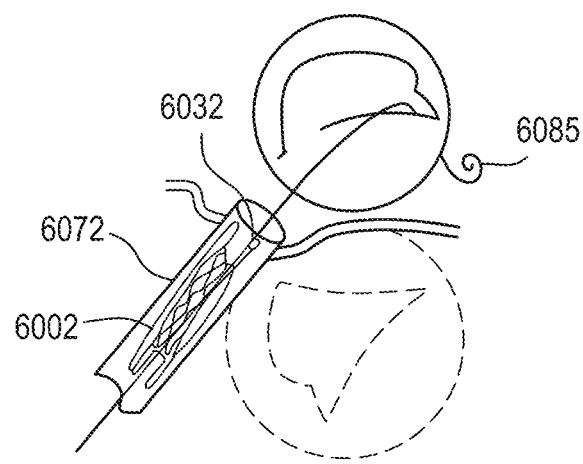
FIGS. 98-102 are various views illustrating a process of delivering a prosthetic valve into the annulus of a native valve of the human heart shown in FIGS. 96 and 97.

FIG. 98 is an illustration of a top view of a valve and shows a guide wire 6085 directing a replacement valve 6002 to a leaflet with the valve 6002 in a compressed intra-catheter configuration (e.g., disposed in the delivery catheter 6072). A distal anchoring element 6032 of a valve frame 6010 is shown with guide wire 6085 threaded through the end of the distal anchoring element 6032, to guide the distal anchoring element 6032 over and/or along the guide wire 6085, and lead the valve 6002 into the correct deployment location.

Figure 99:
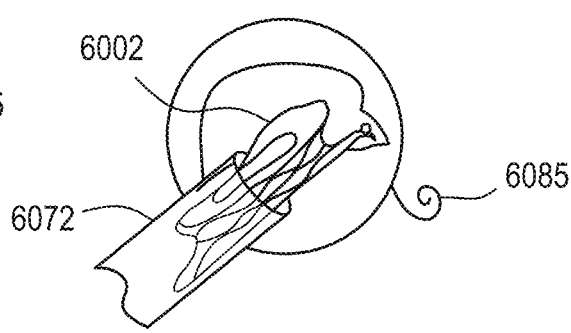

FIG. 99 is an illustration of a top view of a valve (e.g., the mitral valve) and the prosthetic valve 6002 that shows, when the guide wire 6085 is pre-positioned into a desired location, the distal anchoring element 6032 is fed over the guide wire 6085 leading the valve 6002 into the correct deployment location. The valve 6002 is shown in a partial deployment configuration being partially released from the delivery catheter 6072.

Figure 100:
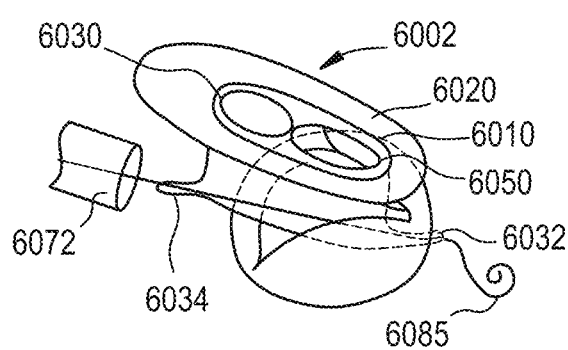

FIG. 100 is an illustration of a top perspective view of the prosthetic valve 6002 that shows the valve 6002 in an expanded configuration. The valve 6002 is shown having an atrial collar 6020, the outer valve frame 6010, an inner flow control component 6050 with an inner frame and a set of leaflets mounted thereto, and a spacer element 6030. The distal anchoring element 6032 is shown with the guidewire 6085 threaded through an end of the distal anchoring element 6032 such that when the guidewire 6085 is pre-positioned into the desired location, the distal anchoring element 6032 is fed over the guide wire 6085 leading the valve 6002 into the correct deployment location. The valve 6002 is shown fully released from delivery catheter 6072 and positioned temporarily at an upwards angle with the distal anchoring tab 6032 in the desired area (e.g., an anterior area), and a proximal anchoring element 6034 (e.g., an anterior anchoring element) above the valve. This angled positioning avoids a pop-off effect and allows for the new prosthetic valve 6002 to engage the blood flow while the native valve continues to operate, just prior to the proximal side being inserted into place with the proximal anchoring element 6034 anchoring the proximal side of the valve 6002, for a non-traumatic transition from native valve to prosthetic valve 6002.

Figure 101:
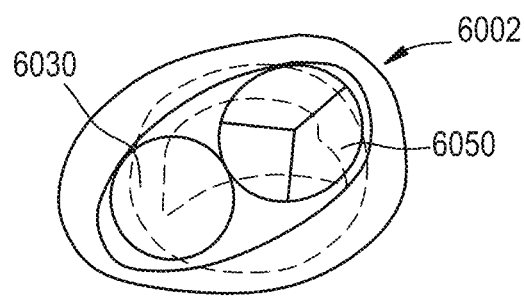
Figure 102:
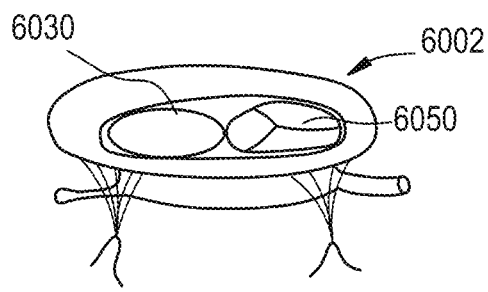

FIG. 101 is an illustration of a top view of the prosthetic valve 6002 deployed in the native annulus (visible in dashed line). FIG. 102 is an illustration of a side perspective view of the prosthetic valve 6002 deployed in the native annulus (not visible), according to an embodiment.

Figure 103:
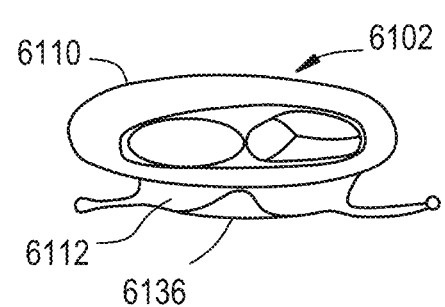
FIG. 103 is a side perspective view illustration of a prosthetic valve having an A2 clip integrated into a sidewall of an outer frame according to an embodiment.
Figure 104A:
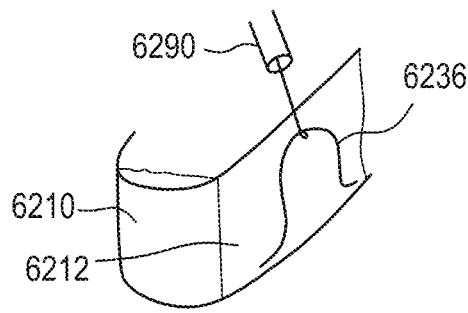
FIGS. 104A-104D are top perspective views illustrating a portion of a prosthetic valve and a process of capturing a native A2 leaflet via an A2 clip of the prosthetic valve, according to an embodiment.
Figure 104B:
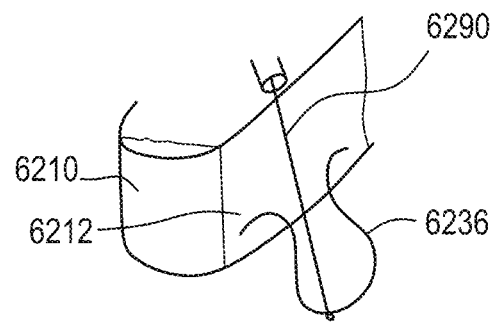
Figure 104C:
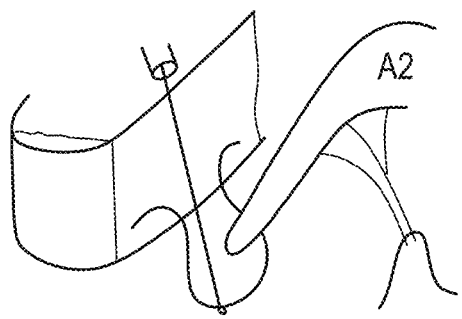
Figure 104D:
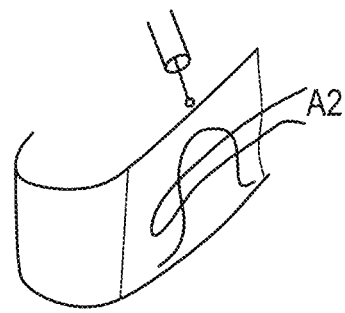

FIG. 103 is an illustration of a side perspective view of an embodiment of a prosthetic valve 6102 that has an anterior clip 6136 integrated into an A2 facing side of a transannular section 6112 of an outer frame 6110 of the valve 6102, according to an embodiment.

FIGS. 104A-104D are illustrations of a top perspective close-up view of a sequence showing an anterior clip 6236 coupled to a transannular section 6212 of a valve frame 6210 being actuated from a stowed position against an anterior facing side of the transannular section 6212 (FIG. 104A), to an open tab-capture position by extending the anterior clip 6236 via a positioning tool 6290 (FIG. 104B), to an open configuration with an anterior leaflet in a capture range-position (FIG. 104C), and to a closed position with the anterior leaflet captured between the anterior clip 6236 and the anterior facing side of the transannular section 6212 of the valve frame 6210, according to an embodiment.

Figure 105:
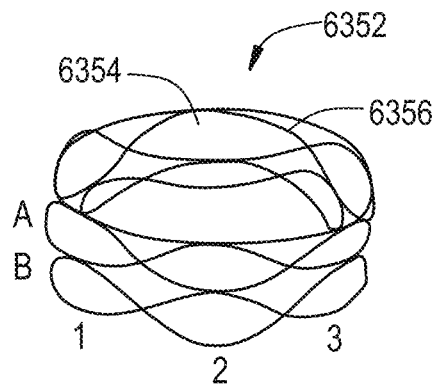
FIG. 105 is a side perspective view illustration of an inner frame of a flow control component according to an embodiment.

FIG. 105 is an illustration of a side perspective view of an inner wire frame 6352 of a flow control component that shows 3 cells 6354 per side in two rows for a total of six cells 6354 per side and twelve (12) cells 6354 total as a frame for mounting three (3) leaflet cusps, according to an embodiment.

Figure 106:
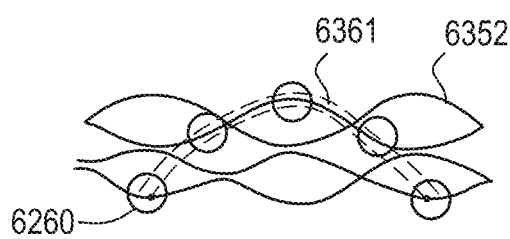
FIG. 106 is a side view illustration of a portion of the inner frame of FIG. 105 and showing a set of leaflet attachment points for attaching a leaflet structure thereto.

FIG. 106 is an illustration of a detailed side view of a portion of the inner wire frame 6352 during diastole (leaflet opening) showing how leaflet tissue 6361 is sutured and leaflet-frame attachment or connection points 6360 are positioned during (lateral) cell expansion.

Figure 107:
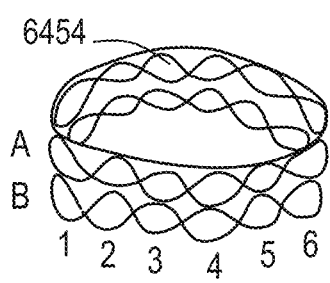
FIG. 107 is a side perspective view illustration of an inner frame of a flow control component according to an embodiment.

FIG. 107 is an illustration of a side perspective view of an inner wire frame 6452 of a flow control component that shows 6 cells 6454 per side in two rows for a total of twelve cells 6454 per side and twenty-four (24) cells 6454 total as a frame for mounting three (3) leaflet cusps, according to an embodiment.

Figure 108:
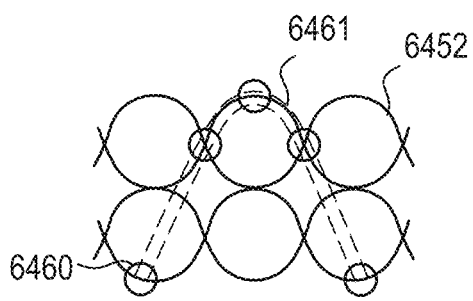
FIG. 108 is a side view illustration of a portion of the inner frame of FIG. 107 and showing a set of leaflet attachment points for attaching a leaflet structure thereto.

FIG. 108 is an illustration of a detailed side view of a portion of the inner wire frame 6452 during systole (leaflet closing) showing how leaflet tissue 6461 is sutured and leaflet-frame attachment or connection points 6460 are positioned during cell contraction. Such an arrangement of the cells 6454 can reduce leaflet failure at known failure points such as commissure connection points 6460.

Figure 109:
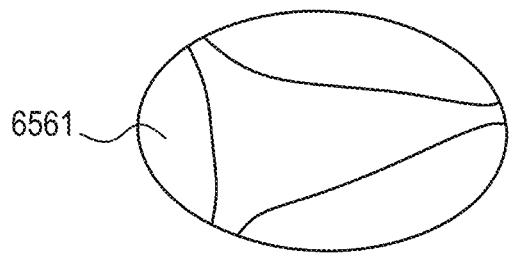
FIGS. 109 and 110 are top views illustrating valve leaflets during diastole and systole, respectively, according to an embodiment.
Figure 110:
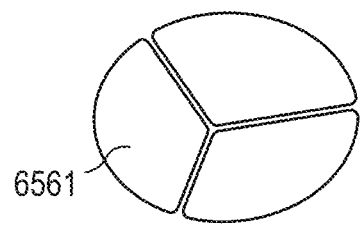

FIGS. 109 and 110 are illustrations of a top view of valve leaflets 6561 during diastole and systole, respectively, according to an embodiment.

Figure 111:
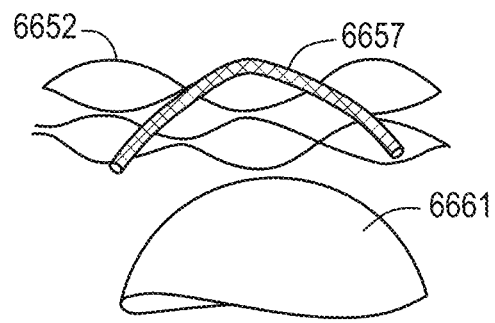
FIG. 111 is a side view illustration of a portion of an inner frame of a flow control component having a semi-rigid arch to provide an additional surface for attaching a leaflet structure to the inner frame, according to an embodiment.

FIG. 111 is an illustration of a detailed side view of a portion of inner wire frame 6652 of a flow control component that shows how a nitinol or other semi-rigid (semi-flexible) arch 6657 can be mounted on a portion of the inner wire frame 6652 to provide an additional surface for suturing a leaflet cusp 6661 to the inner wire frame 6652, according to an embodiment.

FIG. 112 is a flowchart illustrating a method 10 of delivering a transcatheter prosthetic heart valve according to an embodiment. The method 10 folding a side-deliverable prosthetic heart valve along a longitudinal axis such that an inner flow control component elastically deforms in response to the folding, at 11. The prosthetic valve can be any of the valves disclosed herein. For example, the valve can be a valve having (i) a frame with at least a distal anchoring element and a proximal anchoring element, and (ii) a flow control component mounted within the frame configured to permit blood flow in a single direction through an inflow end of the valve and to block blood flow in an opposite direction through an outflow end of the valve. The valve can be delivered via an orthogonal delivery process. For example, the valve can be delivered via any of the processes and/or methods described in detail herein and/or in the '957 PCT or the '010 PCT.

As described in detail above, the flow control component can include an inner frame that is disposed within a central channel of the outer frame of the valve. In some instances, the inner frame can be offset within the central channel, as described in detail above. The inner frame of the flow control component can be formed of a relatively flexible material such as a superelastic material and/or a shape-memory alloy. In some embodiments, the inner frame can include any suitable number of wire cells (e.g., diamond-shaped cells) that can be arranged and/or oriented to allow the inner frame to elastically deform in response to an applied force. In some embodiments, the inner frame can include lateral fold or hinge areas that can allow the inner frame to elastically deform in response to the folding. For example, the fold or hinge areas can be integrated into the inner frame structure and/or can be a connection point between two portions of the inner frame. For example, the inner frame can include a first member and a second member that are flexibly coupled at the lateral fold or hinge areas. Accordingly, such an arrangement can allow the inner frame to elastically deform in response to the folding.

The side deliverable prosthetic heart valve is compressed along a central axis of the outer frame to place the side deliverable prosthetic heart valve in a compressed configuration, wherein the central axis is orthogonal to the longitudinal axis of the valve, at 12. As described in detail above, the valve can be compressible and/or foldable in all directions lateral to the longitudinal axis. For example, the valve can be compressible along the central axis (e.g., a vertical axis) and foldable along or in the direction of a lateral axis (e.g., an axis orthogonal to both the central axis and the longitudinal axis). Moreover, the inner frame of flow control component can be configured to be compressed elastically when the valve is compressed along the central axis. Thus, the flow control component can elastically deform throughout a process of placing the valve in the compressed configuration.

The side-deliverable prosthetic heart valve is inserted into the lumen of a delivery catheter such that the longitudinal axis of the valve is substantially parallel to a lengthwise axis of the delivery catheter, at 13. As described in detail herein and/or in the '957 PCT and/or the '010 PCT, the valve can be delivered orthogonally and compressed vertically and/or laterally to allow a relatively large prosthetic valve to be delivered to a human heart via a transcatheter approach.

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations.

The embodiments described herein can include various combinations and/or sub-combinations of the functions, components, and/or features of the different embodiments described. Various of the above-disclosed and other features and functions, or alternatives thereof, may be combined into many other different systems or applications. Various presently unforeseen or unanticipated alternatives, modifications, variations, or improvements therein may be subsequently made by those skilled in the art, each of which is also intended to be encompassed by the disclosed embodiments.

What is claimed:

1. A side-deliverable prosthetic heart valve, the prosthetic valve comprising:

an outer frame defining a central channel that extends along a central axis of the outer frame; and a flow control component disposed within the central channel and coupled to the outer frame, the flow control component having a two-piece inner frame and a set of leaflets coupled to the two-piece inner frame, the prosthetic valve configured to be folded along a longitudinal axis and compressed along the central axis to place the prosthetic valve in a compressed configuration for delivery via a delivery catheter, the longitudinal axis being substantially parallel to a lengthwise axis of the delivery catheter when the prosthetic valve is disposed therein, the prosthetic valve configured to transition to an expanded configuration when the prosthetic valve is released from the delivery catheter, the two-piece inner frame having a first member and a second member coupled at edge portions thereof to allow the flow control component to elastically deform from a substantially cylindrical configuration to a substantially flattened configuration when the prosthetic valve is placed in the compressed configuration.

2. The prosthetic valve of claim 1, wherein the flow control component is disposed within the central channel and coupled to the outer frame such that an axis defined by the two-piece inner frame of the flow control component is offset from the central axis of the outer frame.

3. The prosthetic valve of claim 2, further comprising:
a spacer disposed within the central channel adjacent to the flow control component.

4. The prosthetic valve of claim 1, wherein each of the first member and the second member of the inner frame has a first edge portion and a second edge portion, the first edge portion of the first member is coupled to the first edge portion of the second member and the second edge portion of the first member is coupled to the second edge portion of the second member.

5. The prosthetic valve of claim 4, wherein the longitudinal axis extends between each of the first edge portions and the second edge portions when the first member and the second member are coupled together to form the two-piece inner frame and the flow control component is coupled to the outer frame, the coupling of the first edge portions and the second edge portions allowing the flow control component to elastically deform to the substantially flattened configuration when the prosthetic valve is placed in the compressed configuration.

6. The prosthetic valve of claim 1, wherein the two-piece inner frame is formed from a shape memory alloy material.

7. The prosthetic valve of claim 1, wherein the two-piece inner frame includes two rows of wire cells, the wire cells having a geometry and orientation configured to allow the two-piece inner frame to be compressed along the central axis.

8. The prosthetic valve of claim 7, wherein the wire cells are at least one of diamond-shaped wire cells or eye-shaped wire cells.

9. A side-deliverable prosthetic heart valve, the prosthetic valve comprising:
an outer frame defining a central channel that extends along a central axis of the outer frame; and a flow control component having a two-piece inner frame and a set of leaflets coupled to the two-piece inner frame, the flow control component configured to be disposed within the central channel and coupled to the outer frame such that an axis defined by the two-piece inner frame of the flow control component is offset from the central axis of the outer frame, the two-piece inner frame having a first member and a second member coupled at edge portions thereof to allow the flow control component to elastically deform between a substantially cylindrical shape and a substantially flattened shape when the prosthetic valve is transitioned between an expanded configuration and a compressed configuration.

10. The prosthetic valve of claim 9, wherein the set of leaflets includes at least two leaflets, the set of leaflets configured to permit blood flow in a first direction through an inflow end of the flow control component and block blood flow in a second direction, opposite the first direction, through an outflow end of the flow control component.

11. The prosthetic valve of claim 9, wherein the outer frame has a body portion that defines the central channel, the body portion has a perimeter with a shape that is based at least in part on a shape of an annulus of a native heart valve, and the two-piece inner frame has a perimeter with the substantially cylindrical shape when the prosthetic valve is in the expanded configuration, the perimeter of the two-piece inner frame being smaller than the perimeter of the body portion of the outer frame.

12. The prosthetic valve of claim 9, wherein the prosthetic valve is configured to be compressed along at least the central axis to the compressed configuration for delivery via a delivery catheter to a desired location in the body, the prosthetic valve is configured to expand to the expanded configuration in response to being released from the delivery catheter.

13. The prosthetic valve of claim 8, wherein each of the first member and the second member of the inner frame has a first edge portion and a second edge portion, the first edge portion of the first member coupled to the first edge portion of the second member, the second edge portion of the first member coupled to the second edge portion of the second member.

14. The prosthetic valve of claim 13, wherein the first edge portion of the first member is coupled to the first edge portion of the second member via sutures and the second edge portion of the first member is coupled to the second edge portion of the second member via sutures.

15. The prosthetic valve of claim 14, wherein the first member and the second member collectively form a perimeter of the two-piece inner frame, the perimeter of the two-piece inner frame having a substantially cylindrical shape when the prosthetic valve is in the expanded configuration.

16. The prosthetic valve of claim 13, wherein the prosthetic valve has a longitudinal axis, the longitudinal axis extending between each of the first edge portions and the second edge portions when the first member and the second member are coupled together to form the two-piece inner frame and the flow control component is coupled to the outer frame.

17. The prosthetic valve of claim 16, wherein the side deliverable prosthetic heart valve is configured to be folded about a plane that is parallel to the longitudinal axis and the central axis when in the compressed configuration.

18. The prosthetic valve of claim 17, wherein the coupling of each of the first edge portions and the second edge portions when the first member and the second member are coupled together to form the two-piece inner frame and the flow control component is coupled to the outer frame allows the inner frame to elastically deform in response to the prosthetic valve being folded about the plane.

19. The prosthetic valve of claim 9, wherein each of the first member and the second member is formed from a shape memory alloy tube.

20. The prosthetic valve of claim 9, wherein each of the first member and the second member is formed from a shape memory alloy sheet.

21. The prosthetic valve of claim 9, wherein the first member includes a plurality of slits arranged perpendicular to the axis of the inner frame and the second member includes a plurality of slits arranged perpendicular to the axis of the inner frame.

22. The prosthetic valve of claim 21, wherein the plurality of slits of the first member and the plurality of slits of the second member form a plurality of diamond-shaped cells of the two-piece inner frame when the prosthetic valve is in the expanded configuration, the plurality of diamond-shaped cells allowing the two-piece inner frame to be elastically compressed along the axis of the two-piece inner frame when the prosthetic valve is in the compressed configuration.

23. The prosthetic valve of claim 22, wherein the plurality of diamond-shaped cells includes a first row of diamond-shaped cells and a second row of diamond-shaped cells coupled to the first row of diamond-shaped cells.

24. A method for compressing a side-deliverable prosthetic heart valve for transcatheter delivery to a desired location in the body, the method comprising:
folding the side-deliverable prosthetic heart valve along a longitudinal axis, the side-deliverable prosthetic heart valve having an outer frame defining a central channel and a flow control component disposed within the central channel and coupled to the outer frame, the flow control component having a two-piece inner frame and a plurality of leaflets coupled to the two-piece inner frame, the two-piece inner frame having a first member and a second member coupled at edge portions thereof to allow the flow control component to elastically deform from a first configuration in which a perimeter of the two-piece inner frame is substantially cylindrical to a second configuration in which a perimeter of the two-piece inner frame is substantially flattened in response to the folding;
compressing the side-deliverable prosthetic heart valve along a central axis of the outer frame to place the side-deliverable prosthetic heart valve in a compressed configuration, the central axis being orthogonal to the longitudinal axis, the central channel extending in the direction of the central axis; and
inserting the side-deliverable prosthetic heart valve in the compressed configuration into a lumen of a delivery catheter such that the longitudinal axis of the side-deliverable prosthetic heart valve is substantially parallel to a lengthwise axis of the delivery catheter.

25. The method of claim 24, wherein flow control component is disposed within the central channel of the outer frame such that an axis defined by the two-piece inner frame is offset from the central axis of the outer frame.

26. The method of claim 24, wherein each of the first member and the second member of the inner frame has a first edge portion and a second edge portion, the first edge portion of the first member configured to be coupled to the first edge portion of the second member, the second edge portion of the first member configured to be coupled to the second edge portion of the second member, the first member and the second member collectively forming the perimeter of the two-piece inner frame.

27. The method of claim 26, wherein the flow control component is coupled to the outer frame such that the longitudinal axis extends between each of the first edge portions and the second edge portions of the first member and the second member.

28. The method of claim 27, wherein the coupling of each of the first edge portions and the second edge portions when the first member and the second member are coupled together to form the two-piece inner frame and the flow control component is coupled to the outer frame allows the flow control component to elastically deform in response to the folding.

29. The method of claim 28, wherein each of the first member and the second member is formed from one of a shape memory alloy sheet or a shape memory alloy tube defining a plurality of slits extending in a direction parallel to the longitudinal axis.

30. The method of claim 29, wherein the plurality of slits of the first member and the plurality of slits of the second member form a plurality of diamond-shaped cells of the two-piece inner frame when the prosthetic valve is in the expanded configuration, the plurality of diamond-shaped cells allowing the two-piece inner frame to be elastically compressed along the central axis when the prosthetic valve is in the compressed configuration.

* * * * *

UNITED STATES PATENT AND TRADEMARK OFFICE
CERTIFICATE OF CORRECTION

| | |
|---|---|
| PATENT NO. | : 11,273,032 B2 |
| APPLICATION NO. | : 17/222182 |
| DATED | : March 15, 2022 |
| INVENTOR(S) | : Mark Christianson et al. |

It is certified that error appears in the above-identified patent and that said Letters Patent is hereby corrected as shown below:

In the Specification

Column 1, Line 24, delete "Control Component for Orthogonal Transcatheter Hear" and insert -- Control Component for Orthogonal Transcatheter Heart --

Column 8, Line 65, delete "Any of the prosthetic hear valves described herein can" and insert -- Any of the prosthetic heart valves described herein can --

Column 9, Line 38, delete "Any of the prosthetic hear valves described herein can" and insert -- Any of the prosthetic heart valves described herein can --

In the Claims

Claim 13, Line 1, delete "The prosthetic valve of claim 8" and insert -- "The prosthetic valve of claim 9 --

Signed and Sealed this
Twelfth Day of July, 2022

Katherine Kelly Vidal
*Director of the United States Patent and Trademark Office*